(12) United States Patent
Martin et al.

(10) Patent No.: US 11,207,321 B2
(45) Date of Patent: Dec. 28, 2021

(54) METHODS AND MEDICAL USES

(71) Applicants: Institute of Cancer Research: Royal Cancer Hospital (The), London (GB); Breast Cancer Now, London (GB)

(72) Inventors: Lesley-Ann Martin, London (GB); Joanna Nikitorwicz-Buniak, London (GB)

(73) Assignees: The Institute of Cancer Research: Royal Cancer Hospital, London (GB); Breast Cancer Now, London (GB)

( * ) Notice: Subject to any disclaimer, the term of this patent is extended or adjusted under 35 U.S.C. 154(b) by 0 days.

(21) Appl. No.: 16/623,953

(22) PCT Filed: Jun. 19, 2018

(86) PCT No.: PCT/GB2018/051697
§ 371 (c)(1),
(2) Date: Dec. 18, 2019

(87) PCT Pub. No.: WO2018/234780
PCT Pub. Date: Dec. 27, 2018

(65) Prior Publication Data
US 2020/0138815 A1    May 7, 2020

(30) Foreign Application Priority Data
Jun. 20, 2017 (GB) .................................... 1709840

(51) Int. Cl.
| | | |
|---|---|---|
| *A61K 31/5025* | (2006.01) | |
| *A61K 31/437* | (2006.01) | |
| *A61K 31/506* | (2006.01) | |
| *A61K 31/517* | (2006.01) | |
| *A61K 31/519* | (2006.01) | |
| *A61K 31/53* | (2006.01) | |
| *A61P 35/00* | (2006.01) | |

(52) U.S. Cl.
CPC ........ *A61K 31/5025* (2013.01); *A61K 31/437* (2013.01); *A61K 31/506* (2013.01); *A61K 31/517* (2013.01); *A61K 31/519* (2013.01); *A61K 31/53* (2013.01); *A61P 35/00* (2018.01)

(58) Field of Classification Search
CPC .............. A61K 2300/00; A61K 31/129; A61K 31/437; A61K 31/4375; A61K 31/472; A61K 31/4725; A61K 31/496; A61K 31/4985; A61K 31/5025; A61K 31/506; A61K 31/517; A61K 31/519; A61K 31/52; A61K 31/565; A61K 31/53; A61P 35/00

See application file for complete search history.

(56) References Cited

U.S. PATENT DOCUMENTS

| | | |
|---|---|---|
| 2,697,710 A | 12/1954 | Hitchings |
| 3,021,332 A | 2/1962 | Hitchings |
| 6,653,332 B2 | 11/2003 | Jaen et al. |
| 6,831,175 B2 | 12/2004 | Li et al. |
| 7,939,551 B2 | 5/2011 | Jaen et al. |
| 9,371,319 B2 | 6/2016 | Bavetsias et al. |
| 9,409,907 B2 | 8/2016 | Hoelder et al. |
| 9,834,552 B2 | 12/2017 | Hoelder et al. |
| 9,890,157 B2 | 2/2018 | Hoelder et al. |
| 9,902,721 B2 | 2/2018 | Woodward et al. |
| 10,399,974 B2 | 9/2019 | Woodward et al. |
| 10,501,462 B2 | 12/2019 | Naud et al. |
| 11,046,688 B2 | 6/2021 | Hoelder et al. |
| 2003/0073668 A1 | 4/2003 | Booth et al. |
| 2003/0105115 A1 | 6/2003 | Metcalf et al. |
| 2004/0092521 A1 | 5/2004 | Altenbach et al. |
| 2005/0256118 A1 | 11/2005 | Altenbach et al. |
| 2005/0272728 A1 | 12/2005 | Altenbach et al. |
| 2011/0257196 A1 | 10/2011 | Lu et al. |
| 2012/0122838 A1 | 5/2012 | Ren et al. |
| 2012/0258857 A1 | 10/2012 | Pham et al. |
| 2013/0345181 A1* | 12/2013 | Bavetsias ............. C07D 471/04 514/158 |
| 2015/0031672 A1 | 1/2015 | Ren et al. |
| 2015/0157606 A1 | 6/2015 | Chow Maneval et al. |
| 2015/0218181 A1* | 8/2015 | Hoelder ............... A61K 31/519 514/210.18 |
| 2015/0239884 A1* | 8/2015 | Hoelder ............... A61K 31/519 514/210.18 |

(Continued)

FOREIGN PATENT DOCUMENTS

| | | |
|---|---|---|
| EP | 1463505 A2 | 10/2004 |
| WO | WO-1996/015128 A2 | 5/1996 |

(Continued)

OTHER PUBLICATIONS

Aguilera et al., "c-Jun N-terminal Phosphorylation Antagonises Recruitment of the Mbd3/NuRD Repressor Complex," Nature, 469(7329): 231-236 (2011).

Alajarin et al., "Unprecedented Intramolecular [3+2] Cycloadditions of Azido-ketenimines and Azido-Carboiimides. Synthesis of lndolo[1,2-a]quinazolines and Tetrazolo[5,1-b]quinazolines," Org Biomol Chem, 9(19): 6741-6749 (2011).

Balog et al., "Novel fluorescent isoquinoline derivatives obtained via Buchwald-Hartwig coupling of isoquinolin-3-amines", *Arkivoc*, vol. 5, 109-119 (2012).

(Continued)

*Primary Examiner* — Erich A Leeser
(74) *Attorney, Agent, or Firm* — Foley Hoag LLP; David P. Halstead; Lawrence P. Tardibono

(57) ABSTRACT

The invention described herein provides a method for the treatment of an oestrogen receptor positive breast cancer in a subject in need thereof comprising administering to said subject a therapeutically effective amount of a compound capable of inhibiting MPS1, wherein:
(i) said subject has previously been treated with a CDK4/6 inhibitor; and/or
(ii) said breast cancer is resistant to treatment with a CDK4/6 inhibitor.

32 Claims, 5 Drawing Sheets

(56) References Cited

U.S. PATENT DOCUMENTS

| | | |
|---|---|---|
| 2016/0000787 A1 | 1/2016 | Broude et al. |
| 2016/0008365 A1 | 1/2016 | Zhu et al. |
| 2016/0362409 A1* | 12/2016 | Woodward ........... A61K 31/519 |
| 2017/0107577 A1 | 4/2017 | Al-Ejeh |
| 2018/0141944 A1 | 5/2018 | Hoelder et al. |
| 2018/0194761 A1 | 7/2018 | Woodward et al. |
| 2020/0138815 A1 | 5/2020 | Martin et al. |
| 2020/0165241 A1 | 5/2020 | Hoelder et al. |
| 2020/0171032 A1 | 6/2020 | Martin et al. |

FOREIGN PATENT DOCUMENTS

| | | |
|---|---|---|
| WO | WO-2001/055147 A1 | 8/2001 |
| WO | WO-2002/090360 A1 | 11/2002 |
| WO | WO-2003/051366 A2 | 6/2003 |
| WO | WO-2003/074530 A1 | 9/2003 |
| WO | WO-2004/043458 A1 | 5/2004 |
| WO | WO-2004/065378 A1 | 8/2004 |
| WO | WO-2007/000240 A1 | 1/2007 |
| WO | WO-2007/117607 A2 | 10/2007 |
| WO | WO-2007/125405 A2 | 11/2007 |
| WO | WO-2007/140222 A2 | 12/2007 |
| WO | WO-2008/079988 A2 | 7/2008 |
| WO | WO-2008/135232 A1 | 11/2008 |
| WO | WO-2009/032694 A1 | 3/2009 |
| WO | WO-2009/084695 A1 | 7/2009 |
| WO | WO-2009/103966 A1 | 8/2009 |
| WO | WO-2010/007374 A1 | 1/2010 |
| WO | WO-2010/129816 A2 | 11/2010 |
| WO | WO-2011/090738 A2 | 7/2011 |
| WO | WO-2012/013557 A1 | 2/2012 |
| WO | WO-2012/028756 A1 | 3/2012 |
| WO | WO-2012/052540 A1 | 4/2012 |
| WO | WO-2012/064973 A2 | 5/2012 |
| WO | WO-2012/080284 A2 | 6/2012 |
| WO | WO-2012/088438 A1 | 6/2012 |
| WO | WO-2012/092471 A2 | 7/2012 |
| WO | WO-2012/101032 A2 | 8/2012 |
| WO | WO-2012/123745 A1 | 9/2012 |
| WO | WO-2013/053051 A1 | 4/2013 |
| WO | WO-2014/037750 A1 | 3/2014 |
| WO | WO-2014/037751 A1 | 3/2014 |
| WO | WO-2015/128676 A1 | 9/2015 |
| WO | WO-2016/073771 A2 | 5/2016 |
| WO | WO-2017/109476 A1 | 6/2017 |

OTHER PUBLICATIONS

Bathini et al., "2-Aminoquinazoline inhibitors of cyclin-dependent kinases", *Bioorg. Med. Chem. Lett.* vol. 15(17), 3881-3885 (2005).
Bruce et al., "The Kinome associated with estrogen receptor-positive status in human breast cancer," Endocrine-Related Cancer, 21(5): R357-R370 (2014).
Cabarello et al., "2D Autocorrelation, CoMFA, and CoMSIA modeling of protein tyrosine kinases' inhibition by substituted pyrido[2,3-d]pyrimidine derivatives", *Bioorg. Med. Chem.*, vol. 16(2), 810-821 (2008).
Clinicaltrials.gov, "Phase I Dose Escalation of Oral BAY1161909 in Combination With Intravenous Paclitaxel," NLM Identifier: NCT02138812, National Library of Medicine (US), Available from: <https://clinicaltrials.gov/ct2/show/NCT02138812> (2014).
Clinicaltrials.gov, "Phase I Study of Oral BAY 1217389 in Combination With Intravenous Paclitaxel," NLM Identifier: NCT02366949, National Library of Medicine (US), Available from: <https://clinicaltrials.gov/ct2/show/NCT02366949> (2015).
Clinicaltrials.gov, "Study of Paclitaxel in Combination With BOS172722 in Patients With Advanced Nonhaematologic Malignancies," NLM Identifier: NCT03328494, National Library of Medicine (US), Available from: <https://clinicaltrials.gov/ct2/show/study/NCT03328494> (2017).
Database PubChem Compounds [Online] Dec. 1, 2012, Database accession No. CID 70113665, abstract.
Database PubChem Compounds [Online] Jul. 13, 2005, Database accession No. CID 2000835, abstract.
Database PubChem Compounds [Online] Jul. 13, 2005, Database accession No. CID 2004801, abstract.
Database PubChem Compounds [Online] Jul. 13, 2005, Database accession No. CID 2019230, abstract.
Database PubChem Compounds [Online] Jul. 9, 2005, Database accession No. CID 940974, abstract.
Database PubChem Compounds [Online] Jul. 9, 2005, Database accession No. CID 945107, abstract.
Database PubChem Compounds [Online] Jul. 9, 2005, Database accession No. CID 945815, abstract.
Database PubChem Compounds [Online] NCBI; Dec. 1, 2012 Database accession No. CID 69975764, abstract.
Database PubChem Compounds [Online] NCBI; Sep. 13, 2005, Database accession No. CID 4000352, abstract.
Database Registry [Online] Chemical Abstracts Service, Columbus, Ohio, US; Jan. 19, 2004, Database accession No. 639005-15-5, abstract.
Dowsett et al., "Biological characteristics of the pure antiestrogen fulvestrant: overcoming endocrine resistance," Breast Cancer Research and Treatment 93: S11-S18 (2005).
Gyorffy et al., "TP53 mutation-correlated genes predict the risk of tumor relapse and identify MPS1 as a potential therapeutic kinase in TP53-mutated breast cancers," Molecular Oncology, 8:508-519 (2014).
He et al., "Synthesis and SAR of Novel Quinazolines as Potent and Brain-penetrant c-jun N-terminal Kinase (JNK) Inhibitors," Bioorg Med Chem Lett, 21(6): 1719-1723 (2011).
Henriques et al., "Mitosis inhibitors in anticancer therapy: When blocking the exit becomes a Solution," Cancer Letters 440-441:64-81 (2019).
Herrera-Abreu et al., "Early Adaptation and Acquired Resistance to CDK4/6 Inhibition in Estrogen Receptor-Positive Breast Cancer," Cancer Research, 76(8): 2301-2313 (2016).
International Search Report and Written Opinion for International Application No. PCT/GB2013/052360 dated Oct. 15, 2013.
International Search Report and Written Opinion for International Application No. PCT/GB2015/050590 dated Apr. 9, 2015.
International Search Report and Written Opinion for International Application No. PCT/GB2016/054003 dated Mar. 10, 2017.
International Search Report and Written Opinion for International Application No. PCT/GB2018/051694 dated Oct. 23, 2018.
International Search Report and Written Opinion for International Application No. PCT/GB2018/051697 dated Oct. 31, 2018.
Jansen et al., "Abstract 2844: RNA interference kinome-wide screen reveals a role for PDK1 in acquired resistance to CDK4/6 inhibition ER-positive breast cancer," Cancer Research, abstract (Aug. 2015), 5 pages.
Jansen et al., "Abstract P3-03-05: PI3K/PD1 mediates resistance to CDK4/6 inhibitors through dysregulation of S-phase cyclins/cyclin dependent kinases (CDKs)," Cancer Research, abstract (Feb. 2017), 5 pages.
Jemaa, "Characterization of novel MPS1 inhibitors with preclinical anticancer activity" Cell Death and Differentiation 20:1532-1545 (2013).
Kumar, "Lead optimization of purine based orally bioavailable Mps1 (TTK) inhibitors," Bioorganic & Medicinal Chemistry Letters 22:4377-4385 (2012).
Kusakabe et al., "A unique hinge binder of extremely selective aminopyridine-based Mps1 (TTK) kinase inhibitors with cellular activity," Bioorganic & Medicinal Chemistry 23(9):2247-2260 (2015).
Lainchbury et al., "Discovery of 3-Alkoxyamino-5-(pyridin-2-ylamino)pyrazine-2-carbonitriles as Selective, Orally Bioavailable CHK1 Inhibitors", J. Med. Chem., vol. 55(22), 10229-10240 (2012).
Martin et al., "Abstract P3-03-09: Resistance to palbociclib depends on multiple targetable mechanisms highlighting the potential of drug holidays and drug switching to improve therapeutic outcome," Cancer Research, abstract (Dec. 2016), 5 pages.
Mason et al., "Functional characterization of CFI-402257, a potent and selective Mps1/TTK Kinase inhibitor, for the treatment of cancer," PNAS, 114(12): 3127-3132 (2017).

(56) References Cited

OTHER PUBLICATIONS

Naud et al., "Structure-based Design of Orally Bioavailable 1H-pyrrolo[3,2-c]pyridine Inhibitors of Mitotic Kinase Monopolar Spindle 1 (MPS1)," Journal of Medicinal Chemistry, 56:10045-10065 (2013).
Nikitorowicz-Buniak et al., "Abstract 4950: MPS1 as a novel target in endocrine and palbociclib-resistant estrogen receptor positive breast cancer," Cancer Research, abstract (Apr. 2018), 5 pages.
Nikitorowicz-Buniak et al., "Abstract P1-09-03: Global Knockdown of cellular kinases identifies MPS1 as a novel modulator of endocrine and palbociclib resistance highlighting a new role for MPS1 inhibitors," Cancer Research, abstract (Feb. 2018), 5 pages.
Proisy et al., "Rapid synthesis of 3-aminoisoquinoline-5-sulfonamides using the Buchwald-Hartwig reaction," Synthesis, 4: 561-566 (2009).
Ranjitkar et al., "Affinity-Based Probes Based on Type II Kinase Inhibitors", J. Am. Chem. Soc. vol. 134(16), 19017-19025 (2012).
Reader et al., "Structure-Guided Evolution of Potent and Selective CHK1 Inhibitors through Scaffold Morphing," J Med Chem, 54(24): 8328-8342 (2011).
Scifinder Search Report, pp. 1-104, Aug. 20, 2012.
Sugimoto et al., "Novel pyrrolopyrimidines as Mps1/TTK Kinase inhibitors for breast cancer," Bioorganic & Medicinal Chemistry, 25: 2156-2166 (2017).
Thompson et al., "Synthesis and Structure-Activity Relationships of 7-Substituted 3-(2,6-Dichlorophenyl)-1,6-naphthyridin-2(1H)-ones as Selective Inhibitors of pp60", J. Med. Chem. Lett., vol. 43(16), 3134-3147 (2000).
Trumpp-Kallmeyer et al., "Development of a Binding Model to Protein Tyrosine Kinases for Substituted Pyrido[2,3-d]pyrimidine Inhibitors", J. Med. Chem., vol. 41(11), 1752-1763 (1998).
Uitdehaag et al., "Target Residence Time-Guided Optimization on TTK Kinase Results in Inhibitors with Potent Anti-Proliferative Activity," Journal of Molecular Biology, 429: 2211-2230 (2017).
UK Search Report for GB Application No. GB1216017.2 dated Mar. 7, 2013.
UK Search Report for GB Application No. GB1403536.4 dated Sep. 8, 2014.
UK Search Report for GB Application No. GB1522532.9 dated Oct. 11, 2016.
UK Search Report for GB Application No. GB1709837.7 dated Mar. 19, 2018.
UK Search Report for GB Application No. GB1709840.1 dated Mar. 19, 2018.
Walton et al., "The Preclinical Pharmacology and Therapeutic Activity of the Novel CHK1 Inhibitor SAR-020106," Mol Cancer Ther, 9: 89 (2010).
Weigel et al., "Abstract 2920: Experimental and clinical studies reveal the PDGF/Abl pathway as a novel therapeutic target in endocrine-resistant breast cancer" Cancer Research, 70(8): abstract (2010).
Xie et al., "Mps1/TTK: a novel target and biomarker for cancer" J Drug Targeting 25(2):112-118 (2017).

* cited by examiner

METHODS AND MEDICAL USES

RELATED APPLICATIONS

This application is a U.S. National Stage Application of International Application No. PCT/GB18/51697 filed Jun. 19, 2018, which claims the benefit of priority to Great Britain Application No. 1709840.1 filed Jun. 20, 2017. The entire contents of PCT/GB18/51697 are incorporated herein by reference in their entirety.

The present invention provides new methods of treatment and medical uses relating to the treatment of CDK4/6-resistant, oestrogen receptor-positive breast cancer. Furthermore, the present invention provides combinations suitable for the treatment of breast cancer.

BACKGROUND OF THE INVENTION

It has long been recognised that many breast cancers are hormone dependent. Oestrogen (may be interchangeably referred to as estrogen), in particular, acts as an endocrine growth factor in a large proportion of breast cancers. Thus depriving these tumours of oestrogen is a major treatment modality in breast cancer.

The most commonly diagnosed breast cancer (BC) in the clinic is oestrogen receptor-(ER) positive and ER-positive BC accounts for over 80% of cases.

Oestrogen mediates its effects by binding to the ER. Oestrogen bound ER associates classically with oestrogen response elements (EREs) on target genes controlling proliferation and cell survival. ER has two distinct activation domains, AF-1 and AF-2. AF-2 is integral to the ligand-binding domain and is regulated by the binding of oestrogen. AF-1 activity is regulated by phosphorylation whilst AF-2 associates with coactivators of the p160 family, controlling the ER transcriptional complex.

Classically, patients with ER-positive BC are treated with endocrine agents such as tamoxifen or aromatase inhibitors (AI), which impede oestrogen signalling.

Although over 50% of patients show response to endocrine therapy, a large proportion relapse with de novo or acquired resistant disease, making it one of the greatest challenges for breast cancer research (reviewed by Ma et al. 2015). One striking feature of endocrine-resistant BC is the fact that the majority of patients continue to express ER. To date, multiple molecular mechanisms have been implicated in the resistant phenotype, all of which converge at the level of cyclin D, forcing cell cycle progression. This high degree of heterogeneity in adaptive mechanisms during the course of ER-positive BC progression highlights the importance of finding common nodes attributed to therapeutic failure.

As uncontrolled proliferation is a hallmark of cancer (reviewed by Hanahan & Weinberg 2011) direct targeting of cell cycle with CDK inhibitors has provided an attractive proposition but until recently few have shown specificity and associated clinical toxicities have been unacceptable (Asghar et al. 2015). The CDK4/6-RB axis is critical for cell cycle entry and, not surprisingly, most cancers subvert this axis to promote proliferation, for instance 19% of breast cancers show amplification of CDK4 whilst, CCND1 amplification is associated with endocrine resistance (reviewed Musgrove et al. 2011).

Recently, the combination of CDK4/6 inhibitors with endocrine therapy has been shown to improve clinical outcome in ER+ breast cancer patients. However, not all patients will benefit from such combination therapy and many will eventually relapse with acquired resistance.

There is a need in the art for new treatment options in respect of breast cancer. In particular, there is a need in the art for new, effective therapies for treating CDK4/6 inhibitor-resistant breast cancer.

SUMMARY OF THE INVENTION

Herein, it is shown for the first time that MPS1 is surprisingly associated with resistance to CDK4/6 inhibitors, and furthermore that MPS1 provides a rational target for the treatment of breast cancers which are resistant to CDK4/6 inhibitors.

In one aspect, the present invention relates to a method for the treatment of an oestrogen receptor positive breast cancer in a subject in need thereof comprising administering to said subject a therapeutically effective amount of an MPS1 inhibitor, wherein:
(i) said subject has previously been treated with a CDK4/6 inhibitor; and/or
(ii) said breast cancer is resistant to treatment with a CDK4/6 inhibitor.

In one aspect, the present invention relates to an MPS1 inhibitor for use in the treatment of an oestrogen receptor-positive breast cancer in a subject in need thereof, wherein:
(i) the subject has previously been treated with a CDK4/6 inhibitor; and/or
(ii) the breast cancer is resistant to treatment with a CDK4/6 inhibitor.

In one aspect, the present invention relates to a use of a MPS1 inhibitor in the manufacture of a medicament for the treatment of an oestrogen receptor positive breast cancer in a subject in need thereof, wherein:
(i) the subject has been previously treated with a CDK4/6 inhibitor; and/or
(ii) the breast cancer is resistant to treatment with a CDK4/6 inhibitor.

In one aspect, the present invention relates to a combination comprising an MPS1 inhibitor and a CDK4/6 inhibitor.

In one aspect, the present invention relates to a pharmaceutical product comprising an MPS1 inhibitor and a CDK4/6 inhibitor.

In one aspect, the present invention relates to a method for the treatment of oestrogen receptor positive breast cancer in a subject in need thereof comprising administering to said subject, either separately, sequentially or in combination, a therapeutically effective amount of an MPS1 inhibitor and a therapeutically effective amount of a CDK4/6 inhibitor.

In one aspect, the present invention relates to a pharmaceutical product comprising an MPS1 inhibitor and a CDK4/6 inhibitor for use in the treatment of an oestrogen receptor positive breast cancer, wherein the MPS1 inhibitor and the CDK4/6 inhibitor are for separate, sequential or combined administration.

In one aspect, the present invention relates to the use of a pharmaceutical product comprising an MPS1 inhibitor and a CDK4/6 inhibitor in the manufacture of a medicament for the treatment of oestrogen receptor positive breast cancer, wherein the MPS1 inhibitor and the CDK4/6 inhibitor are for separate, sequential or combined administration.

In one aspect, the present invention relates to an MPS1 inhibitor and a CDK4/6 inhibitor for use in the treatment of estrogen receptor-positive breast cancer.

In one aspect, the present invention relates to an MPS1 inhibitor for use in the treatment of estrogen receptor-positive breast cancer, wherein said MPS1 inhibitor is for separate, sequential or combined administration with a CDK4/6 inhibitor.

In one aspect, the present invention relates to a CDK4/6 inhibitor for use in the treatment of estrogen receptor-positive breast cancer, wherein said CDK4/6 inhibitor is for separate, sequential or combined administration with an MPS1 inhibitor.

In one aspect, the present invention relates to a use of an MPS1 inhibitor and a CDK4/6 inhibitor in the manufacture of a medicament for the treatment of estrogen receptor-positive breast cancer.

In one aspect, the present invention relates to a use of an MPS1 inhibitor in the manufacture of a medicament for the treatment of estrogen receptor-positive breast cancer, wherein said MPS1 inhibitor is for separate, sequential or combined administration with a CDK4/6 inhibitor.

In one aspect, the present invention relates to a use of a CDK4/6 inhibitor in the manufacture of a medicament for the treatment of estrogen receptor-positive breast cancer, wherein said CDK4/6 inhibitor is for separate, sequential or combined administration with an MPS1 inhibitor.

Preferred, suitable, and optional features of any one particular aspect of the present invention are also preferred, suitable, and optional features of any other aspect.

DETAILED DESCRIPTION OF THE INVENTION

Definitions

Figure 1A:
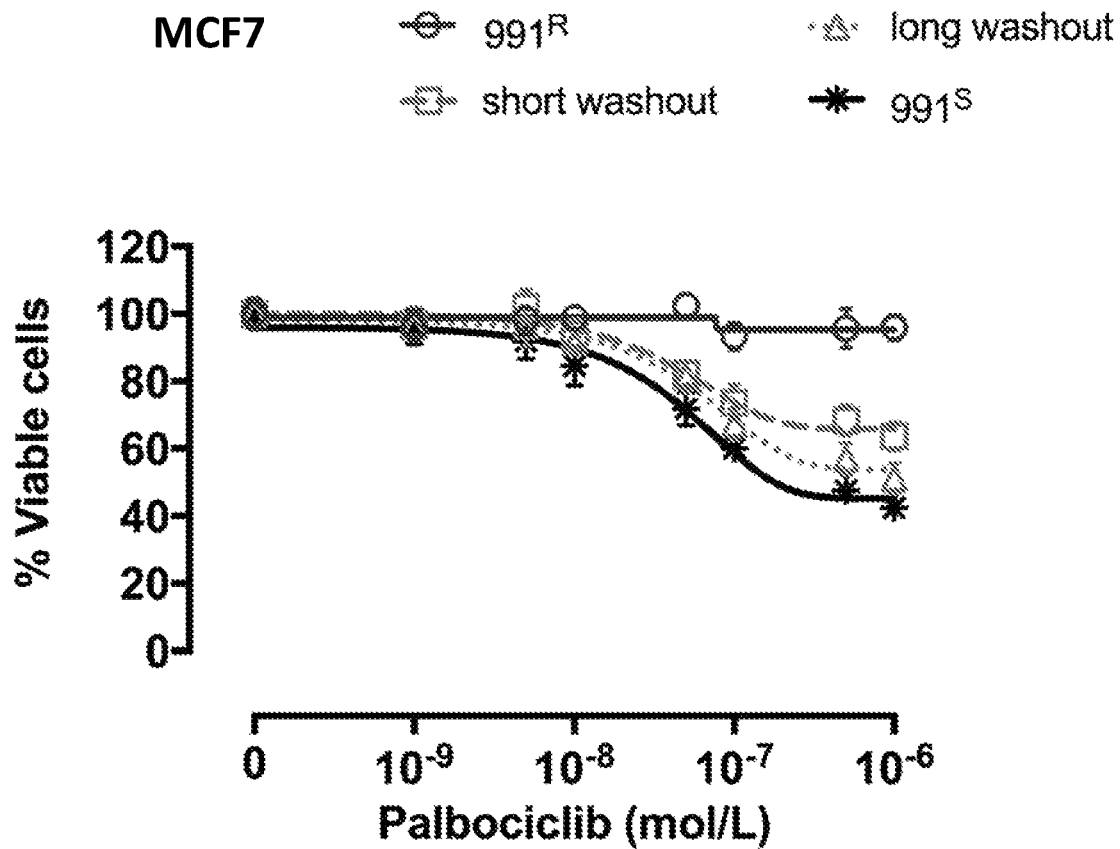
FIGS. 1A and 1B show the results of proliferation assays in palbociclib resistant and sensitive lines.
Figure 1A:
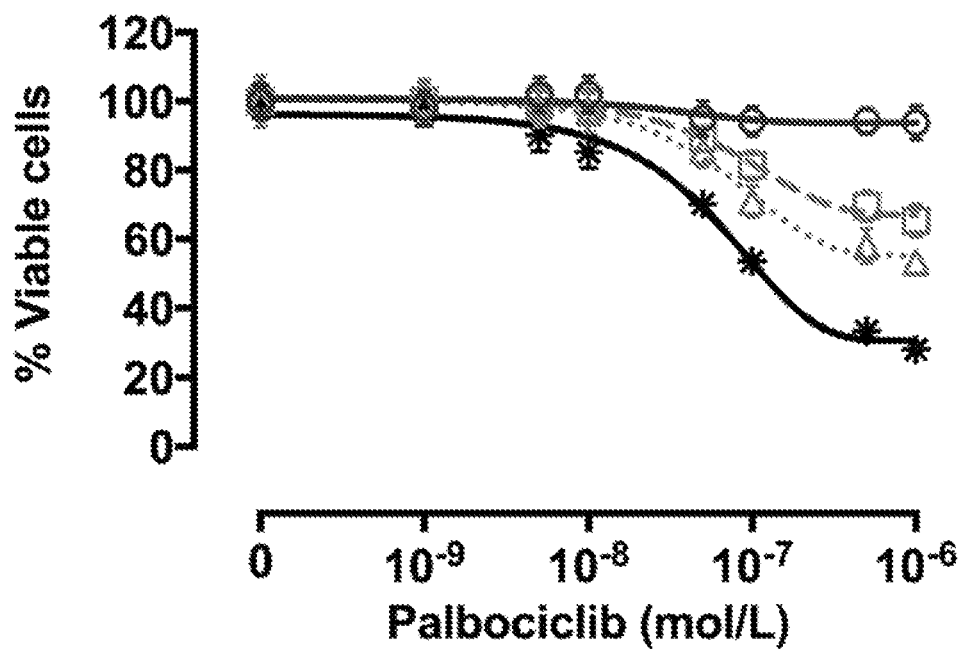
Figure 1B:
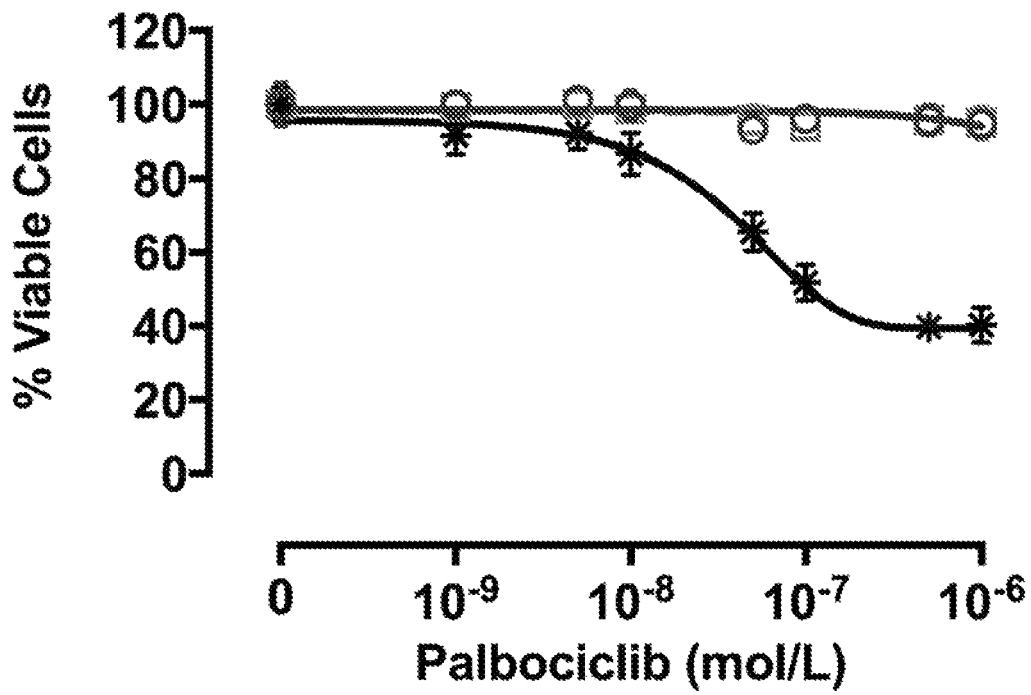
Figure 1B:
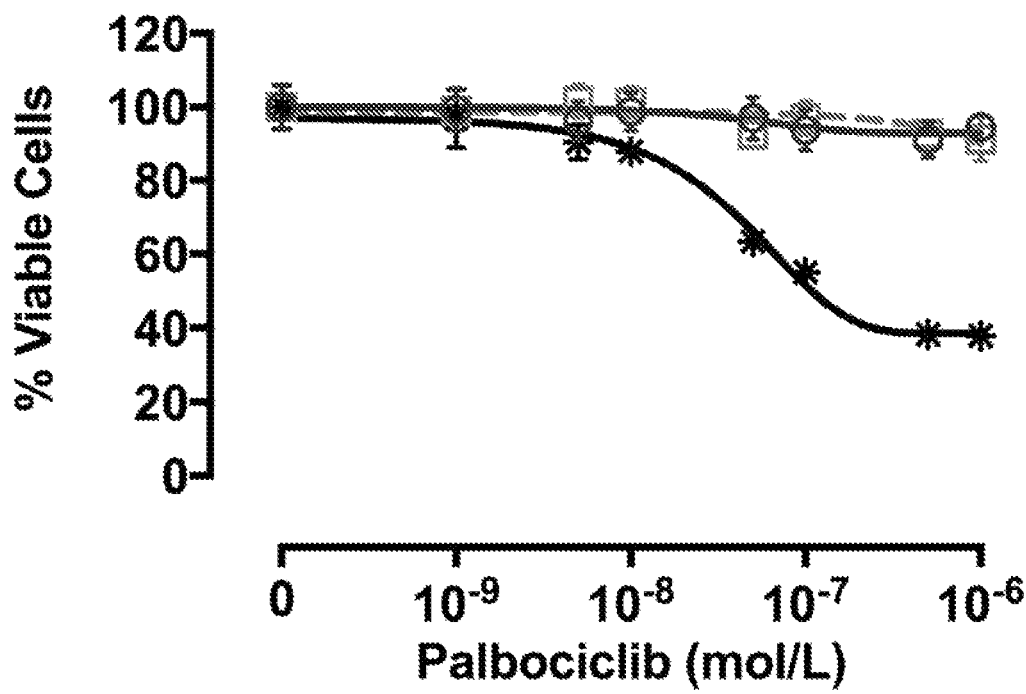

As used herein, "oestrogen receptor-positive (ER+) breast cancer" refers to a breast cancer which naturally expresses oestrogen receptors (suitably nuclear oestrogen receptors; suitably ER-alpha). Any suitable technique known in the art may be used to identify if a breast cancer expresses oestrogen receptors, including ligand-binding assays and immunohistochemical techniques.

As used herein, the term CDK4/6 inhibitor refers to chemical or biological agents capable of inhibiting CDK4 and CDK6. Suitably, the CDK4/6 inhibitors are selective for CDK 4 and 6 over other kinases, particularly over other CDKs. Suitably, the CDK4/6 inhibitors herein have nanomolar $IC_{50}$s at CDK4 and CDK6. Suitably, the CDK4/6 inhibitors are chemical compounds, e.g. a drug or a drug-like molecules.

As used herein, the "failed previous treatment" may mean said subject has been determined by a relevant skilled person to have failed treatment, for instance, with a CDK4/6 inhibitor or an endocrine therapy. A relevant skilled person would readily be able to determine when a subject has failed treatment, for instance with a CDK4/6 inhibitor or with an endocrine therapy. For instance, failure of treatment with a CDK 4/6 inhibitor and/or an endocrine therapy may manifest as one or more of the following during or following therapy: disease progression (e.g. growth of the cancer, relapse, recurrence, spread of the cancer, increased tumour grade, increased proliferation), lack of response (i.e. no pathological change in the cancer, no change in tumour size) and insufficient response (insufficient decrease in tumour size, insufficient pathological response).

As used herein "combined administration" refers to therapy in which the both agents (e.g. an MPS1 inhibitor and a CDK4/6 inhibitor) are administered simultaneously.

As used herein "sequential administration" means that one agent is administered after the other, however, the time period between the administration of each agent is such that both agents are capable of acting therapeutically concurrently. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between the administration of the agents may vary depending on the exact nature of the agents, the interaction there between, and their respective half-lives.

As used herein, "separate administration" means that one agent is administered after the other, however, the time period between administration is such that the first administered agent is no longer present a therapeutically effective amount when the second agent is administered. Accordingly, the two agents exert their therapeutic effects separately. Nevertheless, the overall therapeutic effect observed when the two agents separately act therapeutically may be greater than either agent used alone.

As used herein the, "subject(s)" and/or "patient(s)", suitably refer to mammals (e.g. humans and non-human mammals such as livestock (cows, sheep, goats) or companion animals (cats, dogs, horses, rabbits). Suitably, the subject(s) and/or patient(s) are human(s).

As used herein "resistant to a CDK4/6 inhibitor" or "CDK4/6-resistant" cancer may mean said cancer has been determined by a relevant skilled person to be resistant to a CDK4/6 inhibitor. A relevant skilled person would readily be able to determine when a cancer is resistant to a CDK4/6 inhibitor. For instance, clinically, resistance can manifest as relapse or cancer recurrence during or following treatment with a CDK4/6 inhibitor. Alternatively, resistance can be observed as clinical progression of primary disease, usually constituting an increase in primary tumour size or disease spread to regional nodes or beyond to more distant metastatic sites. Pathological changes such as increased tumour grade or increased proliferation are indicators of potential resistance to therapy. In the neoadjuvant setting, resistance occurs as either a primary lack of response (no change or an increase in tumour size and no evidence of pathological response) early in treatment, implying innate or de novo resistance, or later following a period of response, suggesting acquired resistance. Alternatively, resistance to a CDK4/6 inhibitor may be determined in CDK4/6 inhibitor-nave patients by reference to genotypic and/or phenotypic markers of resistance.

As used herein "resistant to endocrine therapy" or "endocrine-resistant" cancer may mean said cancer has been determined by a relevant skilled person to be resistant to endocrine therapy. A relevant skilled person would readily be able to determine when a cancer is resistant to endocrine therapy. For instance, clinically, resistance can manifest as relapse or cancer recurrence during or following endocrine therapy. Alternatively, resistance can be observed as clinical progression of primary disease, usually constituting an increase in primary tumour size or disease spread to regional nodes or beyond to more distant metastatic sites. Pathological changes such as increased tumour grade or increased proliferation are indicators of potential resistance to therapy. In the neoadjuvant setting, resistance occurs as either a primary lack of response (no change or an increase in tumour size and no evidence of pathological response) early in treatment, implying innate or de novo resistance, or later following a period of response, suggesting acquired resistance. Alternatively, resistance to endocrine therapy may be determined in endocrine therapy nave patients by reference to genotypic and/or phenotypic markers of resistance.

As used herein the term "endocrine therapy" refers to any treatment capable of removing oestrogen, blocking generation of oestrogen, reducing levels of oestrogen, blocking the effect of oestrogen, reducing the effect of oestrogen and/or can lead to instability, degradation and/or down regulation of the oestrogen receptor. Suitably, the endocrine therapy comprises/essentially consists of/consists of administration of an endocrine agent.

As used herein, the term "endocrine agent" refers to any chemical compound or biological agent capable of removing oestrogen, blocking generation of oestrogen and/or reducing levels of oestrogen. Suitably, the endocrine agent is a chemical compound, e.g. a drug or a drug-like molecule.

As used herein, the term MPS1 inhibitor refers to a chemical or biological agent capable of inhibiting MPS1 (monopolar spindle 1) kinase. Suitably, the MPS1 inhibitors are selective for MPS1 over other kinases. Suitably, the MPS1 inhibitors herein have nanomolar $IC_{50}$s at MPS1. Suitably, the MPS1 inhibitors are chemical compounds, e.g. a drug or a drug-like molecule.

As used herein the term "BAY 1161909" refers to the following compound:

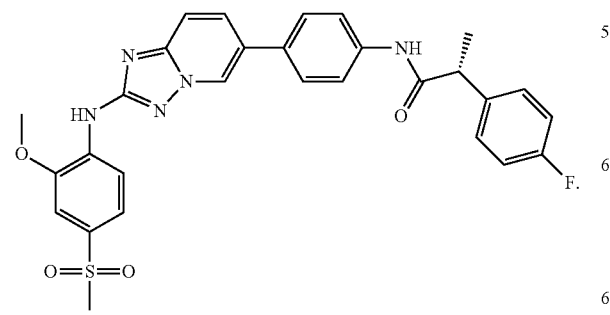

As used herein the term "BAY 1217389" refers to the following compound:

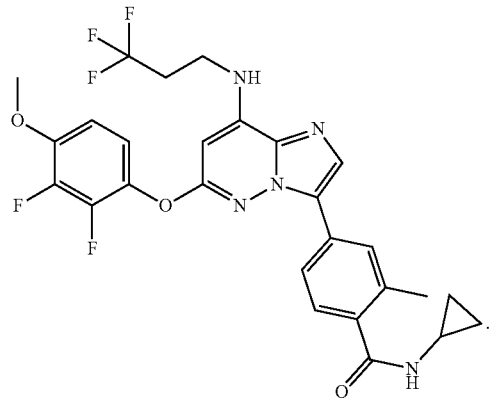 [SMILES: COc1ccc(Oc2cc(NCCC(F)(F)F)c3ncc(-c4ccc(C(=O)NC5CC5)c(C)c4)n3n2)c(F)c1F]

As used herein the term "NMS-P715" refers to the following compound:

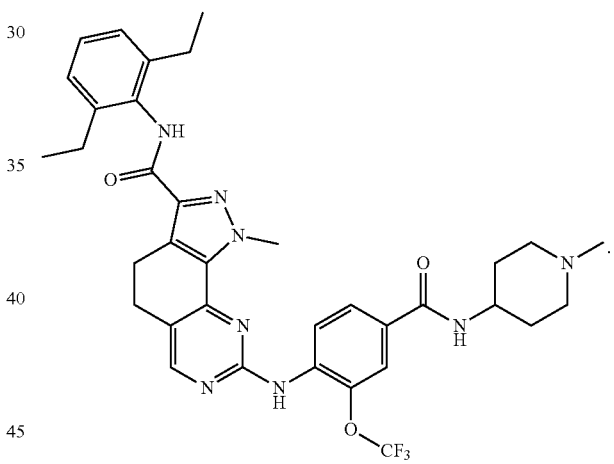

As used herein the term "AZ3146" refers to the following compound:

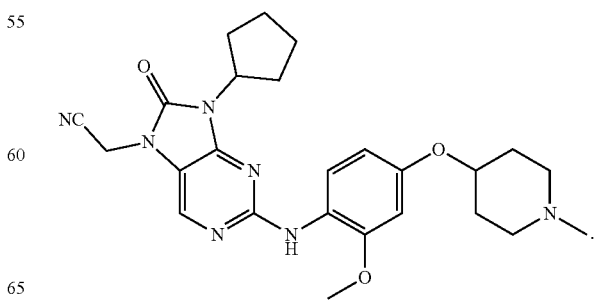

As used herein the term "MPS1-IN-3" refers to the following compound:

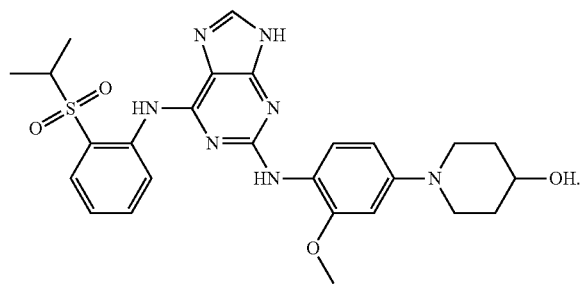 [SMILES: COc1cc(N2CCC(O)CC2)ccc1Nc1nc(Nc2ccccc2S(=O)(=O)C(C)C)c2nc[nH]c2n1]

As used herein the term "MPS1-IN-2" refers to the following compound:

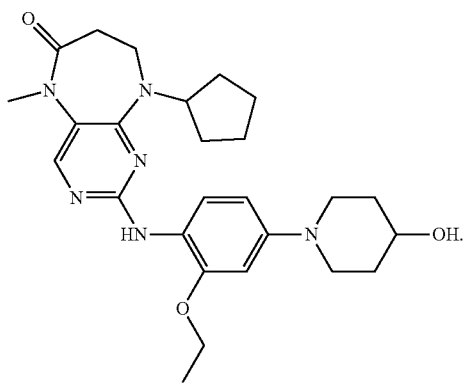 [SMILES: CCOc1cc(N2CCC(O)CC2)ccc1Nc1ncc2c(n1)N(C1CCCC1)CCC(=O)N2C]

As used herein the term "CFI-402257" refers to the following compound:

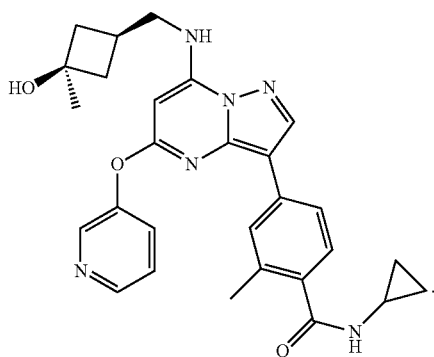 [SMILES: Cc1cc(-c2cnn3c(NC[C@H]4C[C@@](C)(O)C4)cc(Oc4cccnc4)nc23)ccc1C(=O)NC1CC1]

As used herein the term "CCT289346" refers to N2-(2-ethoxy-4-(4-methyl-4H-1,2,4-triazol-3-yl)phenyl)-6-methyl-N8-neopentylpyrido[3,4-d]pyrimidine-2,8-diamine.

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", may refer to medical actions and results and includes prophylactic, ameliorative, palliative, and curative actions and results. In some embodiments, the terms "treating", "treated", and "treatment" refer to curative actions and results as well as actions and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to actions and results where the administration of a compound or composition diminishes the likelihood or seriousness of a condition, symptom, or disease state, and/or delays the onset of a condition, symptom, or disease state for a period of time.

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I" and the more general term "compounds" refer to and include any and all compounds described by and/or with reference to Formula I. As applies mutatis mutandis to the terms "compounds of Formula II", "compounds of Formula III", "compounds of Formula IV" and "compounds of Formula V". It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formulae I, II, III, IV and V either by themselves or in combination with additional agents.

The various hydrocarbon-containing moieties provided herein may be described using a prefix designating the minimum and maximum number of carbon atoms in the moiety, e.g. "$(C_{a-b})$" or "$C_a$-$C_b$" or "(a-b)C". For example, $(C_{a-b})$alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene ($CH_2$), the ethylene isomers ($CH(CH_3)$ and $CH_2CH_2$), the propylene isomers ($CH(CH_3)CH_2$, $CH(CH_2CH_3)$, $C(CH_3)_3$, and $CH_2CH_2CH_2$), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl and naphthyl, suitably phenyl.

As used herein by themselves or in conjunction with another term or terms, "arylene" and "arylene group" refer to a phenylene ($—C_6H_4—$) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2—$). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydronaphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Suitably, cycloalkyl groups are selected from cyclopropyl, cyclobutyl, cyclopentyl and cyclohexyl groups.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2—$). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —Cl=CH$_2$, —C≡C—CF$_3$, —CHFCH$_2$CH$_3$ and —CHFCH$_2$CF$_3$. Haloalkyl groups can be substituted or unsubstituted. Suitably, a haloalkyl group is selected from CHF$_2$ and CF$_3$, suitably CF$_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Haloalkoxy includes both saturated alkoxy groups as well as unsaturated alkenyl and alkynyl groups. Representative examples include, but are not limited to, —OCF$_3$, —OCHF$_2$, —OCH$_2$F, —OCF$_2$CF$_3$, —OCHFCF$_3$, —OCH$_2$CF$_3$, —OCF$_2$CH$_3$, —OCHFCH$_3$, —OCF$_2$CF$_2$CF$_3$, —OCF$_2$CH$_2$CH$_3$, —OCF=CF$_2$, —OCCl=CH$_2$, —OCBr=CH$_2$, —OCHFCH$_2$CH$_3$ and —OCHFCH$_2$CF$_3$. Haloalkoxy groups can be substituted or unsubstituted. Suitably, a haloalkyoxy group is selected from —OCHF$_2$ and —OCF$_3$, suitably —OCF$_3$.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7), 3,5-trienyl, 12-aza-tricyclo[7.2.1.0$^{2,7}$]dodeca-2 (7),3,5-trienyl, 10-aza-tricyclo[6.3.2.0$^{2,7}$]trideca-2(7), 3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Where carbon numbers are provided, e.g. (C$_{n-m}$)alkylheteroaryl, the range refers to the whole group. Suitably, the constituent alkyl group has 1-6 carbons, suitable 1-3 carbons.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide,

[1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2$—). Alkylheteroycloalkyl groups can be substituted or unsubstituted. Where carbon numbers are provided, e.g. ($C_{n-m}$)alkylheterocycloalkyl, the range refers to the whole group. Suitably, the constituent alkyl group has 1-6 carbons, suitable 1-3 carbons.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—$CH_3$), it can be optionally substituted by 1 to 3 $R^5$.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein, a "pharmaceutical product" refers to a product comprising a pharmaceutical. For instance, examples of a pharmaceutical product include a medical device, a pharmaceutical composition and a kit comprising one or more medical device and/or pharmaceutical composition. Suitably, the pharmaceutical product is a pharmaceutical composition.

Methods of Treatment and Medical Uses

In one aspect, the present invention relates to a method for the treatment of an oestrogen receptor positive breast cancer in a subject in need thereof comprising administering to said subject a therapeutically effective amount of an MPS1 inhibitor, wherein:
(i) said subject has previously been treated with a CDK4/6 inhibitor; and/or
(ii) said breast cancer is resistant to treatment with a CDK4/6 inhibitor In one aspect, the present invention relates to an MPS1 inhibitor for use in the treatment of an oestrogen receptor-positive breast cancer in a subject in need thereof, wherein:
(i) the subject has previously been treated with a CDK4/6 inhibitor; and/or
(ii) the breast cancer is resistant to treatment with a CDK4/6 inhibitor.

In one aspect, the present invention relates to a use of a MPS1 inhibitor in the manufacture of a medicament for the treatment of an oestrogen receptor positive breast cancer in a subject in need thereof, wherein:
(i) the subject has been previously treated with a CDK4/6 inhibitor; and/or
(ii) the breast cancer is resistant to treatment with a CDK4/6 inhibitor.

In one embodiment of each of the above aspects, the subject has been previously treated with a CDK4/6 inhibitor. Typically, the need for further treatment implies that the previous treatment with the CDK4/6 inhibitor has failed.

The relevant skilled person would be readily able to determine treatment failure. In one embodiment, failure of treatment with a CDK4/6 inhibitor in a subject manifests as relapse and/or cancer recurrence during or following treatment with a CDK4/6 inhibitor.

In one embodiment of each of the aspects or embodiments herein, failure of treatment with a CDK4/6 inhibitor in a subject is observed as disease progression during or following treatment with the CDK4/6 inhibitor, for example, an increase in primary tumour size and/or spread of disease; for example, to regional nodes or beyond to more distant metastatic sites.

In one embodiment of each of the aspects or embodiments herein, failure of treatment with a CDK4/6 inhibitor in a subject is determined by pathological changes, such as increased tumour grade.

In one embodiment of each of the aspects or embodiments herein, failure of treatment with a CDK4/6 inhibitor in a subject is determined by increased proliferation of the cancer.

In one embodiment of each of the aspects or embodiments herein, failure of treatment with a CDK4/6 inhibitor in the subject is observed as a lack of response of the cancer; for example, no significant/insufficient change in tumour size and/or no significant/insufficient level of pathological response.

In one embodiment of each of the aspects or embodiments herein, the subject has developed a CDK4/6 inhibitor-resistant breast cancer during or following treatment with a CDK4/6 inhibitor. This phenomenon may be referred to as acquired resistance.

In one embodiment of each of the aspects and embodiments herein, the breast cancer is resistant to treatment with a CDK4/6 inhibitor. In one embodiment, the CDK4/6 inhibitor-resistance is observed during or following treatment with a CDK4/6 inhibitor, which may have initially resulted in a positive response (i.e. acquired resistance). In another embodiment, the CDK4/6 inhibitor-resistance is observed early in treatment with a CDK4/6 inhibitor without a period positive response, implying innate or de novo resistance. In another embodiment, the subject/breast cancer is CDK4/6 inhibitor-nave and resistance is indicated by phenotypic or genotypic markers.

In one embodiment of each of the aspects herein, the breast cancer is resistant to treatment with a CDK4/6 inhibitor and the subject is CDK4/6 inhibitor-nave.

In one embodiment of each of the aspects herein, the breast cancer is de novo resistant to treatment with a CDK4/6 inhibitor.

In one embodiment of each of the above aspects, the subject has been previously treated with an endocrine therapy. Typically, the need for further treatment implies that the previous endocrine therapy has failed.

The relevant skilled person would be readily able to determine treatment failure. In one embodiment, failure of endocrine therapy treatment in a subject manifests as relapse and/or cancer recurrence during or following endocrine therapy.

In one embodiment of each of the aspects or embodiments herein, failure of endocrine therapy treatment in a subject is observed as disease progression during or following endocrine therapy, for example, an increase in primary tumour size and/or spread of disease; for example, to regional nodes or beyond to more distant metastatic sites.

In one embodiment of each of the aspects or embodiments herein, failure of endocrine therapy treatment in a subject is determined by pathological changes, such as increased tumour grade.

In one embodiment of each of the aspects or embodiments herein, failure of endocrine therapy treatment in a subject is determined by increased proliferation of the cancer.

In one embodiment of each of the aspects or embodiments herein, failure of endocrine therapy treatment in the subject is observed as a lack of response of the cancer; for example, no significant/insufficient change in tumour size and/or no significant/insufficient level of pathological response.

In one embodiment of each of the aspects or embodiments herein, the subject has developed an endocrine therapy-resistant breast cancer during or following endocrine therapy. This phenomenon may be referred to as acquired resistance.

In one embodiment of each of the aspects and embodiments herein, the breast cancer is resistant to endocrine therapy. In one embodiment, the endocrine therapy resistance is observed during or following endocrine therapy, which may have initially resulted in a positive response (i.e. acquired resistance). In another embodiment, the endocrine therapy resistance is observed early in endocrine therapy without a period positive response, implying innate or de novo resistance. In another embodiment, the breast cancer/subject is endocrine therapy-nave and resistance is indicated by phenotypic or genotypic markers.

In one embodiment of each of the aspects herein, the breast cancer is resistant to endocrine therapy and the subject is endocrine therapy-nave.

In one embodiment of each of the aspects herein, the breast cancer is de novo resistant to endocrine therapy.

In one embodiment of each of the aspects herein, the breast cancer is resistant to endocrine therapy and continues to express oestrogen receptors, in particular, ER-alpha.

In one embodiment of each of the aspects herein, the breast cancer harbours an ESR1-activating mutation. Suitably, the ESR1-activating mutation is selected from Y537S, Y537N, Y537C, D538G, E380Q, S463P, L536R. Suitably, the ESR1-activating mutation is selected from Y537S, Y537N and Y537C. Suitably, the ESR1-activating mutation is Y537C.

In one embodiment of each of the aspects herein, the breast cancer is resistant to endocrine therapy and harbours an ESR1-activating mutation. Suitably, the ESR1-activating mutation is selected from Y537S, Y537N, Y537C, D538G, E380Q, S463P, L536R. Suitably, the ESR1-activating mutation is selected from Y537S, Y537N and Y537C. Suitably, the ESR1-activating mutation is Y537C.

In one embodiment of each of the aspects herein, the breast cancer overexpresses phospho-KNL1 protein.

In one embodiment of each of the aspects herein, the breast cancer is resistant to endocrine therapy and the breast cancer overexpresses phospho-KNL1 protein.

In one embodiment of each of the aspects and embodiments herein, the MPS1 inhibitor is administered/for administration either separately, sequentially and/or combination with a CDK4/6 inhibitor.

In one aspect, the present invention provides the use of an MPS1 inhibitor as a second or third-line therapy for the treatment of oestrogen receptor position breast cancer, in particular, CDK4/6 inhibitor-resistant ER+ breast cancer.

In one embodiment, the MPS1 inhibitor is used as a second line therapy and the first line therapy comprised treatment with a CDK4/6 inhibitor. In another embodiment, the MPS1 inhibitor is used as a third line therapy and at least one of the first and second line therapies comprised treatment with a CDK4/6 inhibitor.

In one embodiment of each of the aspects and embodiments herein, the subject is a human. Suitably, the subject is a female human.

In one embodiment of each of the aspects and embodiments herein, the subject is post-menopausal. In another embodiment of each of the aspects and embodiments herein, the subject is pre-menopausal.

In the methods and medical uses of the invention the MPS1 inhibitors and/or the CDK4/6 inhibitors may be administered/for administration to the subject by any convenient route of administration.

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly. Suitably, the route of administration is selected from oral and parenteral injection.

The therapeutic agents (i.e. MPS1 inhibitors, CDK4/6 inhibitors, endocrine agents) for use in the methods herein may be in a form suitable for administration to a subject. For instance for oral use tablets, lozenges, hard or soft capsules, aqueous or oily suspensions, emulsions, dispersible powders or granules, syrups or elixirs; for topical use creams, ointments, gels, or aqueous or oily solutions or suspensions); for administration by inhalation a finely divided powder or a liquid aerosol; for administration by insufflation a finely divided powder); or for parenteral administration a sterile aqueous or oily solution for intravenous, subcutaneous, intramuscular, intraperitoneal or intramuscular dosing; or as a suppository for rectal dosing.

Suitable pharmaceutical compositions may be obtained by conventional procedures optionally using conventional pharmaceutical excipients, well known in the art. Thus, compositions intended for oral use may contain, for example, one or more colouring, sweetening, flavouring and/or preservative agents.

An effective amount of the agents (i.e. MPS1 inhibitors, CDK4/6 inhibitors, endocrine agents) of the methods herein is an amount sufficient to treat or prevent said breast cancer referred to herein, slow disease progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of an agent will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

CDK4/6 Inhibitor

In one embodiment of each of the aspects and embodiments herein, the CDK4/6 inhibitor is selected from one or more of palbociclib, abemaciclib and ribociclib, or pharmaceutically acceptable salts or solvates thereof.

Suitably, the CDK4/6 inhibitor is selected from one or more of palbociclib and ribociclib, or pharmaceutically acceptable salts or solvates thereof.

Suitably, the CDK4/6 inhibitor is selected from one or more of palbociclib and abemaciclib, or pharmaceutically acceptable salts or solvates thereof.

Suitably, the CDK4/6 inhibitor is selected from one or more of ribociclib and abemaciclib, or pharmaceutically acceptable salts or solvates thereof.

Suitably, the CDK4/6 inhibitor is palbociclib, or pharmaceutically acceptable salts or solvates thereof.

MPS1 Inhibitors

In one embodiment of the aspects and embodiments herein, the MPS1 inhibitor is a compound capable of inhibiting MPS1 kinase. Suitably, the compound has an $IC_{50}$ at MPS1 kinase of 100 nM or less. Suitably, the compound has an $IC_{50}$ at MPS1 kinase of 75 nM or less. Suitably, the compound has an $IC_{50}$ at MPS1 kinase of 50 nM or less. Suitably, the compound has an $IC_{50}$ at MPS1 kinase of 25 nM or less. Suitably, the compound has an $IC_{50}$ at MPS1 kinase of 10 nM or less. Suitably, the compound has an $IC_{50}$ at MPS1 kinase of 8 nM or less. Suitably, the compound has an $IC_{50}$ at MPS1 kinase of 5 nM or less. Suitably, the compound has an $IC_{50}$ at MPS1 kinase of 3 nM or less.

The $IC_{50}$ at MPS1 kinase may be determined by any suitable method. For example, the $IC_{50}$ may be determined by in vitro enzyme inhibition assay comprising full length MPS1, a suitable fluorophore, test compound and an assay buffer.

Suitably, $IC_{50}$s are determined by testing the compounds at a range of concentrations.

Suitably, the fluorophore can be a fluorescent labelled peptide, for example, H236, which has the sequence: 5FAM-DHTGFLTEYVATR-$CONH_2$.

Suitably, the enzyme inhibition assay is carried out at room temperature (21° C.±3° C.) for about one hour.

In one embodiment, the enzyme inhibition assay (total volume 10 µl) was carried out in black 384-well low volume plates containing full length MPS1 (12.5 nM or 3 nM), fluorescent labelled peptide [known as H236, which has the sequence: 5FAM-DHTGFLTEYVATR-$CONH_2$] (5 µM), ATP (10 µM), either DMSO (1% v/v) or the test compound (in the range 0.25 nM-100 µM in 1% DMSO) and assay buffer (50 mM HEPES (pH 7.0), 0.02% $NaN_3$, 0.01% BSA, 0.1 mM Orthovandate, 10 µM $MgCl_2$, 1 µM DTT, Roche protease inhibitor). The reaction was carried out for 60 min at room temperature and stopped by the addition of buffer (10 µl) containing 20 mM EDTA, 0.05% (v/v) Brij-35, in 0.1M HEPES-buffered saline (Free acid, Sigma, UK). The plate was read on a Caliper EZ reader 11 (Caliper Life Sciences).

The reader provides a Software package ('Reviewer') which converts the peak heights into % conversion by measuring both product and substrate peak and also allows selection of control well which represent 0% and 100% inhibition, respectively. The % inhibition of the compounds is calculated relative to the means of selected control wells. $IC_{50}$s are determined by testing the compounds at a range of concentrations from 0.25 nM-100 µM. The % inhibitions at each concentration are then fitted to a 4 parameter logistic fit:

$$y=(a+((b-a)/(1+((c/x\char`\^d))))$$

where a=asym min, b=asym max, c=$IC_{50}$ and d=hill coefficient

In one embodiment of each of the aspects and embodiment herein, the MPS1 inhibitor is selected from the group consisting of NMS-P715, S 81694 (NMS-P153), AZ3146, BAY 1217389, BAY 1161909, MPS1-IN-3, MPS1-IN-2, CFI-402257, CCT289346, a compound of formula I, a compound of formula II, a compound of formula III and a compound of formula IV, or a pharmaceutically acceptable salt or solvate thereof;

wherein formula I is:

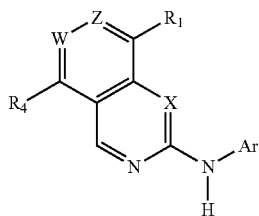

wherein:
W is N or C—$R_3$;
X is CH or N;
Z is N or C—H;
$R_1$ is selected from chloro, (1-6C)alkyl, (1-8C)heteroalkyl, aryl, aryl(1-2C)alkyl, heteroaryl, heteroaryl(1-2C)alkyl, heterocyclyl, heterocyclyl(1-2C)alkyl, (3-8C)cycloalkyl, (3-8C)cycloalkyl(1-2C)alkyl, $NR_7R_8$, $OR_9$, $C(O)R_9$, $C(O)OR_9$, $OC(O)R_9$, $N(R_{10})OR_9$, $N(R_{10})C(O)OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SO_2R_9$, $N(R_{10})SOR_9$ or $SON(R_{10})R_9$;

and wherein $R_1$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_qCH_3$ (where q is 0, 1 or 2), methylamino or dimethylamino, aryl, aryl(1-2C)alkyl, heteroaryl, heteroaryl(1-2C)alkyl, heterocyclyl, heterocyclyl(1-2C)alkyl, (3-8C)cycloalkyl, or (3-8C)cycloalkyl(1-2C)alkyl, and wherein any (1-4C)alkyl, (1-4C)alkoxy, aryl, heteroaryl, heterocyclyl, or (3-8C)cycloalkyl moiety present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;
$R_3$ is hydrogen, (1-4C)alkyl, (3-6C)cycloalkyl, halo, $CF_3$, CN and (1-4C)alkoxy;
$R_4$ is hydrogen, (1-3C)alkyl, (1-3C)alkoxy, fluoro, chloro or $CF_3$;
Ar has the formula:

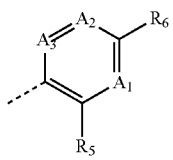

wherein:
(i) all of $A_1$, $A_2$ and $A_3$ are CH;
(ii) one of $A_1$, $A_2$ and $A_3$ is N and the others are CH; or
(iii) two of $A_1$, $A_2$ and $A_3$ are N and the other is CH;

$R_5$ is selected from hydrogen, cyano, (1-3C)alkyl, (1-3C)fluoroalkyl, (1-3C)alkoxy, (1-3C)fluoroalkoxy, halo, (1-3C)alkanoyl, $C(O)NR_{15}R_{16}$ or $S(O)_2NR_{15}R_{16}$, and wherein $R_{15}$ and $R_{16}$ are each independently selected from H or (1-3C)alkyl,
and wherein any alkyl or alkoxy moieties present within a $R_5$ substituent group are optionally further substituted by hydroxy or methoxy;
$R_6$ is selected from halo, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl,
or $R_6$ is a group of the formula:

$$-L^1-L^2-R_{17}$$

wherein
$L^1$ is absent or a linker group of the formula —$[CR_{18}R_{19}]_n$— in which n is an integer selected from 1, 2, 3 or 4, and $R_{19}$ and $R_{19}$ are each independently selected from hydrogen or (1-2C)alkyl;
$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{21})SO_2$, wherein $R_{20}$ and $R_{21}$ are each independently selected from hydrogen or (1-2C)alkyl; and
$R_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl,
and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl;
and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2(1-2C)$alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);
or $R_{17}$ is a group having the formula:

$$-L^3-L^4-R_{24}$$

$L^3$ is absent or a linker group of the formula —$[CR_{25}R_{26}]_n$— in which n is an integer selected from 1, 2, 3 or 4, and $R_{26}$ and $R_{26}$ are each independently selected from hydrogen or (1-2C)alkyl;
$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and
$R_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl;
$R_8$ and $R_9$ are each independently selected from hydrogen, (1-6C)alkyl, (1-6C)alkoxy, (3-9C)cycloalkyl, (3-9C)cycloalkyl-(1-2C)alkyl, aryl, aryl-(1-2C)alkyl, heterocyclyl, heterocyclyl-(1-2C)alkyl, heteroaryl, heteroaryl-(1-2C)alkyl, and wherein $R_8$ and $R_9$ are optionally further substituted by one or more substituents selected from hydroxy, fluoro, chloro, cyano, $CF_3$, $OCF_3$ (1-2C)alkyl or (1-2C)alkoxy;

$R_7$ and $R_{10}$ are independently selected from hydrogen, (1-6C)alkyl, (3-6C)cycloalkyl, (3-6C)cycloalkyl-(1-2C)alkyl, and wherein $R_7$ and $R_{10}$ are optionally further substituted by one or more substituents selected from hydroxy, fluoro, chloro, cyano, $CF_3$, $OCF_3$, (1-2C)alkyl or (1-2C)alkoxy;

optionally subject to the proviso that:
  X is only N when Z is N;
  W is only N when X and Z are both N; and
  $R_6$ is not methoxy when $R_1$ is $S(O)_2R_9$ and $R_9$ is heterocyclyl;

wherein formula II is:

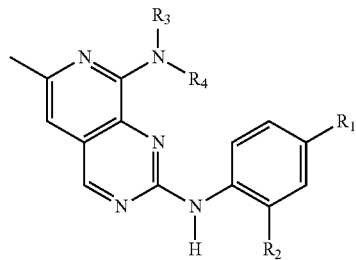

II wherein:
$R_1$ is selected from:
  (i) a 5- or 6-membered heteroaryl optionally substituted with one or more substituents independently selected from halo, trifluoromethyl, difluoromethyl, trifluoromethoxy, difluoromethoxy, cyano, nitro, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$,
  wherein $R_a$ and $R_b$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_qR_c$ (where q is 0, 1 or 2), $SO_2N(R_d)R_c$, or $N(R_d)SO_2R_c$, wherein $R_c$ and $R_d$ are each independently selected from H or (1-4C)alkyl; or
  wherein the 5- or 6-membered heteroaryl is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-4C)alkyl, $NR_kR_1$, $OR_k$, $C(O)R_k$, $C(O)OR_k$, $OC(O)R_k$, $N(R_1)OR_k$, $C(O)N(R_1)R_k$, $N(R_1)C(O)R_k$, $S(O)_pR_k$ (where p is 0, 1 or 2), $SO_2N(R_k)R_1$, or $N(R_k)SO_2R_1$, wherein $R_k$ and $R_1$ are each independently selected from H or (1-4C)alkyl,
  and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_mR_n$, $OR_m$, $C(O)R_m$, $C(O)OR_m$, $OC(O)R_m$, $N(R_n)OR_m$, $C(O)N(R_n)R_m$, $N(R_n)C(O)R_m$, $S(O)_qR_m$ (where q is 0, 1 or 2), $SO_2N(R_n)R_m$, or $N(R_n)SO_2R_m$, wherein $R_m$ and $R_n$ are each independently selected from H or (1-4C)alkyl; or (ii) a group $—C(O)N(R_f)R_e—$ or $—S(O)_2N(R_f)R_e—$;
  wherein $R_e$ and $R_f$ are each independently selected from H or (1-4C)alkyl which is optionally substituted by halo or (1-2C)alkoxy;
  or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-4C)alkyl, $NR_gR_h$, $OR_g$, $C(O)R_g$, $C(O)OR_g$, $OC(O)R_g$, $N(R_h)OR_g$, $C(O)N(R_h)R_g$, $N(R_h)C(O)R_g$, $S(O)_pR_h$ (where p is 0, 1 or 2), $SO_2N(R_h)R_g$, or $N(R_h)SO_2R_g$, wherein $R_g$ and $R_h$ are each independently selected from H or (1-4C)alkyl;

$R_2$ is selected from hydrogen, fluoro, chloro, (1-3C)alkoxy or (1-3C)fluoroalkoxy;

and either:
  (i) $R_3$ is selected from hydrogen or (1-3C)alkyl and $R_4$ is selected from (1-6C)alkyl, (3-9C)cycloalkyl, (3-9C)cycloalkyl-(1-4C)alkyl, aryl, aryl-(1-4C)alkyl, heterocyclyl, heterocyclyl-(1-4C)alkyl, heteroaryl, heteroaryl-(1-4C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$, $OR_o$, $C(O)R_o$, $C(O)OR_o$, $OC(O)R_o$, $N(R_p)OR_o$, $C(O)N(R_p)R_o$, $N(R_p)C(O)R_o$, $S(O)_pR_o$ (where p is 0, 1 or 2), $SO_2N(R_p)R_o$, or $N(R_p)SO_2R_o$ or (3-6C)cycloalkyl, (3-6C)cycloalkyl-(1-2C)alkyl, a 4, 5 or 6-membered heterocyclyl, a 4, 5 or 6-membered heterocyclyl-(1-2C)alkyl, wherein $R_o$ and $R_p$ are each independently selected from H or (1-4C)alkyl, (3-6C)cycloalkyl or (3-6C)cycloalkyl-(1-4C)alkyl; or (ii) $R_3$ and $R_4$ are linked such that, together with the nitrogen atom to which they are attached, they form a nitrogen-linked 4-, 5-6- or 7-membered heterocyclic ring,
wherein said ring is optionally fused to a further 3-, 4-, 5- or 6-membered ring carbocyclic or heterocyclic ring, a 5- or 6-membered heteroaryl ring or a phenyl ring to form a bi-cyclic heterocyclic system, or
linked through a spiro carbon atom to a further 4-, 5- or 6-membered ring carbocyclic or heterocyclic ring to form a spiro bicyclic ring system;
and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $C(O)OR_i$, $OC(O)R_i$, $N(R_j)OR_i$, $C(O)N(R_j)R_i$, $N(R_j)C(O)R_i$, $S(O)_qR_i$ (where q is 0, 1 or 2), $SO_2N(R_j)R_i$, or $N(R_j)SO_2R_i$, wherein $R_i$ and $R_j$ are each independently selected from H or (1-4C)alkyl;

optionally with the proviso that said compound is not one of the following:
N2-(2-methoxy-4-(1-methyl-1H-pyrazol-4-yl)phenyl)-6-methyl-N8-neopentylpyrido[3,4-d]pyrimidine-2,8-diamine;
N2-(4-(1,2-dimethyl-1H-imidazol-5-yl)-2-methoxyphenyl)-N8-(2-methoxy-2-methylpropyl)-6-methylpyrido[3,4-d]pyrimidine-2,8-diamine;
N2-(4-(1,2-dimethyl-1H-imidazol-5-yl)-2-methoxyphenyl)-6-methyl-N8-neopentylpyrido[3,4-d]pyrimidine-2,8-diamine;
N2-(2-methoxy-4-(4-methyl-4H-1,2,4-triazol-3-yl)phenyl)-6-methyl-N8-neopentylpyrido[3,4-d]pyrimidine-2,8-diamine;

N8-(2-methoxy-2-methylpropyl)-N2-(2-methoxy-4-(4-methyl-4H-1,2,4-triazol-3-yl)phenyl)-6-methylpyrido[3,4-d]pyrimidine-2,8-diamine;

N2-(2-methoxy-4-(1-(2-methoxyethyl)-2-methyl-1H-imidazol-5-yl)phenyl)-6-methyl-N8-neopentylpyrido[3,4-d]pyrimidine-2,8-diamine;

N2-(2-ethoxy-4-(4-methyl-4H-1,2,4-triazol-3-yl)phenyl)-6-methyl-N8-neopentylpyrido[3,4-d]pyrimidine-2,8-diamine;

N2-(2-methoxy-4-(4-(methylsulfonyl)piperazin-1-yl)phenyl)-6-methyl-N8-neopentylpyrido[3,4-d]pyrimidine-2,8-diamine;

N2-(4-(1,3-dimethyl-1H-pyrazol-4-yl)-2-methoxyphenyl)-N8-(2-methoxy-2-methylpropyl)-6-methylpyrido[3,4-d]pyrimidine-2,8-diamine;

N-(2-ethoxy-4-(4-methyl-4H-1,2,4-triazol-3-yl)phenyl)-6-methyl-8-(6-oxa-2-azaspiro[3.4]octan-2-yl)pyrido[3,4-d]pyrimidin-2-amine;

N8-(2-methoxy-2-methylpropyl)-N2-(2-methoxy-4-(1-methyl-1H-1,2,4-triazol-5-yl)phenyl)-6-methylpyrido[3,4-d]pyrimidine-2,8-diamine;

N2-(2-(difluoromethoxy)-4-(1-methyl-1H-pyrazol-4-yl)phenyl)-N8-(2-methoxy-2-methylpropyl)-6-methylpyrido[3,4-d]pyrimidine-2,8-diamine;

(4-(3-methoxy-4-((8-((2-methoxy-2-methylpropyl)amino)-6-methylpyrido[3,4-d]pyrimidin-2-yl)amino)phenyl)-1-methyl-1H-pyrazol-5-yl)methanol;

wherein formula III is

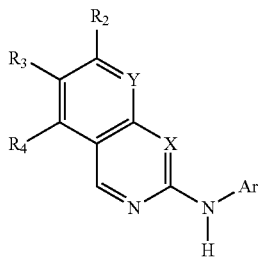

wherein:
X is CH or N;
Y is N or C—H;
$R_2$ is selected from (1-6C)alkyl, (1-8C)heteroalkyl, aryl, aryl(1-2C)alkyl, a 5 or 6 membered heteroaryl, a 5 or 6 membered heteroaryl(1-2C)alkyl, a 3 to 6 membered heterocyclyl, a 3 to 6 membered heterocyclyl(1-2C)alkyl, (3-8C)cycloalkyl, (3-8C)cycloalkyl(1-2C)alkyl, $NR_{11}R_{12}$, $OR_{13}$, $C(O)R_{13}$, $C(O)OR_{13}$, $OC(O)R_{13}$, $N(R_{14})OR_{13}$, $N(R_{14})C(O)OR_{13}$, $C(O)N(R_{14})R_{13}$, $N(R_{14})C(O)R_{13}$, $S(O)_xR_{13}$ (where x is 0, 1 or 2), $SO_2N(R_{14})R_{13}$, or $N(R_{14})SO_2R_{13}$;

and wherein $R_2$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_xCH_3$ (where x is 0, 1 or 2), methylamino or dimethylamino, aryl, aryl(1-2C)alkyl, heteroaryl, heteroaryl(1-2C)alkyl, heterocyclyl, heterocyclyl(1-2C)alkyl, (3-8C)cycloalkyl, or (3-8C)cycloalkyl(1-2C)alkyl, and wherein any (1-4C)alkyl, (1-4C)alkoxy, aryl, heteroaryl, heterocyclyl, or (3-8C)cycloalkyl moiety present within a substituent group on $R_2$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_yR_c$ (where y is 0, 1 or 2), $SO_2N(R_d)R_c$, or $N(R_d)SO_2R_c$, wherein $R_c$ and $R_d$ are each independently selected from H or (1-4C)alkyl;

$R_3$ is hydrogen, (1-4C)alkyl, (3-6C)cycloalkyl, halo, $CF_3$, CN and (1-4C)alkoxy;

$R_4$ is hydrogen, (1-3C)alkyl, fluoro, chloro or $CF_3$;

Ar has the formula:

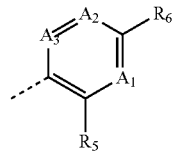

wherein:
(i) all of $A_1$, $A_2$ and $A_3$ are CH; or
(ii) $A_3$ is CH and $A_1$ or $A_2$ are selected from N or CH;

$R_5$ is hydrogen, cyano, (1-3C)alkyl, (1-3C)fluoroalkyl, (1-3C)alkoxy, (1-3C)fluoroalkoxy, halo, (1-3C)alkanoyl, $C(O)NR_{15}R_{16}$ or $S(O)_2NR_{15}R_{16}$, and wherein $R_{15}$ and Rib are each independently selected from H or (1-3C)alkyl, and wherein any alkyl or alkoxy moieties present within a $R_5$ substituent group are optionally further substituted by hydroxy or methoxy;

$R_6$ is halogeno, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or $R_6$ is a group of the formula:

$-L^1-L^2-R_{17}$ wherein
$L^1$ is absent or a linker group of the formula $[CR_{18}R_{19}]_n$— in which n is an integer selected from 1, 2, 3 or 4, and $R_{18}$ and $R_{19}$ are each independently selected from hydrogen or (1-2C)alkyl;

$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{21})SO_2$, wherein $R_{20}$ and $R_{21}$ are each independently selected from hydrogen or (1-2C)alkyl; and $R_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);

or $R_{17}$ is a group having the formula:

-L³-L⁴-R₂₄ wherein
  $L^3$ is absent or a linker group of the formula —[$CR_{25}R_{26}$]$_n$— in which n is an integer selected from 1, 2, 3 or 4, and $R_{25}$ and $R_{26}$ are each independently selected from hydrogen or (1-2C)alkyl;
  $L^4$ is absent or is selected from O, S, SO, $SO_2$, $N(R_{27})$, C(O), C(O)O, OC(O), $CH(OR_{27})$, C(O)N($R_{27}$), $N(R_{27})$C(O), $N(R_{27})$C(O)N($R_{28}$), $S(O)_2$N($R_{27}$), or $N(R_{28})SO_2$, wherein $R_{27}$ and $R_{28}$ are each independently selected from hydrogen or (1-2C)alkyl; and
  $R_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl;
$R_{12}$ is selected from hydrogen, (1-6C)alkyl, (1-6C)alkoxy, (3-6C)cycloalkyl, (3-6C)cycloalkyl-(1-2C)alkyl, aryl, aryl-(1-2C)alkyl, heterocyclyl, heterocyclyl-(1-2C)alkyl, heteroaryl, heteroaryl-(1-2C)alkyl, and wherein $R_{12}$ is optionally further substituted by one or more substituents selected from hydroxy, fluoro, chloro, cyano, $CF_3$, $OCF_3$ (1-2C)alkyl or (1-2C)alkoxy;
$R_{13}$ is selected from hydrogen, (1-6C)alkyl, (1-6C)alkoxy, (3-6C)cycloalkyl, (3-6C)cycloalkyl-(1-2C)alkyl, aryl, aryl-(1-2C)alkyl, heteroaryl, heteroaryl-(1-2C)alkyl, and wherein $R_{13}$ is optionally further substituted by one or more substituents selected from hydroxy, fluoro, chloro, cyano, $CF_3$, $OCF_3$ (1-2C)alkyl or (1-2C)alkoxy;
$R_{11}$ and $R_{14}$ are independently selected from hydrogen, (1-6C)alkyl, (3-6C)cycloalkyl, (3-6C)cycloalkyl-(1-2C)alkyl, and wherein $R_{11}$ and $R_{14}$ are optionally further substituted by one or more substituents selected from hydroxy, fluoro, chloro, cyano, $CF_3$, $OCF_3$, (1-2C)alkyl or (1-2C)alkoxy;
optionally subject to the proviso that:
  X can only be N when Y is N; and
  when X and Y are both N, $R_3$ is selected from H or fluoro and $R_2$ is not a $NR_{11}R_{12}$ group;
wherein formula IV is:

Formula I

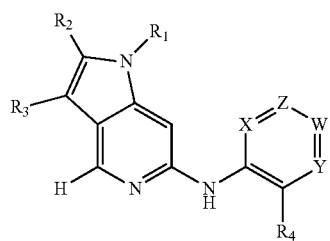

wherein:
  $R_1$ is hydrogen, (1-5C)alkyl, (1-5C)fluoroalkyl, (3-8C)cycloalkyl, (3-8C)cycloalkyl-(1-4C)alkyl, aryl, aryl-(1-4C)alkyl, heteroaryl, heteroaryl-(1-4C)alkyl, —S(O)$_2$—$R^a$,
  —C(O)—$R^a$, or —C(O)—O—$R^a$, wherein $R^a$ is (1-5C)alkyl, (3-8C)cycloalkyl, (3-8C)cycloalkyl-(1-4C)alkyl, aryl, aryl-(1-4C)alkyl, heteroaryl or heteroaryl-(1-4C)alkyl, and wherein any (1-5C)alkyl, (3-8C)cycloalkyl, (3-8C)cycloalkyl-(1-4C)alkyl, aryl, aryl-(1-4C)alkyl, heteroaryl, heteroaryl-(1-4C)alkyl group present in a $R_1$ substituent group is optionally substituted by methyl, trifluoromethyl, methoxy, trifluoromethoxy, halo, cyano, nitro, hydroxy, mercapto, amino, carboxy, carbamoyl, or sulphamoyl;
  $R_2$ is an aryl, aryl(1-2C)alkyl, 5- or 6-membered heteroaryl or a 5- or 6-membered heteroaryl(1-2C)alkyl, wherein $R_2$ is optionally substituted by one or more substituents selected from halogeno, trifluoromethyl, trifluoromethoxy, cyano, nitro, hydroxy, mercapto, amino, carboxy, carbamoyl, sulphamoyl,
  or a group of the formula:

L-L⁰-$R^b$ wherein
  L is absent or a linker group of the formula —[$CR_gR_h$]$_n$— in which n is an integer selected from 1, 2, 3 or 4, and $R_g$ and $R_h$ are each independently selected from hydrogen or (1-2C)alkyl;
  $L^0$ is absent or is selected from O, S, SO, $SO_2$, $N(R^c)$, C(O), C(O)O, OC(O), $CH(OR^c)$, $C(O)N(R^c)$, $N(R^c)C(O)$, $N(R^c)C(O)N(R^d)$, $SO_2N(R^c)$, or $N(R^c)SO_2$, wherein $R^c$ and $R^d$ are each independently selected from hydrogen or (1-2C)alkyl; and
  $R^b$ is (1-4C)alkyl, aryl, aryl-(1-4C)alkyl, (3-6C)cycloalkyl, (3-6C)cycloalkyl-(1-4C)alkyl, heteroaryl, heteroaryl-(1-4C)alkyl, heterocyclyl, or heterocyclyl-(1-4C)alkyl;
  and wherein $R^b$ is optionally further substituted by one or more substituents independently selected from oxo, halogeno, cyano, nitro, hydroxy, $NR^eR^f$, (1-5C)alkyl, (1-5C)alkoxy, (1-5C)alkanoyl, (1-5C)sulphonyl or aryl; and wherein $R^e$ and $R^f$ are each independently selected from hydrogen or (1-4C)alkyl or (3-6C)cycloalkyl-(1-4C)alkyl; or $R^e$ and $R^f$ can be linked such that, together with the nitrogen atom to which they are attached, they form a 4-7 membered heterocyclic, heteroaryl or carbocyclic ring;
  $R_3$ is H, (1-3C)alkyl, halogeno or $CF_3$;
  $R_4$ is cyano, (1-3C)alkyl, (1-3C)fluoroalkyl, (1-3C)alkoxy, (1-3C)perfluoroalkoxy, halo, (1-3C)alkanoyl, $C(O)NR^iR^j$, or $S(O)_2NR^iR^j$; wherein $R^i$ and $R^j$ are each independently selected from H or (1-3C)alkyl;
  X is CH or $CR_5$;
  W, Y and Z are each independently selected from N, CH, or $CR_5$;
  $R_5$ is halogeno, trifluoromethyl, trifluoromethoxy, cyano, nitro, hydroxy, mercapto, amino, carboxy, carbamoyl, sulphamoyl, ureido, (1-6C)alkyl, (2-6C)alkenyl, (2-6C)alkynyl,
  or $R_5$ is a group of the formula:

-L¹-L²-$R_7$ wherein
  $L^1$ is absent or a linker group of the formula [$CR_8R_9$]$_n$— in which n is an integer selected from 1, 2, 3 or 4, and $R_8$ and $R_9$ are each independently selected from hydrogen or (1-2C)alkyl;

$L^2$ is absent or is selected from O, S, SO, $SO_2$, $N(R_{10})$, C(O), C(O)O, OC(O), $CH(OR_{10})$, C(O)N $(R_{10})$, $N(R_{10})$C(O), $N(R_{10})$C(O)$N(R_{11})$, $S(O)_2N$ $(R_{10})$, or $N(R_{13})SO_2$, wherein $R_{10}$ and $R_{11}$ are each independently selected from hydrogen or (1-2C)alkyl; and $R_7$ is (1-6C)alkyl, aryl, aryl-(1-6C)alkyl, (3-6C)cycloalkyl, (3-6C)cycloalkyl-(1-6C)alkyl, heteroaryl, heteroaryl-(1-6C)alkyl, heterocyclyl, heterocyclyl-(1-6C)alkyl, and wherein $R_7$ is optionally further substituted by one or more substituents independently selected from hydrogen, oxo, halogeno, cyano, nitro, hydroxy, $NR_{12}R_{13}$, (1-4C)alkoxy, (1-5C)alkyl, (3-8C)cycloalkyl, (3-8C)cycloalkyl-(1-5C)alkyl, aryl, aryl-(1-5C)alkyl, (1-5C)alkanoyl, (1-5C)alkylsulphonyl, heterocyclyl, heterocyclyl-(1-5C) alkyl, heteroaryl, heteroaryl-(1-5C)alkyl, $CONR_{12}R_{13}$ and $SO_2NR_{12}R_{13}$;

$R_{12}$ and $R_{13}$ are each independently selected from hydrogen or (1-2C)alkyl; or $R_{12}$ and $R_{13}$ can be linked such that, together with the nitrogen atom to which they are attached, they form a 4-7 membered heterocyclic or heteroaryl ring;

or either W and Z, W and Y or Z and X are both $CR_5$ and the $R_5$ groups on the adjacent carbon atoms are linked such that, together with the carbon atoms to which they are attached, they form a fused 4-7 membered heterocyclic, heteroaryl or carbocyclic ring.

In one embodiment of each of the aspects and embodiment herein, the MPS1 inhibitor is selected from the group consisting of NMS-P715, S 81694 (NMS-P153), AZ3146, BAY 1217389, BAY 1161909, MPS1-IN-3, MPS1-IN-2 and CFI-402257.

In one embodiment of each of the aspects and embodiments herein, the MPS1 inhibitor is selected from the group consisting of NMS-P715, BAY 1217389 and BAY 1161909.

In one embodiment of each of the aspects and embodiments herein, the MPS1 inhibitor is selected from the group consisting of NMS-P715, S 81694 (NMS-P153), AZ3146, BAY 1217389, BAY 1161909, CFI-402257, CCT289346, a compound of formula I, a compound of formula II, a compound of formula III and a compound of formula IV, or a pharmaceutically acceptable salt or solvate thereof.

In one embodiment of each of the aspects and embodiment herein, the MPS1 inhibitor is selected from the group consisting of NMS-P715, AZ3146, BAY 1217389, BAY 1161909, CFI-402257, CCT289346, a compound of formula I, a compound of formula II, a compound of formula III and a compound of formula IV, or a pharmaceutically acceptable salt or solvate thereof.

In one embodiment of each of the aspects and embodiments herein, the MPS1 inhibitor is selected from the group consisting of NMS-P715, BAY 1217389, BAY 1161909, CCT289346, a compound of formula I, a compound of formula II, a compound of formula III and a compound of formula IV, or pharmaceutically acceptable salts or solvates thereof.

In one embodiment of each of the aspects and embodiments herein, the MPS1 inhibitor is not selected from the group consisting of a compound of formula I, a compound of formula II, a compound of formula III and a compound of formula IV, or pharmaceutically acceptable salts or solvates thereof.

In one embodiment of each of the aspects and embodiments herein, the MPS1 inhibitor is selected from the group consisting of a compound of formula I, a compound of formula II, a compound of formula III and a compound of formula IV, or pharmaceutically acceptable salts or solvates thereof.

In one embodiment of each of the aspects and embodiments herein, the MPS1 inhibitor is selected from the group consisting of NMS-P715, BAY 1217389, BAY 1161909 and CCT289346.

In one embodiment of each of the aspects and embodiments herein, the MPS1 inhibitor is selected from the group consisting of a compound of formula I or a compound of formula II, or pharmaceutically acceptable salts or solvates thereof.

In one embodiment of each of the aspects and embodiments herein, the MPS1 inhibitor is selected from a compound of formula V, or pharmaceutically acceptable salts thereof:

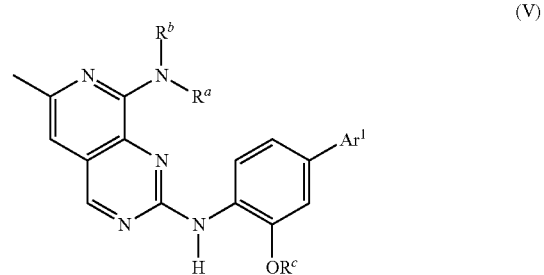

(V)

wherein $R^a$ is hydrogen;

$R^b$ is $C_{1-6}$ alkyl, optionally substituted with halogen; or $R^a$ and $R^b$ together with the nitrogen to which they are attached from a 4 to 10 membered heterocyclic ring optionally substituted by one or more groups selected from hydrogen, $C_{1-6}$ alkyl, CN, $C_{1-6}$ haloalkyl and O—$C_{1-6}$ haloalkyl;

$R^c$ is $C_{1-3}$ alkyl; and $Ar^1$ is a 5- or 6-membered heteroaryl ring optionally substituted with one or more substituents independently selected from $C_{1-6}$ alkyl, O—$C_{1-6}$ alkyl, CN, $C_{1-6}$ haloalkyl and O—$C_{1-6}$ haloalkyl.

In one embodiment of formula V, $R^b$ is $C_{1-6}$ alkyl, suitably $C_5$ and $C_6$ alkyl.

In another embodiment of formula V, $R^a$ and $R^b$ together with the nitrogen to which they are attached form an azetidinyl group which may optionally be substituted with one or more groups selected from $C_{1-6}$ alkyl, CN, $C_{1-6}$ haloalkyl and O—$C_{1-6}$ haloalkyl, or linked through a spiro carbon atom to a further 4-, 5- or 6-membered carbocyclic or heterocyclic ring to form a spiro bicyclic ring system, which may optionally be substituted with one or more groups selected from hydrogen, $C_{1-6}$ alkyl, CN, $C_{1-6}$ haloalkyl and O—$C_{1-6}$ haloalkyl.

In one embodiment of formula V, $R^c$ is selected from methyl and ethyl, suitably ethyl.

In one embodiment of formula V, $Ar^1$ is a 5-membered heteraryl group, suitably 1,2,4-triazole, optionally substituted with one or more substituents independently selected from $C_{1-6}$ alkyl, CN, $C_{1-6}$ haloalkyl and O—$C_{1-6}$ haloalkyl.

In one embodiment of formula V, $Ar^1$ is a 1,2,4-triazole, substituted with one or more $C_{1-3}$ alkyl substituents, suitably methyl.

In one embodiment of each of the aspects and embodiments herein, the MPS1 inhibitor is selected from NMS-P715, BAY 1217389, BAY 1161909 and a compound of formula V, or pharmaceutically acceptable salts thereof.

In one embodiment of each of the aspects and embodiments herein, the MPS1 inhibitor is selected from NMS-P715, BAY 1217389, BAY 1161909 and 5-(furan-2-yl)-N-(4-methoxyphenyl)isoquinolin-3-amine;
N-(4-methoxyphenyl)-5-(1-methyl-1H-pyrazol-4-yl)isoquinolin-3-amine;
N-(2-methoxy-4-((1-methylpiperidin-4-yl)oxy)phenyl)-5-(1-methyl-1H-pyrazol-4-yl)isoquinolin-3-amine;
N-(2,4-dimethoxyphenyl)-5-(1-methyl-1H-pyrazol-4-yl)isoquinolin-3-amine;
3-chloro-N,N-dimethyl-4-((5-(1-methyl-1H-pyrazol-4-yl)isoquinolin-3-yl)amino)benzamide;
3-methoxy-N,N-dimethyl-4-((5-(1-methyl-1H-pyrazol-4-yl)isoquinolin-3-yl)amino)benzamide;
(3-methoxy-4-((5-(1-methyl-1H-pyrazol-4-yl)isoquinolin-3-yl)amino)phenyl)(3-methoxyazetidin-1-yl)methanone;
N-(2-chloro-4-(1-methyl-1H-pyrazol-4-yl)phenyl)-5-(1-methyl-1H-pyrazol-4-yl)isoquinolin-3-amine;
(3-chloro-4-((5-(1-methyl-1H-pyrazol-4-yl)isoquinolin-3-yl)amino)phenyl)(3-methoxyazetidin-1-yl)methanone;
(3-methoxy-4-((5-(pyridin-3-yl)isoquinolin-3-yl)amino)phenyl)(3-methoxyazetidin-1-yl)methanone;
N-(4-(3,5-dimethylisoxazol-4-yl)-2-methoxyphenyl)-5-(1-methyl-1H-pyrazol-4-yl)isoquinolin-3-amine;
(3-methoxy-4-((8-(1-methyl-1H-pyrazol-4-yl)pyrido[3,4-d]pyrimidin-2-yl)amino)phenyl)(3-methoxyazetidin-1-yl)methanone;
N-(2-methoxy-4-(1-methyl-1H-pyrazol-4-yl)phenyl)-8-(1-methyl-1H-pyrazol-4-yl)pyrido[3,4-d]pyrimidin-2-amine;
N-(2-chloro-4-(1-methyl-1H-pyrazol-4-yl)phenyl)-8-(1-methyl-1H-pyrazol-4-yl)pyrido[3,4-d]pyrimidin-2-amine;
N-(2-chloro-4-(1-methyl-1H-imidazol-5-yl)phenyl)-5-(1-methyl-1H-pyrazol-4-yl)isoquinolin-3-amine;
N-(2-methoxy-4-(1-methyl-1H-pyrazol-4-yl)phenyl)-5-(1-methyl-1H-pyrazol-4-yl)isoquinolin-3-amine;
(3-methoxy-4-((5-(pyrimidin-5-yl)isoquinolin-3-yl)amino)phenyl)(3-methoxyazetidin-1-yl)methanone;
N-(2-methoxy-4-(1-methyl-1H-imidazol-5-yl)phenyl)-5-(1-methyl-1H-pyrazol-4-yl)isoquinolin-3-amine;
(4-((5-(1,5-dimethyl-1H-pyrazol-4-yl)isoquinolin-3-yl)amino)-3-methoxyphenyl)(3-methoxyazetidin-1-yl)methanone;
(3-methoxy-4-((5-(1-methyl-1H-pyrazol-3-yl)isoquinolin-3-yl)amino)phenyl)(3-methoxyazetidin-1-yl)methanone;
N-(2-chloro-4-(1,2-dimethyl-1H-imidazol-5-yl)phenyl)-5-(1-methyl-1H-pyrazol-4-yl)isoquinolin-3-amine;
N-(4-(1,2-dimethyl-1H-imidazol-5-yl)-2-methoxyphenyl)-5-(1-methyl-1H-pyrazol-4-yl)isoquinolin-3-amine;
N-(2-methoxy-4-(1-methyl-1H-pyrazol-4-yl)phenyl)-8-phenylpyrido[3,4-d]pyrimidin-2-amine;
8-cyclopropyl-N-(2-methoxy-4-(1-methyl-1H-pyrazol-4-yl)phenyl)pyrido[3,4-d]pyrimidin-2-amine;
N-(2-methoxy-5-methyl-4-(1-methyl-1H-pyrazol-4-yl)phenyl)-8-(1-methyl-1H-pyrazol-4-yl)pyrido[3,4-d]pyrimidin-2-amine;
(3-methoxy-4-((5-(1-methyl-1H-pyrazol-5-yl)isoquinolin-3-yl)amino)phenyl)(3-methoxyazetidin-1-yl)methanone;
(4-((5-(1,3-dimethyl-1H-pyrazol-4-yl)isoquinolin-3-yl)amino)-3-methoxyphenyl)(3-methoxyazetidin-1-yl)methanone;
(4-((5-(1-isopropyl-1H-pyrazol-4-yl)isoquinolin-3-yl)amino)-3-methoxyphenyl)(3-methoxyazetidin-1-yl)methanone;
4-((5-(1-methyl-1H-pyrazol-4-yl)isoquinolin-3-yl)amino)-N-(1-methylpiperidin-4-yl)-3-(trifluoromethoxy)benzamide;
(4-((5-(3,5-dimethylisoxazol-4-yl)isoquinolin-3-yl)amino)-3-methoxyphenyl)(3-methoxyazetidin-1-yl)methanone;
(3-methoxy-4-((5-(1-methyl-1H-imidazol-5-yl)isoquinolin-3-yl)amino)phenyl)(3-methoxyazetidin-1-yl)methanone;
N-(2-methoxy-4-(1-methyl-1H-pyrazol-4-yl)phenyl)-8-(pyrrolidin-1-yl)pyrido[3,4-d]pyrimidin-2-amine;
N-(4-(1,2-dimethyl-1H-imidazol-5-yl)-2-methoxyphenyl)-8-(1-methyl-1H-pyrazol-4-yl)pyrido[3,4-d]pyrimidin-2-amine;
tert-butyl 4-(4-(3-((2-methoxy-4-(3-methoxyazetidine-1-carbonyl)phenyl)amino)isoquinolin-5-yl)-1H-pyrazol-1-yl)piperidine-1-carboxylate;
(3-methoxy-4-((5-(1-(piperidin-4-yl)-1H-pyrazol-4-yl)isoquinolin-3-yl)amino)phenyl)(3-methoxyazetidin-1-yl)methanone;
(3-methoxy-4-((5-(1-(1-methylpiperidin-4-yl)-1H-pyrazol-4-yl)isoquinolin-3-yl)amino)phenyl)(3-methoxyazetidin-1-yl)methanone;
(3-methoxy-4-((5-(1-(2-methoxyethyl)-1H-pyrazol-4-yl)isoquinolin-3-yl)amino)phenyl)(3-methoxyazetidin-1-yl)methanone;
N8,N8-diethyl-N2-(2-methoxy-4-(1-methyl-1H-pyrazol-4-yl)phenyl)pyrido[3,4-d]pyrimidine-2,8-diamine;
N8-cyclopentyl-N2-(2-methoxy-4-(1-methyl-1H-pyrazol-4-yl)phenyl)pyrido[3,4-d]pyrimidine-2,8-diamine;
(4-((5-(1-(2-(dimethylamino)ethyl)-1H-pyrazol-4-yl)isoquinolin-3-yl)amino)-3-methoxyphenyl)(3-methoxyazetidin-1-yl)methanone;
N-(2-methoxy-4-(1-methyl-1H-pyrazol-4-yl)phenyl)-5-(1-methyl-1H-pyrazol-4-yl)-2,6-naphthyridin-3-amine;
N-(2-methoxy-4-(1-methyl-1H-pyrazol-4-yl)phenyl)-8-(piperidin-1-yl)pyrido[3,4-d]pyrimidin-2-amine;
N8-cyclohexyl-N2-(2-methoxy-4-(1-methyl-1H-pyrazol-4-yl)phenyl)pyrido[3,4-d]pyrimidine-2,8-diamine;
N-(2-methoxy-4-(1-methyl-1H-pyrazol-4-yl)phenyl)-8-(3-methylpyrrolidin-1-yl)pyrido[3,4-d]pyrimidin-2-amine;
8-(3,3-difluoropyrrolidin-1-yl)-N-(2-methoxy-4-(1-methyl-1H-pyrazol-4-yl)phenyl)pyrido[3,4-d]pyrimidin-2-amine;
N-(4-(1,2-dimethyl-1H-imidazol-5-yl)-2-methoxyphenyl)-5-(1-methyl-1H-pyrazol-4-yl)-2,6-naphthyridin-3-amine;
N8-(cyclopropylmethyl)-N2-(2-methoxy-4-(1-methyl-1H-pyrazol-4-yl)phenyl)pyrido[3,4-d]pyrimidine-2,8-diamine;
8-(1-methyl-1H-pyrazol-4-yl)-N-(2-methyl-4-(1-methyl-1H-pyrazol-4-yl)phenyl)pyrido[3,4-d]pyrimidin-2-amine;
N8-cyclopentyl-N2-(2-methoxy-4-(1-methyl-1H-pyrazol-4-yl)phenyl)-N8-methylpyrido[3,4-d]pyrimidine-2,8-diamine;
N-(2-ethoxy-4-(1-methyl-1H-pyrazol-4-yl)phenyl)-8-(1-methyl-1H-pyrazol-4-yl)pyrido[3,4-d]pyrimidin-2-amine;
N-(2-isopropoxy-4-(1-methyl-1H-pyrazol-4-yl)phenyl)-8-(1-methyl-1H-pyrazol-4-yl)pyrido[3,4-d]pyrimidin-2-amine;
N-(2-(2-methoxyethoxy)-4-(1-methyl-1H-pyrazol-4-yl)phenyl)-8-(1-methyl-1H-pyrazol-4-yl)pyrido[3,4-d]pyrimidin-2-amine;
N8-isopentyl-N2-(2-methoxy-4-(1-methyl-1H-pyrazol-4-yl)phenyl)pyrido[3,4-d]pyrimidine-2,8-diamine;

N-(2-methoxy-4-(1-methyl-1H-pyrazol-4-yl)phenyl)-8-morpholinopyrido[3,4-d]pyrimidin-2-amine;

N-(2-methoxy-4-(1-methyl-1H-pyrazol-4-yl)phenyl)-8-(4-methylpiperazin-1-yl)pyrido[3,4-d]pyrimidin-2-amine;

8-(3,3-difluoroazetidin-1-yl)-N-(2-methoxy-4-(1-methyl-1H-pyrazol-4-yl)phenyl)pyrido[3,4-d]pyrimidin-2-amine;

N-(2-methoxy-4-(1-methyl-1H-pyrazol-4-yl)phenyl)-8-(2-methylpyrrolidin-1-yl)pyrido[3,4-d]pyrimidin-2-amine;

N8-isobutyl-N2-(2-methoxy-4-(1-methyl-1H-pyrazol-4-yl)phenyl)pyrido[3,4-d]pyrimidine-2,8-diamine;

8-(cyclohexylthio)-N-(2-methoxy-4-(1-methyl-1H-pyrazol-4-yl)phenyl)pyrido[3,4-d]pyrimidin-2-amine;

N-(2-methoxy-4-(1-methyl-1H-pyrazol-4-yl)phenyl)-8-(6-azaspiro[3.4]octan-6-yl)pyrido[3,4-d]pyrimidin-2-amine;

N8-cyclohexyl-N2-(2-methoxy-4-(1-(2-(4-methylpiperazin-1-yl)ethyl)-1H-pyrazol-4-yl)phenyl)pyrido[3,4-d]pyrimidine-2,8-diamine;

8-(1-ethyl-1H-pyrazol-4-yl)-N-(2-methoxy-4-(1-methyl-1H-pyrazol-4-yl)phenyl)pyrido[3,4-d]pyrimidin-2-amine;

8-(1-isopropyl-1H-pyrazol-4-yl)-N-(2-methoxy-4-(1-methyl-1H-pyrazol-4-yl)phenyl)pyrido[3,4-d]pyrimidin-2-amine;

N-(2-methoxy-4-(1-methyl-1H-pyrazol-4-yl)phenyl)-8-(3-methoxyazetidin-1-yl)pyrido[3,4-d]pyrimidin-2-amine;

N1-(cyclopropylmethyl)-N7-(2-methoxy-4-(1-methyl-1H-pyrazol-4-yl)phenyl)-2,6-naphthyridine-1,7-diamine;

N1-cyclohexyl-N7-(2-methoxy-4-(1-methyl-1H-pyrazol-4-yl)phenyl)-2,6-naphthyridine-1,7-diamine;

N8-cyclohexyl-N2-(4-(1-(2-(dimethylamino)ethyl)-1H-pyrazol-4-yl)-2-methoxyphenyl)pyrido[3,4-d]pyrimidine-2,8-diamine;

N2-(2-methoxy-4-(1-methyl-1H-pyrazol-4-yl)phenyl)-N8-neopentylpyrido[3,4-d]pyrimidine-2,8-diamine;

N2-(2-methoxy-4-(1-methyl-1H-pyrazol-4-yl)phenyl)-N8-(tetrahydro-2H-pyran-4-yl)pyrido[3,4-d]pyrimidine-2,8-diamine;

N8-(cyclopropylmethyl)-N2-(2-methyl-4-(1-methyl-1H-pyrazol-4-yl)phenyl)pyrido[3,4-d]pyrimidine-2,8-diamine;

N8-cyclohexyl-N2-(2-methyl-4-(1-methyl-1H-pyrazol-4-yl)phenyl)pyrido[3,4-d]pyrimidine-2,8-diamine;

N8-(cyclopropylmethyl)-N2-(2-ethoxy-4-(1-methyl-1H-pyrazol-4-yl)phenyl)pyrido[3,4-d]pyrimidine-2,8-diamine;

N8-(cyclohexylmethyl)-N2-(2-methoxy-4-(1-methyl-1H-pyrazol-4-yl)phenyl)pyrido[3,4-d]pyrimidine-2,8-diamine;

2-(4-(4-((8-(cyclohexylamino)pyrido[3,4-d]pyrimidin-2-yl)amino)-3-methoxyphenyl)-1H-pyrazol-1-yl)ethanol;

8-(cyclopropylmethoxy)-N-(2-methoxy-4-(1-methyl-1H-pyrazol-4-yl)phenyl)pyrido[3,4-d]pyrimidin-2-amine;

1-((2-((2-methoxy-4-(1-methyl-1H-pyrazol-4-yl)phenyl)amino)pyrido[3,4-d]pyrimidin-8-yl)amino)-2-methylpropan-2-ol;

N2-(2-methoxy-4-(1-methyl-1H-pyrazol-4-yl)phenyl)-N8-(oxetan-3-ylmethyl)pyrido[3,4-d]pyrimidine-2,8-diamine;

N8-(3,3-dimethylbutan-2-yl)-N2-(2-methoxy-4-(1-methyl-1H-pyrazol-4-yl)phenyl)pyrido[3,4-d]pyrimidine-2,8-diamine;

3-((2-((2-methoxy-4-(1-methyl-1H-pyrazol-4-yl)phenyl)amino)pyrido[3,4-d]pyrimidin-8-yl)amino)-2,2-dimethylpropan-1-ol;

N2-(2-ethoxy-4-(1-methyl-1H-pyrazol-4-yl)phenyl)-N8-(tetrahydro-2H-pyran-4-yl)pyrido[3,4-d]pyrimidine-2,8-diamine;

N2-(2-methoxy-6-morpholinopyridin-3-yl)-N8-neopentylpyrido[3,4-d]pyrimidine-2,8-diamine;

N2-(2-methoxy-6-(methylsulfonyl)pyridin-3-yl)-N8-neopentylpyrido[3,4-d]pyrimidine-2,8-diamine;

N2-(2-methoxy-4-(1-methyl-1H-imidazol-5-yl)phenyl)-N8-neopentylpyrido[3,4-d]pyrimidine-2,8-diamine;

N2-(4-(1,3-dimethyl-1H-pyrazol-4-yl)-2-methoxyphenyl)-N8-neopentylpyrido[3,4-d]pyrimidine-2,8-diamine;

N8-(1-cyclopropylethyl)-N2-(2-methoxy-4-(1-methyl-1H-pyrazol-4-yl)phenyl)pyrido[3,4-d]pyrimidine-2,8-diamine;

2-(4-(3-methoxy-4-((8-((tetrahydro-2H-pyran-4-yl)amino)pyrido[3,4-d]pyrimidin-2-yl)amino)phenyl)-1H-pyrazol-1-yl)ethanol;

N2-(4-(1,5-dimethyl-1H-pyrazol-4-yl)-2-methoxyphenyl)-N8-neopentylpyrido[3,4-d]pyrimidine-2,8-diamine;

(R)—N8-(3,3-dimethylbutan-2-yl)-N2-(2-methoxy-4-(1-methyl-1H-pyrazol-4-yl)phenyl)pyrido[3,4-d]pyrimidine-2,8-diamine;

(S)—N8-(3,3-dimethylbutan-2-yl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(tetrahydrofuran-3-yl)pyrido[3,4-d]pyrimidine-2,8-diamine;

N2-(2-methoxy-4-(1-methyl-1H-pyrazol-4-yl)phenyl)-N8-((tetrahydrofuran-3-yl)methyl)pyrido[3,4-d]pyrimidine-2,8-diamine;

1-(2-((2-methoxy-4-(1-methyl-1H-pyrazol-4-yl)phenyl)amino)pyrido[3,4-d]pyrimidin-8-yl)pyrrolidin-3-ol;

N2-(2-methoxy-4-(1-methyl-1H-pyrazol-4-yl)phenyl)-N8-methyl-N8-(tetrahydro-2H-pyran-4-yl)pyrido[3,4-d]pyrimidine-2,8-diamine;

N8-(tert-butyl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(1-methylcyclohexyl)pyrido[3,4-d]pyrimidine-2,8-diamine;

8-(1-(2,2-difluoroethyl)-1H-pyrazol-4-yl)-N-(2-methoxy-4-(1-methyl-1H-pyrazol-4-yl)phenyl)pyrido[3,4-d]pyrimidin-2-amine;

N2-(4-(1,2-dimethyl-1H-imidazol-5-yl)-2-methoxyphenyl)-N8-neopentylpyrido[3,4-d]pyrimidine-2,8-diamine;

N2-(2-methoxy-4-(1-methyl-1H-pyrazol-4-yl)phenyl)-6-methyl-N8-neopentylpyrido[3,4-d]pyrimidine-2,8-diamine;

N2-(2-methoxy-4-morpholinophenyl)-N8-neopentylpyrido[3,4-d]pyrimidine-2,8-diamine;

N8-(2,2-difluoropropyl)-N2-(2-methoxy-4-(1-methyl-1H-pyrazol-4-yl)phenyl)pyrido[3,4-d]pyrimidine-2,8-diamine;

N8-(3-methoxy-2,2-dimethylpropyl)-N2-(2-methoxy-4-(1-methyl-1H-pyrazol-4-yl)phenyl)pyrido[3,4-d]pyrimidine-2,8-diamine;

N8-(2-methoxy-2-methylpropyl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(2,2,2-trifluoroethyl)pyrido[3,4-d]pyrimidine-2,8-diamine;

N-(2-methoxy-4-(1-methyl-1H-pyrazol-4-yl)phenyl)-8-(2-oxa-6-azaspiro[3.4]octan-6-yl)pyrido[3,4-d]pyrimidin-2-amine;

1-(((2-((2-methoxy-4-(1-methyl-1H-pyrazol-4-yl)phenyl)
amino)pyrido[3,4-d]pyrimidin-8-yl)amino)methyl)cyclobutanol;

8-chloro-N-(2-methoxy-4-(1-methyl-1H-pyrazol-4-yl)phenyl)pyrido[3,4-d]pyrimidin-2-amine;

N2-(2-ethyl-4-(1-methyl-1H-pyrazol-4-yl)phenyl)-N8-neopentylpyrido[3,4-d]pyrimidine-2,8-diamine;

N2-(4-(1-methyl-1H-pyrazol-4-yl)-2-(trifluoromethoxy)phenyl)-N8-neopentylpyrido[3,4-d]pyrimidine-2,8-diamine;

N2-(2-methoxy-4-(1-methyl-1H-pyrazol-4-yl)phenyl)-N8-methylpyrido[3,4-d]pyrimidine-2,8-diamine;

N2-(2-methoxy-4-(1-methyl-1H-pyrazol-4-yl)phenyl)-N8,N8-dimethylpyrido[3,4-d]pyrimidine-2,8-diamine;

N-(2-((2-methoxy-4-(1-methyl-1H-pyrazol-4-yl)phenyl)amino)pyrido[3,4-d]pyrimidin-8-yl)-2-methylpropane-2-sulfinamide;

N2-(2-methoxy-4-(4-morpholinopiperidin-1-yl)phenyl)-N8-neopentylpyrido[3,4-d]pyrimidine-2,8-diamine;

N2-(2-methoxy-4-(1-methyl-1H-pyrazol-4-yl)phenyl)-N8-((3-methyloxetan-3-yl)methyl)pyrido[3,4-d]pyrimidine-2,8-diamine;

N2-(2-methoxy-4-(piperidin-1-yl)phenyl)-N8-neopentylpyrido[3,4-d]pyrimidine-2,8-diamine;

N-(2-((2-methoxy-4-(1-methyl-1H-pyrazol-4-yl)phenyl)amino)pyrido[3,4-d]pyrimidin-8-yl)-2-methylpropane-2-sulfonamide;

N2-(2-methoxy-4-(1-methyl-1H-pyrazol-4-yl)phenyl)-N8-(oxetan-3-yl)pyrido[3,4-d]pyrimidine-2,8-diamine;

(1-(3-methoxy-4-((8-(neopentylamino)pyrido[3,4-d]pyrimidin-2-yl)amino)phenyl)piperidin-4-yl)(morpholino)methanone;

N2-(2-methoxy-4-(4-methylpiperazin-1-yl)phenyl)-N8-neopentylpyrido[3,4-d]pyrimidine-2,8-diamine;

1-(((2-((2-methoxy-4-(1-methyl-1H-pyrazol-4-yl)phenyl)amino)pyrido[3,4-d]pyrimidin-8-yl)amino)methyl)cyclopropanol;

N2-(2-methoxy-4-(1-methyl-1H-pyrazol-4-yl)phenyl)-N8-(1-methylpiperidin-4-yl)pyrido[3,4-d]pyrimidine-2,8-diamine;

2-((2-((2-methoxy-4-(1-methyl-1H-pyrazol-4-yl)phenyl)amino)pyrido[3,4-d]pyrimidin-8-yl)amino)-2-methylpropan-1-ol;

N-(2-methoxy-4-(1-methyl-1H-pyrazol-4-yl)phenyl)-8-(2-oxa-6-azaspiro[3.3]heptan-6-yl)pyrido[3,4-d]pyrimidin-2-amine;

N2-(2-methoxy-4-(1-methyl-1H-pyrazol-4-yl)phenyl)-N8-(oxetan-2-ylmethyl)pyrido[3,4-d]pyrimidine-2,8-diamine;

N2-(2-chloro-4-morpholinophenyl)-N8-neopentylpyrido[3,4-d]pyrimidine-2,8-diamine N2-(2-methoxy-4-(4-methyl-4H-1,2,4-triazol-3-yl)phenyl)-N8-neopentylpyrido[3,4-d]pyrimidine-2,8-diamine;

N2-(2-methoxy-4-(4-(methylsulfonyl)piperazin-1-yl)phenyl)-N8-neopentylpyrido[3,4-d]pyrimidine-2,8-diamine;

N2-(2-methoxy-4-(1-methyl-1H-pyrazol-4-yl)phenyl)-N8-((3-methyltetrahydrofuran-3-yl)methyl)pyrido[3,4-d]pyrimidine-2,8-diamine;

N-(4-(1,5-dimethyl-1H-pyrazol-4-yl)-2-methoxyphenyl)-8-(2-oxa-6-azaspiro[3.4]octan-6-yl)pyrido[3,4-d]pyrimidin-2-amine;

N2-(4-(1,5-dimethyl-1H-pyrazol-4-yl)-2-methoxyphenyl)-N8-((3-methyloxetan-3-yl)methyl)pyrido[3,4-d]pyrimidine-2,8-diamine;

N2-(4-(1,5-dimethyl-1H-pyrazol-4-yl)-2-methoxyphenyl)-N8-(2-methoxy-2-methylpropyl)pyrido[3,4-d]pyrimidine-2,8-diamine;

N2-(4-(1,2-dimethyl-1H-imidazol-5-yl)-2-methoxyphenyl)-N8-(2-methoxy-2-methylpropyl)-6-methylpyrido[3,4-d]pyrimidine-2,8-diamine;

N2-(4-(1,2-dimethyl-1H-imidazol-5-yl)-2-methoxyphenyl)-6-methyl-N8-neopentylpyrido[3,4-d]pyrimidine-2,8-diamine;

N2-(2-methoxy-4-(4-methyl-4H-1,2,4-triazol-3-yl)phenyl)-6-methyl-N8-neopentylpyrido[3,4-d]pyrimidine-2,8-diamine;

N-(2-ethoxy-4-(1-methyl-1H-pyrazol-4-yl)phenyl)-8-(2-oxa-6-azaspiro[3.4]octan-6-yl)pyrido[3,4-d]pyrimidin-2-amine;

2-((2-((2-methoxy-4-(1-methyl-1H-pyrazol-4-yl)phenyl)amino)pyrido[3,4-d]pyrimidin-8-yl)amino)ethanol;

N2-(2-methoxy-4-(1-methyl-1H-pyrazol-4-yl)phenyl)-N8-(2-methoxyethyl)pyrido[3,4-d]pyrimidine-2,8-diamine;

1-((2-((2-methoxy-4-(1-methyl-1H-pyrazol-4-yl)phenyl)amino)pyrido[3,4-d]pyrimidin-8-yl)amino)propan-2-ol;

2-((2-((2-methoxy-4-(1-methyl-1H-pyrazol-4-yl)phenyl)amino)pyrido[3,4-d]pyrimidin-8-yl)amino)propan-1-ol;

N2-(4-(1,5-dimethyl-1H-pyrazol-4-yl)-2-methoxyphenyl)-N8-((3-methyltetrahydrofuran-3-yl)methyl)pyrido[3,4-d]pyrimidine-2,8-diamine;

4-(2-((2-methoxy-4-(1-methyl-1H-pyrazol-4-yl)phenyl)amino)pyrido[3,4-d]pyrimidin-8-yl)thiomorpholine 1,1-dioxide;

N-(2-methoxy-4-(1-methyl-1H-pyrazol-4-yl)phenyl)-8-(7-oxa-2-azaspiro[3.5]nonan-2-yl)pyrido[3,4-d]pyrimidin-2-amine;

N2-(2-methoxy-4-(1-methyl-1H-pyrazol-4-yl)phenyl)-5-methyl-N8-neopentylpyrido[3,4-d]pyrimidine-2,8-diamine;

N-(2-methoxy-4-(1-methyl-1H-pyrazol-4-yl)phenyl)-8-(6-oxa-2-azaspiro[3.4]octan-2-yl)pyrido[3,4-d]pyrimidin-2-amine;

1-(2-((2-methoxy-4-(1-methyl-1H-pyrazol-4-yl)phenyl)amino)pyrido[3,4-d]pyrimidin-8-yl)azetidine-3-carbonitrile;

N-(2-methoxy-4-(1-methyl-1H-pyrazol-4-yl)phenyl)-8-(2-oxa-7-azaspiro[4.4]nonan-7-yl)pyrido[3,4-d]pyrimidin-2-amine;

N-(2-methoxy-4-(1-methyl-1H-pyrazol-4-yl)phenyl)-8-(2-oxa-6-azaspiro[3.5]nonan-6-yl)pyrido[3,4-d]pyrimidin-2-amine;

N8-((3-fluorooxetan-3-yl)methyl)-N2-(2-methoxy-4-(1-methyl-1H-pyrazol-4-yl)phenyl)pyrido[3,4-d]pyrimidine-2,8-diamine;

N-(4-chloro-2-methoxyphenyl)-8-(2-oxa-6-azaspiro[3.4]octan-6-yl)pyrido[3,4-d]pyrimidin-2-amine;

N-(2,4-dichlorophenyl)-8-(2-oxa-6-azaspiro[3.4]octan-6-yl)pyrido[3,4-d]pyrimidin-2-amine; 4-((8-(2-oxa-6-azaspiro[3.4]octan-6-yl)pyrido[3,4-d]pyrimidin-2-yl)amino)-3-methoxybenzonitrile;

N-(2-chloro-4-(methylsulfonyl)phenyl)-8-(2-oxa-6-azaspiro[3.4]octan-6-yl)pyrido[3,4-d]pyrimidin-2-amine;

N-(2-chloro-4-(pyrimidin-5-yl)phenyl)-8-(2-oxa-6-azaspiro[3.4]octan-6-yl)pyrido[3,4-d]pyrimidin-2-amine;

N-(2-chloro-4-(5-methyl-1,3,4-oxadiazol-2-yl)phenyl)-8-(2-oxa-6-azaspiro[3.4]octan-6-yl)pyrido[3,4-d]pyrimidin-2-amine;

N8-(2-methoxy-2-methylpropyl)-N2-(2-methoxy-4-(4-methyl-4H-1,2,4-triazol-3-yl)phenyl)-6-methylpyrido[3,4-d]pyrimidine-2,8-diamine;

6-cyclopropyl-N-(2-methoxy-4-(1-methyl-1H-pyrazol-4-yl)phenyl)-8-(2-oxa-6-azaspiro[3.4]octan-6-yl)pyrido[3,4-d]pyrimidin-2-amine;

2-((2-((2-methoxy-4-(1-methyl-1H-pyrazol-4-yl)phenyl)
   amino)pyrido[3,4-d]pyrimidin-8-yl)amino)propane-1,3-
   diol;
3-methoxy-2-((2-((2-methoxy-4-(1-methyl-1H-pyrazol-4-
   yl)phenyl)amino)pyrido[3,4-d]pyrimidin-8-yl)amino)
   propan-1-ol;
(3-(((2-((2-methoxy-4-(1-methyl-1H-pyrazol-4-yl)phenyl)
   amino)pyrido[3,4-d]pyrimidin-8-yl)amino)methyl)
   oxetan-3-yl)methanol;
(S)—N2-(2-methoxy-4-(1-methyl-1H-pyrazol-4-yl)phe-
   nyl)-N8-((3-methyltetrahydrofuran-3-yl)methyl)pyrido
   [3,4-d]pyrimidine-2,8-diamine;
(R)—N2-(2-methoxy-4-(1-methyl-1H-pyrazol-4-yl)phe-
   nyl)-N8-((3-methyltetrahydrofuran-3-yl)methyl)pyrido
   [3,4-d]pyrimidine-2,8-diamine;
N-(4-chloro-2-fluorophenyl)-8-(2-oxa-6-azaspiro[3.4]oc-
   tan-6-yl)pyrido[3,4-d]pyrimidin-2-amine;
4-((8-(2-oxa-6-azaspiro[3.4]octan-6-yl)pyrido[3,4-d]py-
   rimidin-2-yl)amino)-3-chlorobenzonitrile;
N2-(2-methoxy-4-(1-(2-methoxyethyl)-2-methyl-1H-imida-
   zol-5-yl)phenyl)-6-methyl-N8-neopentylpyrido[3,4-d]
   pyrimidine-2,8-diamine;
N2-(2-ethoxy-4-(4-methyl-4H-1,2,4-triazol-3-yl)phenyl)-6-
   methyl-N8-neopentylpyrido[3,4-d]pyrimidine-2,8-di-
   amine;
N2-(2-methoxy-4-(4-(methylsulfonyl)piperazin-1-yl)phe-
   nyl)-6-methyl-N8-neopentylpyrido[3,4-d]pyrimidine-2,
   8-diamine;
N-(2-methoxy-4-(1-methyl-1H-pyrazol-4-yl)phenyl)-8-
   (pyridin-4-yl)pyrido[3,4-d]pyrimidin-2-amine;
N8-(2-methoxy-2-methylpropyl)-N2-(2-methoxy-4-(4-
   methyl-4H-1,2,4-triazol-3-yl)phenyl)-5-methylpyrido[3,
   4-d]pyrimidine-2,8-diamine;
N2-(2-methoxy-4-(4-methyl-4H-1,2,4-triazol-3-yl)phenyl)-
   5-methyl-N8-neopentylpyrido[3,4-d]pyrimidine-2,8-di-
   amine;
N-(2-methoxy-4-(1-methyl-1H-pyrazol-4-yl)phenyl)-8-(2-
   methylmorpholino)pyrido[3,4-d]pyrimidin-2-amine;
(4-(3-methoxy-4-((8-((2-methoxy-2-methylpropyl)amino)
   pyrido[3,4-d]pyrimidin-2-yl)amino)phenyl)-1-methyl-
   1H-pyrazol-5-yl)methanol;
(4-(3-methoxy-4-((8-(((3-methyltetrahydrofuran-3-yl)
   methyl)amino)pyrido[3,4-d]pyrimidin-2-yl)amino)phe-
   nyl)-1-methyl-1H-pyrazol-5-yl)methanol;
N8-(2-methoxy-2-methylpropyl)-N2-(2-methoxy-4-(1-(2-
   methoxyethyl)-2-methyl-1H-imidazol-5-yl)phenyl)
   pyrido[3,4-d]pyrimidine-2,8-diamine;
N2-(2-methoxy-4-(1-(2-methoxyethyl)-2-methyl-1H-imida-
   zol-5-yl)phenyl)-N8-((3-methyltetrahydrofuran-3-yl)
   methyl)pyrido[3,4-d]pyrimidine-2,8-diamine;
N2-(2-ethoxy-4-(4-methyl-4H-1,2,4-triazol-3-yl)phenyl)-
   N8-(2-methoxy-2-methylpropyl)pyrido[3,4-d]pyrimi-
   dine-2,8-diamine;
N2-(2-ethoxy-4-(4-methyl-4H-1,2,4-triazol-3-yl)phenyl)-
   N8-((3-methyltetrahydrofuran-3-yl)methyl)pyrido[3,4-d]
   pyrimidine-2,8-diamine;
8-(3,6-dihydro-2H-pyran-4-yl)-N-(2-methoxy-4-(1-methyl-
   1H-pyrazol-4-yl)phenyl)pyrido[3,4-d]pyrimidin-2-
   amine;
N8-(2-methoxy-2-methylpropyl)-N2-(2-methoxy-6-(1-
   methyl-1H-tetrazol-5-yl)pyridin-3-yl)pyrido[3,4-d]py-
   rimidine-2,8-diamine;
N2-(6-(1,2-dimethyl-1H-imidazol-5-yl)-2-methoxypyridin-
   3-yl)-N8-(2-methoxy-2-methylpropyl)pyrido[3,4-d]py-
   rimidine-2,8-diamine;
N8-(2-methoxy-2-methylpropyl)-N2-(2-methoxy-4-(1-
   methyl-1H-tetrazol-5-yl)phenyl)pyrido[3,4-d]pyrimi-
   dine-2,8-diamine;
N-(2-methoxy-4-(1-methyl-1H-pyrazol-4-yl)phenyl)-8-(py-
   rimidin-5-yl)pyrido[3,4-d]pyrimidin-2-amine;
N2-(2-methoxy-4-(1-methyl-1H-pyrazol-4-yl)phenyl)-N8-
   (1-(tetrahydrofuran-3-yl)ethyl)pyrido[3,4-d]pyrimidine-
   2,8-diamine;
N2-(4-(1,3-dimethyl-1H-pyrazol-4-yl)-2-methoxyphenyl)-
   N8-(2-methoxy-2-methylpropyl)pyrido[3,4-d]pyrimi-
   dine-2,8-diamine;
N2-(4-(1,3-dimethyl-1H-pyrazol-4-yl)-2-methoxyphenyl)-
   N8-((3-methyltetrahydrofuran-3-yl)methyl)pyrido[3,4-d]
   pyrimidine-2,8-diamine;
N-(2-methoxy-4-(1-methyl-1H-pyrazol-4-yl)phenyl)-8-(4-
   methoxypiperidin-1-yl)pyrido[3,4-d]pyrimidin-2-amine;
1-(2-((2-methoxy-4-(1-methyl-1H-pyrazol-4-yl)phenyl)
   amino)pyrido[3,4-d]pyrimidin-8-yl)piperidine-4-carboni-
   trile;
N-(2-methoxy-4-(1-methyl-1H-pyrazol-4-yl)phenyl)-8-(4-
   (methylsulfonyl)piperazin-1-yl)pyrido[3,4-d]pyrimidin-
   2-amine;
N2-(4-(1,3-dimethyl-1H-pyrazol-4-yl)-2-methoxyphenyl)-
   N8-(2-methoxy-2-methylpropyl)-6-methylpyrido[3,4-d]
   pyrimidine-2,8-diamine;
N-(2-ethoxy-4-(4-methyl-4H-1,2,4-triazol-3-yl)phenyl)-6-
   methyl-8-(6-oxa-2-azaspiro[3.4]octan-2-yl)pyrido[3,4-d]
   pyrimidin-2-amine;
N2-(6-(1,3-dimethyl-1H-pyrazol-4-yl)-2-methoxypyridin-
   3-yl)-N8-(2-methoxy-2-methylpropyl)pyrido[3,4-d]py-
   rimidine-2,8-diamine;
N2-(6-(1,5-dimethyl-1H-pyrazol-4-yl)-2-methoxypyridin-
   3-yl)-N8-(2-methoxy-2-methylpropyl)pyrido[3,4-d]py-
   rimidine-2,8-diamine;
N8-(2-methoxy-2-methylpropyl)-N2-(2-methoxy-6-(1-
   methyl-1H-1,2,3-triazol-5-yl)pyridin-3-yl)pyrido[3,4-d]
   pyrimidine-2,8-diamine;
N8-(2-methoxy-2-methylpropyl)-N2-(2-methoxy-6-(2-
   methyl-2H-1,2,3-triazol-4-yl)pyridin-3-yl)pyrido[3,4-d]
   pyrimidine-2,8-diamine;
(3-methoxy-4-((8-((2-methoxy-2-methylpropyl)amino)
   pyrido[3,4-d]pyrimidin-2-yl)amino)phenyl)(3-
   methoxyazetidin-1-yl)methanone;
3-methoxy-4-((8-((2-methoxy-2-methylpropyl)amino)
   pyrido[3,4-d]pyrimidin-2-yl)amino)-N,N-dimethylbenz-
   amide;
(3-methoxy-4-((8-((2-methoxy-2-methylpropyl)amino)
   pyrido[3,4-d]pyrimidin-2-yl)amino)phenyl)(4-meth-
   ylpiperazin-1-yl)methanone;
(1-(2-((2-methoxy-4-(1-methyl-1H-pyrazol-4-yl)phenyl)
   amino)pyrido[3,4-d]pyrimidin-8-yl)pyrrolidin-3-yl)
   methanol;
(1-(2-((2-methoxy-4-(1-methyl-1H-pyrazol-4-yl)phenyl)
   amino)pyrido[3,4-d]pyrimidin-8-yl)piperidin-3-yl)
   methanol;
(4-(2-((2-methoxy-4-(1-methyl-1H-pyrazol-4-yl)phenyl)
   amino)pyrido[3,4-d]pyrimidin-8-yl)morpholin-2-yl)
   methanol;
N2-(2-(difluoromethoxy)-4-(1-methyl-1H-pyrazol-4-yl)
   phenyl)-N8-(2-methoxy-2-methylpropyl)pyrido[3,4-d]
   pyrimidine-2,8-diamine;
N2-(2-(difluoromethoxy)-4-fluorophenyl)-N8-(2-methoxy-
   2-methylpropyl)pyrido[3,4-d]pyrimidine-2,8-diamine;
N2-(4-(1-ethyl-1H-pyrazol-4-yl)-2-methoxyphenyl)-N8-(2-
   methoxy-2-methylpropyl)pyrido[3,4-d]pyrimidine-2,8-
   diamine;

(3-methoxy-4-((8-(neopentylamino)pyrido[3,4-d]pyrimidin-2-yl)amino)phenyl)(3-methoxyazetidin-1-yl)methanone;

N2-(2-methoxy-4-(tetrahydro-2H-pyran-4-yl)phenyl)-N8-((3-methyltetrahydrofuran-3-yl)methyl)pyrido[3,4-d]pyrimidine-2,8-diamine;

N2-(4-chloro-2-(difluoromethoxy)phenyl)-N8-(2-methoxy-2-methylpropyl)pyrido[3,4-d]pyrimidine-2,8-diamine;

N2-(2-methoxy-4-(4-methyl-4H-1,2,4-triazol-3-yl)phenyl)-5-methyl-N8-((3-methyloxetan-3-yl)methyl)pyrido[3,4-d]pyrimidine-2,8-diamine;

N2-(2-methoxy-4-(4-methyl-4H-1,2,4-triazol-3-yl)phenyl)-5-methyl-N8-((3-methyltetrahydrofuran-3-yl)methyl)pyrido[3,4-d]pyrimidine-2,8-diamine;

N-(2-methoxy-4-(4-methyl-4H-1,2,4-triazol-3-yl)phenyl)-5-methyl-8-(6-oxa-2-azaspiro[3.4]octan-2-yl)pyrido[3,4-d]pyrimidin-2-amine;

N8-(2-methoxy-2-methylpropyl)-N2-(2-methoxy-4-(1-methyl-1H-1,2,4-triazol-3-yl)phenyl)-6-methylpyrido[3,4-d]pyrimidine-2,8-diamine;

N2-(2-(difluoromethoxy)-4-(1-methyl-1H-pyrazol-4-yl)phenyl)-N8-(2-methoxy-2-methylpropyl)-6-methylpyrido[3,4-d]pyrimidine-2,8-diamine;

(4-(3-methoxy-4-((8-((2-methoxy-2-methylpropyl)amino)-6-methylpyrido[3,4-d]pyrimidin-2-yl)amino)phenyl)-1-methyl-1H-pyrazol-5-yl)methanol;

N2-(2-methoxy-4-(1-methyl-1H-1,2,3-triazol-5-yl)phenyl)-6-methyl-N8-neopentylpyrido[3,4-d]pyrimidine-2,8-diamine;

N2-(2-ethoxy-4-(4-methyl-4H-1,2,4-triazol-3-yl)phenyl)-6-methyl-N8-((3-methyltetrahydrofuran-3-yl)methyl)pyrido[3,4-d]pyrimidine-2,8-diamine;

1-(((2-((2-ethoxy-4-(4-methyl-4H-1,2,4-triazol-3-yl)phenyl)amino)-6-methylpyrido[3,4-d]pyrimidin-8-yl)amino)methyl)cyclobutanol;

1-(2-((2-ethoxy-4-(4-methyl-4H-1,2,4-triazol-3-yl)phenyl)amino)-6-methyl pyrido[3,4-d]pyrimidin-8-yl)-3-methylazetidine-3-carbonitrile;

N-(2-ethoxy-4-(4-methyl-4H-1,2,4-triazol-3-yl)phenyl)-6-methyl-8-(7-oxa-2-azaspiro[3.5]nonan-2-yl)pyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)piperidine-4-carbonitrile;

1-(2-((2-ethoxy-4-(4-methyl-4H-1,2,4-triazol-3-yl)phenyl)amino)-6-methylpyrido[3,4-d]pyrimidin-8-yl)-3-methylazetidin-3-ol;

N2-(2-ethoxy-4-(4-methyl-4H-1,2,4-triazol-3-yl)phenyl)-6-methyl-N8-((3-methyloxetan-3-yl)methyl)pyrido[3,4-d]pyrimidine-2,8-diamine;

N2-(2-ethoxy-4-(4-methyl-4H-1,2,4-triazol-3-yl)phenyl)-6-methyl-N8-(tetrahydro-2H-pyran-4-yl)pyrido[3,4-d]pyrimidine-2,8-diamine;

N-(2-ethoxy-4-(4-methyl-4H-1,2,4-triazol-3-yl)phenyl)-6-methyl-8-(2-oxa-7-azaspiro[4.4]nonan-7-yl)pyrido[3,4-d]pyrimidin-2-amine;

1-(((2-((2-ethoxy-4-(4-methyl-4H-1,2,4-triazol-3-yl)phenyl)amino)-6-methylpyrido[3,4-d]pyrimidin-8-yl)amino)methyl)cyclopropanol;

N2-(4-(1,2-dimethyl-1H-imidazol-5-yl)-2-methoxyphenyl)-6-methyl-N8-((3-methyltetrahydrofuran-3-yl)methyl)pyrido[3,4-d]pyrimidine-2,8-diamine;

N-(4-(1,2-dimethyl-1H-imidazol-5-yl)-2-methoxyphenyl)-6-methyl-8-(2-oxa-7-azaspiro[4.4]nonan-7-yl)pyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)piperidine-4-carbonitrile;

1-(2-((4-(1,2-dimethyl-1H-imidazol-5-yl)-2-methoxyphenyl)amino)-6-methylpyrido[3,4-d]pyrimidin-8-yl)-3-methylazetidine-3-carbonitrile;

N-(2-ethoxy-4-(4-methyl-4H-1,2,4-triazol-3-yl)phenyl)-6-methyl-8-(1-oxa-6-azaspiro[3.3]heptan-6-yl)pyrido[3,4-d]pyrimidin-2-amine;

N2-(2-methoxy-4-(1-methyl-1H-pyrazol-3-yl)phenyl)-6-methyl-N8-neopentylpyrido[3,4-d]pyrimidine-2,8-diamine;

8-(3,3-difluoroazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(4-methoxypiperidin-1-yl)-6-methylpyrido[3,4-d]pyrimidin-2-amine;

N-(2-ethoxy-4-(4-methyl-4H-1,2,4-triazol-3-yl)phenyl)-8-(3-methoxypiperidin-1-yl)-6-methylpyrido[3,4-d]pyrimidin-2-amine;

N-(2-ethoxy-4-(4-methyl-4H-1,2,4-triazol-3-yl)phenyl)-6-methyl-8-(2-methylmorpholino)pyrido[3,4-d]pyrimidin-2-amine;

N-(2-ethoxy-4-(4-methyl-4H-1,2,4-triazol-3-yl)phenyl)-8-(4-methoxy-4-methylpiperidin-1-yl)-6-methylpyrido[3,4-d]pyrimidin-2-amine;

8-(3-azabicyclo[3.1.0]hexan-3-yl)-N-(2-ethoxy-4-(4-methyl-4H-1,2,4-triazol-3-yl)phenyl)-6-methylpyrido[3,4-d]pyrimidin-2-amine;

8-(3-(dimethylamino)azetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)piperidin-4-ol;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylpyrrolidin-3-ol;

1-(2-((2-ethoxy-4-(4-methyl-4H-1,2,4-triazol-3-yl)phenyl)amino)-6-methylpyrido[3,4-d]pyrimidin-8-yl)-4-methylpiperidine-4-carbonitrile;

1-(2-((2-ethoxy-4-(4-methyl-4H-1,2,4-triazol-3-yl)phenyl)amino)-6-methylpyrido[3,4-d]pyrimidin-8-yl)pyrrolidine-3-carbonitrile;

N2-(2-methoxy-4-(1-methyl-1H-imidazol-2-yl)phenyl)-6-methyl-N8-neopentylpyrido[3,4-d]pyrimidine-2,8-diamine;

N2-(2-methoxy-4-(1-methyl-1H-pyrazol-5-yl)phenyl)-6-methyl-N8-neopentylpyrido[3,4-d]pyrimidine-2,8-diamine;

N2-(2-methoxy-4-(oxazol-2-yl)phenyl)-6-methyl-N8-neopentylpyrido[3,4-d]pyrimidine-2,8-diamine;

N-(2-ethoxy-4-(4-methyl-4H-1,2,4-triazol-3-yl)phenyl)-8-(3-methoxypyrrolidin-1-yl)-6-methylpyrido[3,4-d]pyrimidin-2-amine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylpyrrolidine-3-carbonitrile;

8-(2,2-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-6-methyl-8-(3-(trifluoromethyl)azetidin-1-yl)pyrido[3,4-d]pyrimidin-2-amine;

N-(2-ethoxy-4-(4-methyl-4H-1,2,4-triazol-3-yl)phenyl)-6-methyl-8-(2-azaspiro[3.3]heptan-2-yl)pyrido[3,4-d]pyrimidin-2-amine;

(R)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

(S)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

N2-(2-ethoxy-4-(4-methyl-4H-1,2,4-triazol-3-yl)phenyl)-N8-((1-methoxycyclobutyl)methyl)-6-methylpyrido[3,4-d]pyrimidine-2,8-diamine;

N2-(2-ethoxy-4-(4-methyl-4H-1,2,4-triazol-3-yl)phenyl)-6-methyl-N8-(1-methylazetidin-3-yl)pyrido[3,4-d]pyrimidine-2,8-diamine;

N2-(2-ethoxy-4-(4-methyl-4H-1,2,4-triazol-3-yl)phenyl)-6-methyl-N8-(oxetan-3-ylmethyl)pyrido[3,4-d]pyrimidine-2,8-diamine;

N-(2-ethoxy-4-(4-methyl-4H-1,2,4-triazol-3-yl)phenyl)-6-methyl-8-(pyrrolidin-1-yl)pyrido[3,4-d]pyrimidin-2-amine;

N-(2-ethoxy-4-(4-methyl-4H-1,2,4-triazol-3-yl)phenyl)-6-methyl-8-(2-azaspiro[3.4]octan-2-yl)pyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-ethylazetidin-3-ol;

N2-(2-ethoxy-4-(4-methyl-4H-1,2,4-triazol-3-yl)phenyl)-6-methyl-N8-(1-methylpiperidin-4-yl)pyrido[3,4-d]pyrimidine-2,8-diamine;

8-(4-(dimethylamino)piperidin-1-yl)-N-(2-ethoxy-4-(4-methyl-4H-1,2,4-triazol-3-yl)phenyl)-6-methylpyrido[3,4-d]pyrimidin-2-amine;

N2-(2-ethoxy-4-(4-methyl-4H-1,2,4-triazol-3-yl)phenyl)-6-methyl-N8-((tetrahydro-2H-pyran-4-yl)methyl)pyrido[3,4-d]pyrimidine-2,8-diamine;

N2-(2-ethoxy-4-(4-methyl-4H-1,2,4-triazol-3-yl)phenyl)-6-methyl-N8-((4-methyltetrahydro-2H-pyran-4-yl)methyl)pyrido[3,4-d]pyrimidine-2,8-diamine;

1-(2-((2-ethoxy-4-(4-methyl-4H-1,2,4-triazol-3-yl)phenyl)amino)-6-methylpyrido[3,4-d]pyrimidin-8-yl)-4-ethylpiperidine-4-carbonitrile;

N2-(2-ethoxy-4-(4-methyl-4H-1,2,4-triazol-3-yl)phenyl)-6-methyl-N8-(2-(3-methyltetrahydrofuran-3-yl)ethyl)pyrido[3,4-d]pyrimidine-2,8-diamine;

N2-(2-ethoxy-4-(4-methyl-4H-1,2,4-triazol-3-yl)phenyl)-6-methyl-N8-(1-(tetrahydro-2H-pyran-4-yl)ethyl)pyrido[3,4-d]pyrimidine-2,8-diamine;

N2-(2-ethoxy-4-(4-methyl-4H-1,2,4-triazol-3-yl)phenyl)-6-methyl-N8-(pentan-3-yl)pyrido[3,4-d]pyrimidine-2,8-diamine;

N2-(2-ethoxy-4-(4-methyl-4H-1,2,4-triazol-3-yl)phenyl)-6-methyl-N8-(tetrahydrofuran-3-yl)pyrido[3,4-d]pyrimidine-2,8-diamine;

8-(3-ethoxy-3-methylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-ethyl-3-methoxyazetidin-1-yl)-6-methylpyrido[3,4-d]pyrimidin-2-amine;

8-(3-ethoxy-3-ethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-isopropyl-3-methoxyazetidin-1-yl)-6-methylpyrido[3,4-d]pyrimidin-2-amine;

8-(3-ethoxy-3-isopropylazetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-ethylazetidine-3-carbonitrile;

1-(2-((2-ethoxy-4-(4-methyl-4H-1,2,4-triazol-3-yl)phenyl)amino)-6-methylpyrido[3,4-d]pyrimidin-8-yl)-3-isopropylazetidine-3-carbonitrile;

1-(2-((2-ethoxy-4-(4-methyl-4H-1,2,4-triazol-3-yl)phenyl)amino)-6-methylpyrido[3,4-d]pyrimidin-8-yl)-2,2,3-trimethylazetidine-3-carbonitrile;

N-(2-ethoxy-4-(4-methyl-4H-1,2,4-triazol-3-yl)phenyl)-8-(3-methoxy-2,2-dimethylazetidin-1-yl)-6-methylpyrido[3,4-d]pyrimidin-2-amine;

N-(2-ethoxy-4-(4-methyl-4H-1,2,4-triazol-3-yl)phenyl)-8-(3-methoxy-2,2,3-trimethylazetidin-1-yl)-6-methylpyrido[3,4-c]pyrimidin-2-amine;

1-(2-((2-ethoxy-4-(4-methyl-4H-1,2,4-triazol-3-yl)phenyl)amino)-6-methylpyrido[3,4-c]pyrimidin-8-yl)-2,2-dimethylazetidine-3-carbonitrile;

N2-(2-methoxy-4-(4-methyl-4H-1,2,4-triazol-3-yl)phenyl)-6-methyl-N8-(1-methylpiperidin-4-yl)pyrido[3,4-c]pyrimidine-2,8-diamine;

8-(4-(dimethylamino)piperidin-1-yl)-N-(2-methoxy-4-(4-methyl-4H-1,2,4-triazol-3-yl)phenyl)-6-methylpyrido[3,4-d]pyrimidin-2-amine;

N2-(2-methoxy-4-(4-methyl-4H-1,2,4-triazol-3-yl)phenyl)-6-methyl-N8-((tetrahydro-2H-pyran-4-yl)methyl)pyrido[3,4-c]pyrimidine-2,8-diamine;

N2-(2-methoxy-4-(4-methyl-4H-1,2,4-triazol-3-yl)phenyl)-6-methyl-N8-((4-methyltetrahydro-2H-pyran-4-yl)methyl)pyrido[3,4-d]pyrimidine-2,8-diamine;

4-ethyl-1-(2-((2-methoxy-4-(4-methyl-4H-1,2,4-triazol-3-yl)phenyl)amino)-6-methylpyrido[3,4-c]pyrimidin-8-yl)piperidine-4-carbonitrile;

N2-(2-methoxy-4-(4-methyl-4H-1,2,4-triazol-3-yl)phenyl)-6-methyl-N8-(2-(3-methyltetrahydrofuran-3-yl)ethyl)pyrido[3,4-d]pyrimidine-2,8-diamine;

N2-(2-methoxy-4-(4-methyl-4H-1,2,4-triazol-3-yl)phenyl)-6-methyl-N8-(1-(tetrahydro-2H-pyran-4-yl)ethyl)pyrido[3,4-d]pyrimidine-2,8-diamine;

N2-(2-methoxy-4-(4-methyl-4H-1,2,4-triazol-3-yl)phenyl)-6-methyl-N8-(pentan-3-yl)pyrido[3,4-c]pyrimidine-2,8-diamine;

N2-(2-methoxy-4-(4-methyl-4H-1,2,4-triazol-3-yl)phenyl)-6-methyl-N8-(tetrahydrofuran-3-yl)pyrido[3,4-c]pyrimidine-2,8-diamine;

8-(3-ethoxy-3-methylazetidin-1-yl)-N-(2-methoxy-4-(4-methyl-4H-1,2,4-triazol-3-yl)phenyl)-6-methylpyrido[3,4-d]pyrimidin-2-amine;

8-(3-ethyl-3-methoxyazetidin-1-yl)-N-(2-methoxy-4-(4-methyl-4H-1,2,4-triazol-3-yl)phenyl)-6-methylpyrido[3,4-d]pyrimidin-2-amine;

8-(3-ethoxy-3-ethylazetidin-1-yl)-N-(2-methoxy-4-(4-methyl-4H-1,2,4-triazol-3-yl)phenyl)-6-methylpyrido[3,4-d]pyrimidin-2-amine;

8-(3-isopropyl-3-methoxyazetidin-1-yl)-N-(2-methoxy-4-(4-methyl-4H-1,2,4-triazol-3-yl)phenyl)-6-methylpyrido[3,4-d]pyrimidin-2-amine;

8-(3-ethoxy-3-isopropylazetidin-1-yl)-N-(2-methoxy-4-(4-methyl-4H-1,2,4-triazol-3-yl)phenyl)-6-methylpyrido[3,4-d]pyrimidin-2-amine;
3-ethyl-1-(2-((2-methoxy-4-(4-methyl-4H-1,2,4-triazol-3-yl)phenyl)amino)-6-methyl pyrido[3,4-c]pyrimidin-8-yl)azetidine-3-carbonitrile;
3-isopropyl-1-(2-((2-methoxy-4-(4-methyl-4H-1,2,4-triazol-3-yl)phenyl)amino)-6-methyl pyrido[3,4-c]pyrimidin-8-yl)azetidine-3-carbonitrile;
1-(2-((2-methoxy-4-(4-methyl-4H-1,2,4-triazol-3-yl)phenyl)amino)-6-methylpyrido[3,4-d]pyrimidin-8-yl)-2,2,3-trimethylazetidine-3-carbonitrile;
8-(3-methoxy-2,2-dimethylazetidin-1-yl)-N-(2-methoxy-4-(4-methyl-4H-1,2,4-triazol-3-yl)phenyl)-6-methylpyrido[3,4-d]pyrimidin-2-amine;
8-(3-methoxy-2,2,3-trimethylazetidin-1-yl)-N-(2-methoxy-4-(4-methyl-4H-1,2,4-triazol-3-yl)phenyl)-6-methylpyrido[3,4-d]pyrimidin-2-amine;
1-(2-((2-methoxy-4-(4-methyl-4H-1,2,4-triazol-3-yl)phenyl)amino)-6-methylpyrido[3,4-d]pyrimidin-8-yl)-2,2-dimethylazetidine-3-carbonitrile;
8-(3,3-dimethylazetidin-1-yl)-N-(2-methoxy-4-(1-methyl-1H-tetrazol-5-yl)phenyl)-6-methylpyrido[3,4-d]pyrimidin-2-amine;
1-(2-((2-methoxy-4-(1-methyl-1H-tetrazol-5-yl)phenyl)amino)-6-methylpyrido[3,4-d]pyrimidin-8-yl)-4-methylpiperidine-4-carbonitrile;
8-(3-methoxy-3-methylazetidin-1-yl)-N-(2-methoxy-4-(1-methyl-1H-tetrazol-5-yl)phenyl)-6-methylpyrido[3,4-d]pyrimidin-2-amine;
N-(2-methoxy-4-(1-methyl-1H-tetrazol-5-yl)phenyl)-8-(4-methoxypiperidin-1-yl)-6-methylpyrido[3,4-d]pyrimidin-2-amine;
N-(2-methoxy-4-(1-methyl-1H-tetrazol-5-yl)phenyl)-8-(4-methoxy-4-methylpiperidin-1-yl)-6-methylpyrido[3,4-d]pyrimidin-2-amine;
N-(2-methoxy-4-(1-methyl-1H-tetrazol-5-yl)phenyl)-6-methyl-8-(1-oxa-6-azaspiro[3.3]heptan-6-yl)pyrido[3,4-d]pyrimidin-2-amine;
1-(2-((2-methoxy-4-(1-methyl-1H-tetrazol-5-yl)phenyl)amino)-6-methylpyrido[3,4-d]pyrimidin-8-yl)-3-methylazetidine-3-carbonitrile;
N2-(2-methoxy-4-(1-methyl-1H-tetrazol-5-yl)phenyl)-6-methyl-N8-((3-methyltetrahydrofuran-3-yl)methyl)pyrido[3,4-d]pyrimidine-2,8-diamine;
N-(2-methoxy-4-(1-methyl-1H-tetrazol-5-yl)phenyl)-6-methyl-8-(2-oxa-7-azaspiro[4.4]nonan-7-yl)pyrido[3,4-d]pyrimidin-2-amine;
N2-(2-methoxy-4-(1-methyl-1H-tetrazol-5-yl)phenyl)-6-methyl-N8-(tetrahydro-2H-pyran-4-yl)pyrido[3,4-d]pyrimidine-2,8-diamine;
N-(2-methoxy-4-(1-methyl-1H-tetrazol-5-yl)phenyl)-6-methyl-8-(7-oxa-2-azaspiro[3.5]nonan-2-yl)pyrido[3,4-d]pyrimidin-2-amine;
N2-(2-methoxy-4-(1-methyl-1H-tetrazol-5-yl)phenyl)-6-methyl-N8-neopentylpyrido[3,4-d]pyrimidine-2,8-diamine;
N-(2-(difluoromethoxy)-4-(4-methyl-4H-1,2,4-triazol-3-yl)phenyl)-8-(3,3-dimethylazetidin-1-yl)-6-methylpyrido[3,4-d]pyrimidin-2-amine;
1-(2-((2-(difluoromethoxy)-4-(4-methyl-4H-1,2,4-triazol-3-yl)phenyl)amino)-6-methylpyrido[3,4-d]pyrimidin-8-yl)-4-methylpiperidine-4-carbonitrile;
N-(2-(difluoromethoxy)-4-(4-methyl-4H-1,2,4-triazol-3-yl)phenyl)-8-(methoxy-3-methylazetidin-1-yl)-6-methylpyrido[3,4-d]pyrimidin-2-amine;
N-(2-(difluoromethoxy)-4-(4-methyl-4H-1,2,4-triazol-3-yl)phenyl)-8-(4-methoxypiperidin-1-yl)-6-methylpyrido[3,4-d]pyrimidin-2-amine;
N-(2-(difluoromethoxy)-4-(4-methyl-4H-1,2,4-triazol-3-yl)phenyl)-8-(4-methoxy-4-methylpiperidin-1-yl)-6-methylpyrido[3,4-d]pyrimidin-2-amine;
N-(2-(difluoromethoxy)-4-(4-methyl-4H-1,2,4-triazol-3-yl)phenyl)-6-methyl-8-(1-oxa-6-azaspiro[3.3]heptan-6-yl)pyrido[3,4-d]pyrimidin-2-amine;
1-(2-((2-(difluoromethoxy)-4-(4-methyl-4H-1,2,4-triazol-3-yl)phenyl)amino)-6-methylpyrido[3,4-d]pyrimidin-8-yl)-3-methylazetidine-3-carbonitrile;
N2-(2-(difluoromethoxy)-4-(4-methyl-4H-1,2,4-triazol-3-yl)phenyl)-6-methyl-N8-((3-methyltetrahydrofuran-3-yl)methyl)pyrido[3,4-d]pyrimidine-2,8-diamine;
N-(2-(difluoromethoxy)-4-(4-methyl-4H-1,2,4-triazol-3-yl)phenyl)-6-methyl-8-(2-oxa-7-azaspiro[4.4]nonan-7-yl)pyrido[3,4-d]pyrimidin-2-amine;
N2-(2-(difluoromethoxy)-4-(4-methyl-4H-1,2,4-triazol-3-yl)phenyl)-6-methyl-N8-(tetrahydro-2H-pyran-4-yl)pyrido[3,4-d]pyrimidine-2,8-diamine;
N-(2-(difluoromethoxy)-4-(4-methyl-4H-1,2,4-triazol-3-yl)phenyl)-6-methyl-8-(7-oxa-2-azaspiro[3.5]nonan-2-yl)pyrido[3,4-d]pyrimidin-2-amine;
N2-(2-(difluoromethoxy)-4-(4-methyl-4H-1,2,4-triazol-3-yl)phenyl)-6-methyl-N8-neopentylpyrido[3,4-d]pyrimidine-2,8-diamine;
8-(3,3-dimethylazetidin-1-yl)-N-(4-(4-ethyl-4H-1,2,4-triazol-3-yl)-2-methoxyphenyl)-6-methylpyrido[3,4-d]pyrimidin-2-amine;
1-(2-((4-(4-ethyl-4H-1,2,4-triazol-3-yl)-2-methoxyphenyl)amino)-6-methylpyrido[3,4-d]pyrimidin-8-yl)-4-methylpiperidine-4-carbonitrile;
N-(4-(4-ethyl-4H-1,2,4-triazol-3-yl)-2-methoxyphenyl)-8-(3-methoxy-3-methylazetidin-1-yl)-6-methylpyrido[3,4-d]pyrimidin-2-amine;
N-(4-(4-ethyl-4H-1,2,4-triazol-3-yl)-2-methoxyphenyl)-8-(4-methoxypiperidin-1-yl)-6-methylpyrido[3,4-d]pyrimidin-2-amine;
N-(4-(4-ethyl-4H-1,2,4-triazol-3-yl)-2-methoxyphenyl)-8-(4-methoxy-4-methylpiperidin-1-yl)-6-methylpyrido[3,4-d]pyrimidin-2-amine;
N-(4-(4-ethyl-4H-1,2,4-triazol-3-yl)-2-methoxyphenyl)-6-methyl-8-(1-oxa-6-azaspiro[3.3]heptan-6-yl)pyrido[3,4-d]pyrimidin-2-amine;
1-(2-((4-(4-ethyl-4H-1,2,4-triazol-3-yl)-2-methoxyphenyl)amino)-6-methylpyrido[3,4-d]pyrimidin-8-yl)-3-methylazetidine-3-carbonitrile;
N2-(4-(4-ethyl-4H-1,2,4-triazol-3-yl)-2-methoxyphenyl)-6-methyl-N8-((3-methyltetrahydrofuran-3-yl)methyl)pyrido[3,4-d]pyrimidine-2,8-diamine;
N-(4-(4-ethyl-4H-1,2,4-triazol-3-yl)-2-methoxyphenyl)-6-methyl-8-(2-oxa-7-azaspiro[4.4]nonan-7-yl)pyrido[3,4-d]pyrimidin-2-amine;
N2-(4-(4-ethyl-4H-1,2,4-triazol-3-yl)-2-methoxyphenyl)-6-methyl-N8-(tetrahydro-2H-pyran-4-yl)pyrido[3,4-d]pyrimidine-2,8-diamine;
N-(4-(4-ethyl-4H-1,2,4-triazol-3-yl)-2-methoxyphenyl)-6-methyl-8-(7-oxa-2-azaspiro[3.5]nonan-2-yl)pyrido[3,4-d]pyrimidin-2-amine;
N2-(4-(4-ethyl-4H-1,2,4-triazol-3-yl)-2-methoxyphenyl)-6-methyl-N8-neopentylpyrido[3,4-d]pyrimidine-2,8-diamine;
8-(3,3-dimethylazetidin-1-yl)-N-(2-ethoxy-4-(4-ethyl-4H-1,2,4-triazol-3-yl)phenyl)-6-methylpyrido[3,4-d]pyrimidin-2-amine;

1-(2-((2-ethoxy-4-(4-ethyl-4H-1,2,4-triazol-3-yl)phenyl) amino)-6-methylpyrido[3,4-d]pyrimidin-8-yl)-4-methylpiperidine-4-carbonitrile;

N-(2-ethoxy-4-(4-ethyl-4H-1,2,4-triazol-3-yl)phenyl)-8-(3-methoxy-3-methylazetidin-1-yl)-6-methylpyrido[3,4-d]pyrimidin-2-amine;

N-(2-ethoxy-4-(4-ethyl-4H-1,2,4-triazol-3-yl)phenyl)-8-(4-methoxypiperidin-1-yl)-6-methylpyrido[3,4-d]pyrimidin-2-amine;

N-(2-ethoxy-4-(4-ethyl-4H-1,2,4-triazol-3-yl)phenyl)-8-(4-methoxy-4-methylpiperidin-1-yl)-6-methylpyrido[3,4-d]pyrimidin-2-amine;

N-(2-ethoxy-4-(4-ethyl-4H-1,2,4-triazol-3-yl)phenyl)-6-methyl-8-(1-oxa-6-azaspiro[3.3]heptan-6-yl)pyrido[3,4-d]pyrimidin-2-amine;

1-(2-((2-ethoxy-4-(4-ethyl-4H-1,2,4-triazol-3-yl)phenyl) amino)-6-methylpyrido[3,4-d]pyrimidin-8-yl)-3-methylazetidine-3-carbonitrile;

N2-(2-ethoxy-4-(4-ethyl-4H-1,2,4-triazol-3-yl)phenyl)-6-methyl-N8-((3-methyltetrahydrofuran-3-yl)methyl) pyrido[3,4-d]pyrimidine-2,8-diamine;

N-(2-ethoxy-4-(4-ethyl-4H-1,2,4-triazol-3-yl)phenyl)-6-methyl-8-(2-oxa-7-azaspiro[4.4]nonan-7-yl)pyrido[3,4-d]pyrimidin-2-amine;

N2-(2-ethoxy-4-(4-ethyl-4H-1,2,4-triazol-3-yl)phenyl)-6-methyl-N8-(tetrahydro-2H-pyran-4-yl)pyrido[3,4-d]pyrimidine-2,8-diamine;

N-(2-ethoxy-4-(4-ethyl-4H-1,2,4-triazol-3-yl)phenyl)-6-methyl-8-(7-oxa-2-azaspiro[3.5]nonan-2-yl)pyrido[3,4-d]pyrimidin-2-amine;

N2-(2-ethoxy-4-(4-ethyl-4H-1,2,4-triazol-3-yl)phenyl)-6-methyl-N8-neopentylpyrido[3,4-d]pyrimidine-2,8-diamine;

N-(4-(4,5-dimethyl-4H-1,2,4-triazol-3-yl)-2-methoxyphenyl)-8-(3,3-dimethylazetidin-1-yl)-6-methylpyrido[3,4-d]pyrimidin-2-amine;

1-(2-((4-(4,5-dimethyl-4H-1,2,4-triazol-3-yl)-2-methoxyphenyl)amino)-6-methylpyrido[3,4-d]pyrimidin-8-yl)-4-methylpiperidine-4-carbonitrile;

N-(4-(4,5-dimethyl-4H-1,2,4-triazol-3-yl)-2-methoxyphenyl)-8-(3-methoxy-3-methylazetidin-1-yl)-6-methylpyrido[3,4-d]pyrimidin-2-amine;

N-(4-(4,5-dimethyl-4H-1,2,4-triazol-3-yl)-2-methoxyphenyl)-8-(4-methoxypiperidin-1-yl)-6-methylpyrido[3,4-d]pyrimidin-2-amine;

N-(4-(4,5-dimethyl-4H-1,2,4-triazol-3-yl)-2-methoxyphenyl)-8-(4-methoxy-4-methylpiperidin-1-yl)-6-methylpyrido[3,4-d]pyrimidin-2-amine;

N-(4-(4,5-dimethyl-4H-1,2,4-triazol-3-yl)-2-methoxyphenyl)-6-methyl-8-(1-oxa-6-azaspiro[3.3]heptan-6-yl)pyrido[3,4-d]pyrimidin-2-amine;

1-(2-((4-(4,5-dimethyl-4H-1,2,4-triazol-3-yl)-2-methoxyphenyl)amino)-6-methylpyrido[3,4-d]pyrimidin-8-yl)-3-methylazetidine-3-carbonitrile;

N2-(4-(4,5-dimethyl-4H-1,2,4-triazol-3-yl)-2-methoxyphenyl)-6-methyl-N8-((3-methyltetrahydrofuran-3-yl)methyl)pyrido[3,4-d]pyrimidine-2,8-diamine;

N-(4-(4,5-dimethyl-4H-1,2,4-triazol-3-yl)-2-methoxyphenyl)-6-methyl-8-(2-oxa-7-azaspiro[4.4]nonan-7-yl)pyrido[3,4-d]pyrimidin-2-amine;

N2-(4-(4,5-dimethyl-4H-1,2,4-triazol-3-yl)-2-methoxyphenyl)-6-methyl-N8-(tetrahydro-2H-pyran-4-yl)pyrido[3,4-d]pyrimidine-2,8-diamine;

N-(4-(4,5-dimethyl-4H-1,2,4-triazol-3-yl)-2-methoxyphenyl)-6-methyl-8-(7-oxa-2-azaspiro[3.5]nonan-2-yl)pyrido[3,4-d]pyrimidin-2-amine;

N2-(4-(4,5-dimethyl-4H-1,2,4-triazol-3-yl)-2-methoxyphenyl)-6-methyl-N8-neopentylpyrido[3,4-d]pyrimidine-2,8-diamine;

N-(4-(4,5-dimethyl-4H-1,2,4-triazol-3-yl)-2-ethoxyphenyl)-8-(3,3-dimethylazetidin-1-yl)-6-methylpyrido[3,4-d]pyrimidin-2-amine;

1-(2-((4-(4,5-dimethyl-4H-1,2,4-triazol-3-yl)-2-ethoxyphenyl)amino)-6-methylpyrido[3,4-d]pyrimidin-8-yl)-4-methylpiperidine-4-carbonitrile;

N-(4-(4,5-dimethyl-4H-1,2,4-triazol-3-yl)-2-ethoxyphenyl)-8-(3-methoxy-3-methylazetidin-1-yl)-6-methylpyrido[3,4-d]pyrimidin-2-amine;

N-(4-(4,5-dimethyl-4H-1,2,4-triazol-3-yl)-2-ethoxyphenyl)-8-(4-methoxypiperidin-1-yl)-6-methylpyrido[3,4-d]pyrimidin-2-amine;

N-(4-(4,5-dimethyl-4H-1,2,4-triazol-3-yl)-2-ethoxyphenyl)-8-(4-methoxy-4-methylpiperidin-1-yl)-6-methylpyrido[3,4-d]pyrimidin-2-amine;

N-(4-(4,5-dimethyl-4H-1,2,4-triazol-3-yl)-2-ethoxyphenyl)-6-methyl-8-(1-oxa-6-azaspiro[3.3]heptan-6-yl)pyrido[3,4-d]pyrimidin-2-amine;

1-(2-((4-(4,5-dimethyl-4H-1,2,4-triazol-3-yl)-2-ethoxyphenyl)amino)-6-methylpyrido[3,4-d]pyrimidin-8-yl)-3-methylazetidine-3-carbonitrile;

N2-(4-(4,5-dimethyl-4H-1,2,4-triazol-3-yl)-2-ethoxyphenyl)-6-methyl-N8-((3-methyltetrahydrofuran-3-yl)methyl)pyrido[3,4-d]pyrimidine-2,8-diamine;

N-(4-(4,5-dimethyl-4H-1,2,4-triazol-3-yl)-2-ethoxyphenyl)-6-methyl-8-(2-oxa-7-azaspiro[4.4]nonan-7-yl)pyrido[3,4-d]pyrimidin-2-amine;

N2-(4-(4,5-dimethyl-4H-1,2,4-triazol-3-yl)-2-ethoxyphenyl)-6-methyl-N8-(tetrahydro-2H-pyran-4-yl)pyrido[3,4-d]pyrimidine-2,8-diamine;

N-(4-(4,5-dimethyl-4H-1,2,4-triazol-3-yl)-2-ethoxyphenyl)-6-methyl-8-(7-oxa-2-azaspiro[3.5]nonan-2-yl)pyrido[3,4-d]pyrimidin-2-amine;

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

8-(3,3-dimethylazetidin-1-yl)-N-(2-methoxy-4-(1-methyl-1H-1,2,3-triazol-5-yl)phenyl)-6-methylpyrido[3,4-d]pyrimidin-2-amine;

1-(2-((2-methoxy-4-(1-methyl-1H-1,2,3-triazol-5-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-1,2,3-triazol-5-yl)phenyl)-6-methylpyrido[3,4-d]pyrimidin-2-amine;

N-(2-methoxy-4-(1-methyl-1H-1,2,3-triazol-5-yl)phenyl)-8-(4-methoxypiperidin-1-yl)-6-methylpyrido[3,4-d]pyrimidin-2-amine;

N-(2-methoxy-4-(1-methyl-1H-1,2,3-triazol-5-yl)phenyl)-8-(4-methoxy-4-methylpiperidin-1-yl)-6-methylpyrido[3,4-d]pyrimidin-2-amine;

N-(2-methoxy-4-(1-methyl-1H-1,2,3-triazol-5-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-1,2,3-triazol-5-yl)phenyl)amino)-6-methylpyrido[3,4-d]pyrimidin-8-yl)-3-methylazetidine-3-carbonitrile;

N2-(2-methoxy-4-(1-methyl-1H-1,2,3-triazol-5-yl)phenyl)-6-methyl-N8-((3-methyltetrahydrofuran-3-yl)methyl)pyrido[3,4-d]pyrimidine-2,8-diamine;

N-(2-methoxy-4-(1-methyl-1H-1,2,3-triazol-5-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-1,2,3-triazol-5-yl)phenyl)-6-methyl-N8-(tetrahydro-2H-pyran-4-yl)pyrido[3,4-d]pyrimidine-2,8-diamine;

N-(2-methoxy-4-(1-methyl-1H-1,2,3-triazol-5-yl)phenyl)-6-methyl-8-(7-oxa-2-azaspiro[3.5]nonan-2-yl)pyrido[3,4-d]pyrimidin-2-amine;

N-(4-(1,2-dimethyl-1H-imidazol-5-yl)-2-methoxyphenyl)-8-(3,3-dimethylazetidin-1-yl)-6-methylpyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)-4-methylpiperidine-4-carbonitrile;

N-(4-(1,2-dimethyl-1H-imidazol-5-yl)-2-methoxyphenyl)-8-(3-methoxy-3-methylazetidin-1-yl)-6-methylpyrido[3,4-d]pyrimidin-2-amine;

N-(4-(1,2-dimethyl-1H-imidazol-5-yl)-2-methoxyphenyl)-8-(4-methoxypipendin-1-yl)-6-methylpyrido[3,4-d]pyrimidin-2-amine;

N-(4-(1,2-dimethyl-1H-imidazol-5-yl)-2-methoxyphenyl)-8-(4-methoxy-4-methylpiperidin-1-yl)-6-methylpyrido[3,4-d]pyrimidin-2-amine;

N-(4-(1,2-dimethyl-1H-imidazol-5-yl)-2-methoxyphenyl)-6-methyl-8-(1-oxa-6-azaspiro[3.3]heptan-6-yl)pyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)-3-methylazetidine-3-carbonitrile;

N-(4-(1,2-dimethyl-1H-imidazol-5-yl)-2-methoxyphenyl)-6-methyl-8-(2-oxa-7-azaspiro[4.4]nonan-7-yl)pyrido[3,4-d]pyrimidin-2-amine;

N2-(4-(1,2-dimethyl-1H-imidazol-5-yl)-2-methoxyphenyl)-6-methyl-N8-(tetrahydro-2H-pyran-4-yl)pyrido[3,4-d]pyrimidine-2,8-diamine;

N-(4-(1,2-dimethyl-1H-imidazol-5-yl)-2-methoxyphenyl)-6-methyl-8-(7-oxa-2-azaspiro[3.5]nonan-2-yl)pyrido[3,4-d]pyrimidin-2-amine;

N-(4-(1,5-dimethyl-1H-imidazol-2-yl)-2-methoxyphenyl)-8-(3,3-dimethylazetidin-1-yl)-6-methylpyrido[3,4-d]pyrimidin-2-amine;

1-(2-((4-(1,5-dimethyl-1H-imidazol-2-yl)-2-methoxyphenyl)amino)-6-methylpyrido[3,4-d]pyrimidin-8-yl)-4-methylpiperidine-4-carbonitrile;

N-(4-(1,5-dimethyl-1H-imidazol-2-yl)-2-methoxyphenyl)-8-(3-methoxy-3-methylazetidin-1-yl)-6-methylpyrido[3,4-d]pyrimidin-2-amine;

N-(4-(1,5-dimethyl-1H-imidazol-2-yl)-2-methoxyphenyl)-8-(4-methoxypiperidin-1-yl)-6-methylpyrido[3,4-d]pyrimidin-2-amine;

N-(4-(1,5-dimethyl-1H-imidazol-2-yl)-2-methoxyphenyl)-8-(4-methoxy-4-methylpiperidin-1-yl)-6-methylpyrido[3,4-d]pyrimidin-2-amine;

N-(4-(1,5-dimethyl-1H-imidazol-2-yl)-2-methoxyphenyl)-6-methyl-8-(1-oxa-6-azaspiro[3.3]heptan-6-yl)pyrido[3,4-d]pyrimidin-2-amine;

1-(2-((4-(1,5-dimethyl-1H-imidazol-2-yl)-2-methoxyphenyl)amino)-6-methylpyrido[3,4-d]pyrimidin-8-yl)-3-methylazetidine-3-carbonitrile;

N2-(4-(1,5-dimethyl-1H-imidazol-2-yl)-2-methoxyphenyl)-6-methyl-N8-((3-methyltetrahydrofuran-3-yl)methyl)pyrido[3,4-d]pyrimidine-2,8-diamine;

N-(4-(1,5-dimethyl-1H-imidazol-2-yl)-2-methoxyphenyl)-6-methyl-8-(2-oxa-7-azaspiro[4.4]nonan-7-yl)pyrido[3,4-d]pyrimidin-2-amine;

N2-(4-(1,5-dimethyl-1H-imidazol-2-yl)-2-methoxyphenyl)-6-methyl-N8-(tetrahydro-2H-pyran-4-yl)pyrido[3,4-d]pyrimidine-2,8-diamine;

N-(4-(1,5-dimethyl-1H-imidazol-2-yl)-2-methoxyphenyl)-6-methyl-8-(7-oxa-2-azaspiro[3.5]nonan-2-yl)pyrido[3,4-d]pyrimidin-2-amine;

N2-(4-(1,5-dimethyl-1H-imidazol-2-yl)-2-methoxyphenyl)-6-methyl-N8-neopentylpyrido[3,4-d]pyrimidine-2,8-diamine;

8-(3,3-dimethylazetidin-1-yl)-N-(2-methoxy-4-(1-methyl-1H-imidazol-2-yl)phenyl)-6-methylpyrido[3,4-d]pyrimidin-2-amine;

1-(2-((2-methoxy-4-(1-methyl-1H-imidazol-2-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-imidazol-2-yl)phenyl)-6-methylpyrido[3,4-d]pyrimidin-2-amine;

N-(2-methoxy-4-(1-methyl-1H-imidazol-2-yl)phenyl)-8-(4-methoxypiperidin-1-yl)-6-methylpyrido[3,4-d]pyrimidin-2-amine;

N-(2-methoxy-4-(1-methyl-1H-imidazol-2-yl)phenyl)-8-(4-methoxy-4-methylpiperidin-1-yl)-6-methylpyrido[3,4-d]pyrimidin-2-amine;

N-(2-methoxy-4-(1-methyl-1H-imidazol-2-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-imidazol-2-yl)phenyl)amino)-6-methylpyrido[3,4-d]pyrimidin-8-yl)-3-methylazetidine-3-carbonitrile;

N2-(2-methoxy-4-(1-methyl-1H-imidazol-2-yl)phenyl)-6-methyl-N8-((3-methyltetrahydrofuran-3-yl)methyl)pyrido[3,4-d]pyrimidine-2,8-diamine;

N-(2-methoxy-4-(1-methyl-1H-imidazol-2-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-imidazol-2-yl)phenyl)-6-methyl-N8-(tetrahydro-2H-pyran-4-yl)pyrido[3,4-d]pyrimidine-2,8-diamine;

N-(2-methoxy-4-(1-methyl-1H-imidazol-2-yl)phenyl)-6-methyl-8-(7-oxa-2-azaspiro[3.5]nonan-2-yl)pyrido[3,4-d]pyrimidin-2-amine;

8-(3,3-dimethylazetidin-1-yl)-N-(4-(2,4-dimethyloxazol-5-yl)-2-methoxyphenyl)-6-methylpyrido[3,4-d]pyrimidin-2-amine;

1-(2-((4-(2,4-dimethyloxazol-5-yl)-2-methoxyphenyl)amino)-6-methylpyrido[3,4-d]pyrimidin-8-yl)-4-methylpiperidine-4-carbonitrile;

N-(4-(2,4-dimethyloxazol-5-yl)-2-methoxyphenyl)-8-(3-methoxy-3-methylazetidin-1-yl)-6-methylpyrido[3,4-d]pyrimidin-2-amine;

N-(4-(2,4-dimethyloxazol-5-yl)-2-methoxyphenyl)-8-(4-methoxypiperidin-1-yl)-6-methylpyrido[3,4-d]pyrimidin-2-amine;

N-(4-(2,4-dimethyloxazol-5-yl)-2-methoxyphenyl)-8-(4-methoxy-4-methylpiperidin-1-yl)-6-methylpyrido[3,4-d]pyrimidin-2-amine;

N-(4-(2,4-dimethyloxazol-5-yl)-2-methoxyphenyl)-6-methyl-8-(1-oxa-6-azaspiro[3.3]heptan-6-yl)pyrido[3,4-d]pyrimidin-2-amine;

1-(2-((4-(2,4-dimethyloxazol-5-yl)-2-methoxyphenyl)amino)-6-methylpyrido[3,4-d]pyrimidin-8-yl)-3-methylazetidine-3-carbonitrile;

N2-(4-(2,4-dimethyloxazol-5-yl)-2-methoxyphenyl)-6-methyl-N8-((3-methyltetrahydrofuran-3-yl)methyl)pyrido[3,4-d]pyrimidine-2,8-diamine;

N-(4-(2,4-dimethyloxazol-5-yl)-2-methoxyphenyl)-6-methyl-8-(2-oxa-7-azaspiro[4.4]nonan-7-yl)pyrido[3,4-d]pyrimidin-2-amine;

N2-(4-(2,4-dimethyloxazol-5-yl)-2-methoxyphenyl)-6-methyl-N8-(tetrahydro-2H-pyran-4-yl)pyrido[3,4-d]pyrimidine-2,8-diamine;

N-(4-(2,4-dimethyloxazol-5-yl)-2-methoxyphenyl)-6-methyl-8-(7-oxa-2-azaspiro[3.5]nonan-2-yl)pyrido[3,4-d]pyrimidin-2-amine;

N2-(4-(2,4-dimethyloxazol-5-yl)-2-methoxyphenyl)-6-methyl-N8-neopentylpyrido[3,4-d]pyrimidine-2,8-diamine;

8-(3,3-dimethylazetidin-1-yl)-N-(4-(2,4-dimethyloxazol-5-yl)-2-ethoxyphenyl)-6-methylpyrido[3,4-d]pyrimidin-2-amine;

1-(2-((4-(2,4-dimethyloxazol-5-yl)-2-ethoxyphenyl)amino)-6-methylpyrido[3,4-d]pyrimidin-8-yl)-4-methylpiperidine-4-carbonitrile;

N-(4-(2,4-dimethyloxazol-5-yl)-2-ethoxyphenyl)-8-(3-methoxy-3-methylazetidin-1-yl)-6-methylpyrido[3,4-d]pyrimidin-2-amine;

N-(4-(2,4-dimethyloxazol-5-yl)-2-ethoxyphenyl)-8-(4-methoxypiperidin-1-yl)-6-methylpyrido[3,4-d]pyrimidin-2-amine;

N-(4-(2,4-dimethyloxazol-5-yl)-2-ethoxyphenyl)-8-(4-methoxy-4-methylpiperidin-1-yl)-6-methylpyrido[3,4-d]pyrimidin-2-amine;

N-(4-(2,4-dimethyloxazol-5-yl)-2-ethoxyphenyl)-6-methyl-8-(1-oxa-6-azaspiro[3.3]heptan-6-yl)pyrido[3,4-d]pyrimidin-2-amine;

1-(2-((4-(2,4-dimethyloxazol-5-yl)-2-ethoxyphenyl)amino)-6-methylpyrido[3,4-d]pyrimidin-8-yl)-3-methylazetidine-3-carbonitrile;

N2-(4-(2,4-dimethyloxazol-5-yl)-2-ethoxyphenyl)-6-methyl-N8-((3-methyltetrahydrofuran-3-yl)methyl)pyrido[3,4-d]pyrimidine-2,8-diamine;

N-(4-(2,4-dimethyloxazol-5-yl)-2-ethoxyphenyl)-6-methyl-8-(2-oxa-7-azaspiro[4.4]nonan-7-yl)pyrido[3,4-d]pyrimidin-2-amine;

N2-(4-(2,4-dimethyloxazol-5-yl)-2-ethoxyphenyl)-6-methyl-N8-(tetrahydro-2H-pyran-4-yl)pyrido[3,4-d]pyrimidine-2,8-diamine;

N-(4-(2,4-dimethyloxazol-5-yl)-2-ethoxyphenyl)-6-methyl-8-(7-oxa-2-azaspiro[3.5]nonan-2-yl)pyrido[3,4-d]pyrimidin-2-amine;

N2-(4-(2,4-dimethyloxazol-5-yl)-2-ethoxyphenyl)-6-methyl-N8-neopentylpyrido[3,4-d]pyrimidine-2,8-diamine;

8-(3,3-dimethylazetidin-1-yl)-N-(4-(2,5-dimethyloxazol-4-yl)-2-methoxyphenyl)-6-methylpyrido[3,4-d]pyrimidin-2-amine;

1-(2-((4-(2,5-dimethyloxazol-4-yl)-2-methoxyphenyl)amino)-6-methylpyrido[3,4-d]pyrimidin-8-yl)-4-methylpiperidine-4-carbonitrile;

N-(4-(2,5-dimethyloxazol-4-yl)-2-methoxyphenyl)-8-(3-methoxy-3-methylazetidin-1-yl)-6-methylpyrido[3,4-d]pyrimidin-2-amine;

N-(4-(2,5-dimethyloxazol-4-yl)-2-methoxyphenyl)-8-(4-methoxypiperidin-1-yl)-6-methylpyrido[3,4-d]pyrimidin-2-amine;

N-(4-(2,5-dimethyloxazol-4-yl)-2-methoxyphenyl)-8-(4-methoxy-4-methylpiperidin-1-yl)-6-methylpyrido[3,4-d]pyrimidin-2-amine;

N-(4-(2,5-dimethyloxazol-4-yl)-2-methoxyphenyl)-6-methyl-8-(1-oxa-6-azaspiro[3.3]heptan-6-yl)pyrido[3,4-d]pyrimidin-2-amine;

1-(2-((4-(2,5-dimethyloxazol-4-yl)-2-methoxyphenyl)amino)-6-methylpyrido[3,4-d]pyrimidin-8-yl)-3-methylazetidine-3-carbonitrile;

N2-(4-(2,5-dimethyloxazol-4-yl)-2-methoxyphenyl)-6-methyl-N8-((3-methyltetrahydrofuran-3-yl)methyl)pyrido[3,4-d]pyrimidine-2,8-diamine;

N-(4-(2,5-dimethyloxazol-4-yl)-2-methoxyphenyl)-6-methyl-8-(2-oxa-7-azaspiro[4.4]nonan-7-yl)pyrido[3,4-d]pyrimidin-2-amine;

N2-(4-(2,5-dimethyloxazol-4-yl)-2-methoxyphenyl)-6-methyl-N8-(tetrahydro-2H-pyran-4-yl)pyrido[3,4-d]pyrimidine-2,8-diamine;

N-(4-(2,5-dimethyloxazol-4-yl)-2-methoxyphenyl)-6-methyl-8-(7-oxa-2-azaspiro[3.5]nonan-2-yl)pyrido[3,4-d]pyrimidin-2-amine;

N2-(4-(2,5-dimethyloxazol-4-yl)-2-methoxyphenyl)-6-methyl-N8-neopentylpyrido[3,4-d]pyrimidine-2,8-diamine;

8-(3,3-dimethylazetidin-1-yl)-N-(4-(2,5-dimethyloxazol-4-yl)-2-ethoxyphenyl)-6-methylpyrido[3,4-d]pyrimidin-2-amine;

1-(2-((4-(2,5-dimethyloxazol-4-yl)-2-ethoxyphenyl)amino)-6-methylpyrido[3,4-d]pyrimidin-8-yl)-4-methylpiperidine-4-carbonitrile;

N-(4-(2,5-dimethyloxazol-4-yl)-2-ethoxyphenyl)-8-(3-methoxy-3-methylazetidin-1-yl)-6-methylpyrido[3,4-d]pyrimidin-2-amine;

N-(4-(2,5-dimethyloxazol-4-yl)-2-ethoxyphenyl)-8-(4-methoxypiperidin-1-yl)-6-methylpyrido[3,4-d]pyrimidin-2-amine;

N-(4-(2,5-dimethyloxazol-4-yl)-2-ethoxyphenyl)-8-(4-methoxy-4-methylpiperidin-1-yl)-6-methylpyrido[3,4-d]pyrimidin-2-amine;

N-(4-(2,5-dimethyloxazol-4-yl)-2-ethoxyphenyl)-6-methyl-8-(1-oxa-6-azaspiro[3.3]heptan-6-yl)pyrido[3,4-d]pyrimidin-2-amine;

1-(2-((4-(2,5-dimethyloxazol-4-yl)-2-ethoxyphenyl)amino)-6-methylpyrido[3,4-d]pyrimidin-8-yl)-3-methylazetidine-3-carbonitrile;

N2-(4-(2,5-dimethyloxazol-4-yl)-2-ethoxyphenyl)-6-methyl-N8-((3-methyltetrahydrofuran-3-yl)methyl)pyrido[3,4-d]pyrimidine-2,8-diamine;

N-(4-(2,5-dimethyloxazol-4-yl)-2-ethoxyphenyl)-6-methyl-8-(2-oxa-7-azaspiro[4.4]nonan-7-yl)pyrido[3,4-d]pyrimidin-2-amine;

N2-(4-(2,5-dimethyloxazol-4-yl)-2-ethoxyphenyl)-6-methyl-N8-(tetrahydro-2H-pyran-4-yl)pyrido[3,4-d]pyrimidine-2,8-diamine;

N-(4-(2,5-dimethyloxazol-4-yl)-2-ethoxyphenyl)-6-methyl-8-(7-oxa-2-azaspiro[3.5]nonan-2-yl)pyrido[3,4-d]pyrimidin-2-amine;

N2-(4-(2,5-dimethyloxazol-4-yl)-2-ethoxyphenyl)-6-methyl-N8-neopentylpyrido[3,4-d]pyrimidine-2,8-diamine, or pharmaceutically acceptable salts thereof.

In one embodiment of each aspect and embodiment herein, the MPS1 inhibitor is selected from the group consisting of NMS-P715, BAY 1217389, BAY 1161909 and N-cyclopropyl-4-(6-(2,3-difluoro-4-methoxyphenoxy)-8-((3,3,3-trifluoropropyl)amino)imidazo[1,2-b]pyridazin-3-yl)-2-methylbenzamide;

(R)-2-(4-fluorophenyl)-N-(4-(2-((2-methoxy-4-(methylsulfonyl)phenyl)amino)-[1,2,4]triazolo[1,5-a]pyridin-6-yl)phenyl)propanamide;

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

(S)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile;

N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof.

In one embodiment of each aspect and embodiment herein, the MPS1 inhibitor is selected from the group consisting of NMS-P715, BAY 1217389, BAY 1161909 and N2-(4-(4,5-dimethyl-4H-1,2,4-triazol-3-yl)-2-ethoxyphenyl)-6-methyl-N8-neopentylpyrido[3,4-d]pyrimidine-2,8-diamine;

(S)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile;

N2-(2-ethoxy-4-(4-methyl-4H-1,2,4-triazol-3-yl)phenyl)-6-methyl-N8-neopentylpyrido[3,4-d]pyrimidine-2,8-diamine;

or pharmaceutically acceptable salts thereof.

In one embodiment of each aspect and embodiment herein, the MPS1 inhibitor is selected from the group consisting of NMS-P715, BAY 1217389, BAY 1161909 and N2-(2-ethoxy-4-(4-methyl-4H-1,2,4-triazol-3-yl)phenyl)-6-methyl-N8-neopentylpyrido[3,4-d]pyrimidine-2,8-diamine, or pharmaceutically acceptable salts thereof.

In one embodiment of each aspect and embodiment herein, the MPS1 inhibitor is selected from the group consisting of:

N-cyclopropyl-4-(6-(2,3-difluoro-4-methoxyphenoxy)-8-((3,3,3-trifluoropropyl)amino)imidazo[1,2-b]pyridazin-3-yl)-2-methylbenzamide;

(R)-2-(4-fluorophenyl)-N-(4-(2-((2-methoxy-4-(methylsulfonyl)phenyl)amino)-[1,2,4]triazolo[1,5-a]pyridin-6-yl)phenyl)propanamide;

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

(S)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile;

N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof.

In one embodiment of each aspect and embodiment herein, the MPS1 inhibitor is selected from the group consisting of:

N-cyclopropyl-4-(6-(2,3-difluoro-4-methoxyphenoxy)-8-((3,3,3-trifluoropropyl)amino)imidazo[1,2-b]pyridazin-3-yl)-2-methylbenzamide; and (R)-2-(4-fluorophenyl)-N-(4-(2-((2-methoxy-4-(methylsulfonyl)phenyl)amino)-[1,2,4]triazolo[1,5-a]pyridin-6-yl)phenyl)propanamide;

or a pharmaceutically acceptable salt or solvate thereof.

In one embodiment of each aspect and embodiment herein, the MPS1 inhibitor is selected from the group consisting of:

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

(S)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile;

N2-(2-ethoxy-4-(4-methyl-4H-1,2,4-triazol-3-yl)phenyl)-6-methyl-N8-neopentylpyrido[3,4-d]pyrimidine-2,8-diamine;

or pharmaceutically acceptable salts thereof

In one embodiment of each aspect and embodiment herein, the MPS1 inhibitor is N2-(2-ethoxy-4-(4-methyl-4H-1,2,4-triazol-3-yl)phenyl)-6-methyl-N8-neopentylpyrido[3,4-d]pyrimidine-2,8-diamine, or pharmaceutically acceptable salts thereof.

Endocrine Therapy

In one embodiment of each of the aspects and embodiments herein, the endocrine therapy comprises/essentially consists of/consists of treatment with an endocrine agent.

In one embodiment of each of the aspects and embodiments herein, the endocrine agent is selected from one or more of an aromatase inhibitor, a selective oestrogen receptor modulator (SERM) and a selective oestrogen receptor degrader/downregulator (SERD).

In one embodiment of each of the aspects and embodiments herein, endocrine therapy comprises/essentially consists of/consists of separate, sequential or combined treatment with an aromatase inhibitor and a SERD.

In one embodiment of each of the aspects and embodiments herein, endocrine therapy comprises/essentially consists of/consists of separate, sequential or combined treatment with an aromatase inhibitor and a SERM.

In one embodiment of each of the aspects and embodiments herein, endocrine therapy comprises/essentially consists of/consists of separate, sequential or combined treatment with a SERM and a SERD.

In one embodiment of each of the aspects and embodiments herein, the SERM is selected from the group consisting of tamoxifen, afimoxifene, raloxifene, toremifene, bazedoxifene and lasofoxifene, or pharmaceutically acceptable salts or solvates thereof. Suitably, the SERM is selected from the group consisting of tamoxifen, raloxifene, toremifene, bazedoxifene and lasofoxifene, or pharmaceutically acceptable salts or solvates thereof. Suitably, the SERM is selected from the group consisting of tamoxifen, raloxifene and toremifene, or pharmaceutically acceptable salts or solvates thereof. Suitably, the SERM is selected from the group consisting of tamoxifen and toremifene, or pharmaceutically acceptable salts or solvates thereof. Suitably, the SERM is selected from the group consisting of tamoxifen and raloxifene, or pharmaceutically acceptable salts or solvates thereof. Suitably, the SERM is tamoxifen, or pharmaceutically acceptable salts or solvates thereof.

In one embodiment of each of the aspects and embodiments herein, the aromatase inhibitor is selected from the group consisting of anastrozole, exemestane, letrozole, fadrozole and formestane, or pharmaceutically acceptable salts or solvates thereof. Suitably, the aromatase inhibitor is selected from the group consisting of anastrozole, exemestane, letrozole and fadrozole, or pharmaceutically acceptable salts or solvates thereof. Suitably, the aromatase inhibitor is selected from the group consisting of anastrozole, exemestane, and letrozole, or pharmaceutically acceptable salts or solvates thereof. Suitably, the aromatase inhibitor is selected from the group consisting of anastrozole and letrozole, or pharmaceutically acceptable salts or solvates thereof. Suitably, the aromatase inhibitor is selected from the group consisting of anastrozole and exemestane, or pharmaceutically acceptable salts or solvates thereof. Suitably, the aromatase inhibitor is selected from the group consisting of exemestane and letrozole, or pharmaceutically acceptable salts or solvates thereof.

In one embodiment of each of the aspects and embodiments herein, the SERD is selected from the group consisting of fulvestrant, brilanestrant and elacestrant, or pharmaceutically acceptable salts or solvates thereof. Suitably, the SERD is selected from the group consisting of fulvestrant and elacestrant, or pharmaceutically acceptable salts or solvates thereof. Suitably, the SERD is selected from the group consisting of fulvestrant and brilanestrant, or pharmaceutically acceptable salts or solvates thereof. Suitably, the SERD is fulvestrant (ICI), or pharmaceutically acceptable salts or solvates thereof.

In one embodiment of each of the aspects and embodiments herein, the endocrine therapy comprises/essentially consists of/consists of separate, sequential or combined treatment with anastrozole and fulvestrant.

In one embodiment of each of the aspects and embodiments herein, the endocrine therapy comprises/essentially consists of/consists of separate, sequential or combined treatment with tamoxifen and fulvestrant.

Combinations

In one aspect, the present invention relates to a combination comprising an MPS1 inhibitor and a CDK4/6 inhibitor.

In one aspect, the present invention relates to a pharmaceutical product comprising an MPS1 inhibitor and a CDK4/6 inhibitor.

In one aspect, the present invention relates to a method for the treatment of oestrogen receptor positive breast cancer in a subject in need thereof comprising administering to said subject, either separately, sequentially or in combination, a therapeutically effective amount of an MPS1 inhibitor and a therapeutically effective amount of a CDK4/6 inhibitor.

In one aspect, the present invention relates to a pharmaceutical product comprising an MPS1 inhibitor and a CDK4/6 inhibitor for use in the treatment of an oestrogen receptor positive breast cancer, wherein the MPS1 inhibitor and the CDK4/6 inhibitor are for separate, sequential or combined administration.

In one aspect, the present invention relates to the use of a pharmaceutical product comprising an MPS1 inhibitor and a CDK4/6 inhibitor in the manufacture of a medicament for the treatment of oestrogen receptor positive breast cancer, wherein the MPS1 inhibitor and the CDK4/6 inhibitor are for separate, sequential or combined administration.

In one aspect, the present invention relates to an MPS1 inhibitor and a CDK4/6 inhibitor for use in the treatment of estrogen receptor-positive breast cancer.

In one aspect, the present invention relates to an MPS1 inhibitor for use in the treatment of estrogen receptor-positive breast cancer, wherein said MPS1 inhibitor is for separate, sequential or combined administration with a CDK4/6 inhibitor.

In one aspect, the present invention relates to a CDK4/6 inhibitor for use in the treatment of estrogen receptor-positive breast cancer, wherein said CDK4/6 inhibitor is for separate, sequential or combined administration with an MPS1 inhibitor.

In one aspect, the present invention relates to a use of an MPS1 inhibitor and a CDK4/6 inhibitor in the manufacture of a medicament for the treatment of estrogen receptor-positive breast cancer.

In one aspect, the present invention relates to a use of an MPS1 inhibitor in the manufacture of a medicament for the treatment of estrogen receptor-positive breast cancer, wherein said MPS1 inhibitor is for separate, sequential or combined administration with a CDK4/6 inhibitor.

In one aspect, the present invention relates to a use of a CDK4/6 inhibitor in the manufacture of a medicament for the treatment of estrogen receptor-positive breast cancer, wherein said CDK4/6 inhibitor is for separate, sequential or combined administration with an MPS1 inhibitor.

Suitably, the MPS1 inhibitor is as defined any of the above embodiments. Suitably, the CDK4/6 inhibitor is as defined in any the above embodiments.

In one embodiment, the MPS1 inhibitor is selected from:
N-cyclopropyl-4-(6-(2,3-difluoro-4-methoxyphenoxy)-8-((3,3,3-trifluoropropyl)amino)imidazo[1,2-b]pyridazin-3-yl)-2-methylbenzamide;
(R)-2-(4-fluorophenyl)-N-(4-(2-((2-methoxy-4-(methylsulfonyl)phenyl)amino)-[1,2,4]triazolo[1,5-a]pyridin-6-yl)phenyl)propanamide;
N2-(4-(4,5-dimethyl-4H-1,2,4-triazol-3-yl)-2-ethoxyphenyl)-6-methyl-N8-neopentylpyrido[3,4-d]pyrimidine-2,8-diamine;
(S)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;
8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;
N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;
1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile;
N2-(2-ethoxy-4-(4-methyl-4H-1,2,4-triazol-3-yl)phenyl)-6-methyl-N8-neopentylpyrido[3,4-d]pyrimidine-2,8-diamine;
or a pharmaceutically acceptable salt or solvate thereof, and the CDK4/6 inhibitor is selected from palbociclib, abemaciclib and ribociclib, or pharmaceutically acceptable salts or solvates thereof; suitably palbociclib or pharmaceutically acceptable salts or solvates thereof.

In one embodiment, the MPS1 inhibitor is selected from:
N2-(4-(4,5-dimethyl-4H-1,2,4-triazol-3-yl)-2-ethoxyphenyl)-6-methyl-N8-neopentylpyrido[3,4-d]pyrimidine-2,8-diamine;
(S)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;
8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;
N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;
1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile;
N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof, and the CDK4/6 inhibitor is selected from palbociclib, abemaciclib and ribociclib, or pharmaceutically acceptable salts or solvates thereof; suitably palbociclib or pharmaceutically acceptable salts or solvates thereof.

In one embodiment, the MPS1 inhibitor is selected from:
N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof, and the CDK4/6 inhibitor is selected from palbociclib, abemaciclib and ribociclib, or pharmaceutically acceptable salts or solvates thereof; suitably palbociclib or pharmaceutically acceptable salts or solvates thereof.

In one embodiment, the MPS1 inhibitor is selected from:
N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof, and the CDK4/6 inhibitor is selected from palbociclib, abemaciclib and ribociclib, or pharmaceutically acceptable salts or solvates thereof; suitably palbociclib or pharmaceutically acceptable salts or solvates thereof.

EXAMPLES

Materials and Methods

Palbociclib (PD-0332991) was synthesized and supplied by Pfizer (Tadworth, UK). MPS1 inhibitor: CCT289346 was synthesized and supplied by ICR Cancer Therapeutics (Sutton, UK); MPS1 inhibitor NMS-P715 was purchased from Calbiochem (Hertfordshire, UK).

Tissue Culture

ER+ BC lines, wild type (wt) MCF7 and wt-T47D cells were obtained from ATCC and cultured in phenol red-free RPMI 1640 medium (Gibco, Thermo Fisher Scientific, Loughborough, UK) supplemented with 10% fetal bovine serum (Gibco, Thermo Fisher Scientific) and 1 nM E2 at 37° C. in 5% $CO_2$. Cell lines identity was confirmed by short tandem repeat profiling (Promega, Madison, Wis., USA). Long-term-estrogen-deprived cells (MCF7-LTED$^{wt}$ ESR1) modelling resistance to an endocrine therapy were cultured in phenol red free RPMI 1640 supplemented with 10% dextran charcoal-stripped fetal bovine serum (DCC-FBS).

Cell Viability Assays

In order to assess effect of MPS1 inhibition on BC cells grown 2D, cells were seeded into white 96-well plates (Greiner Bio-One, Gloucestershire, UK) in RPMI 1640 supplemented with 10% DCC-FBS. Wt cells were stripped of E2 for 72 hrs prior to experiment. After 24 hrs cells were treated with escalating doses of MPS1 inhibitors±palbocliclib. Media was replaced after 3 days and cell viability was assessed after 6 days using the CellTitre-Glo® Luminescent Cell Viability Assay (Promega) according to manufacturer's instructions.

siRNA Kinome Library

A panel of palbociclib-resistant cell lines, including MCF7-991R, MCF7-LTED 991R, T47D-991R, T47D-LTED 991R and MCF7-LTED ICIR 991R was transfected with ON-TARGETplus siRNA Library-Human Protein Kinase (G-103505, GE Dharmacon, Buckinghamshire, UK). The siRNA library consisting of nine 96-well plates containing SMART pool siRNA targeting 709 protein kinases was transferred onto three 384 well plates white-walled with clear bottoms (Greiner Bio-One) using Hamilton Microlab Star liquid handling robot (Hamilton, Bonaduz, Switzerland). The library was supplemented with non-targeting siRNA and PLK1 siRNA (both SMART pools from GE Dharmacon), as positive and negative controls respectively and plates frozen.

For reverse transfection, the plates containing 200 nM of siRNA were defrosted, 10 µl of RNAiMax (Invitrogen, Paisley, UK) per well was added using Multidrop Combi (Thermo Fisher Scientific) and incubated for 30 min at room temperature. Next, cells were seeded in 35 µl of basal growth media per well using Multidrop Combi. After 6 days cells viability was assessed using CellTitre-Glo® Luminescent Cell Viability Assay (Promega) according to manufacturer's protocol and luminescence was measured using Victor spectrophotometer (Perkin Elmer, Wokingam. UK). The luminescence reading for each well of the plates was log transformed, centered to the plates median and then median of replicates was calculated. This was finally used to calculate Z score using median absolute deviation for a cell line. The dynamics of each library screen was assessed by calculating Z prime values. The threshold of acceptance was set as Z'>0.3 (Brough et al., 2011). Each screen consisted of at least two biological experiments, which included a technical replicate library. Venn diagram combining targets from different BC models was then generated using Venny 2.1.0 (Computational Genomics, CNB-CSIC, Spain).

Genomic Profiling Reveals Loss of RB is Associated with Irreversible Resistance to CDK4/6 Inhibition A panel of breast cancer cell lines (wt-MCF7, MCF7 LTED, wt-T47D and T47D LTED) with varying phenotypic backgrounds, were treated long-term in the presence of a CDK4/6 inhibitor (palbociclib, 1 µM). Resistance was authenticated by culturing the resistant cell lines with escalating concentrations of palbociclib in comparison with their wild-type progenitor (FIG. 1).

Subsequently, the palbociclib resistant cell lines were cultured short and long-term in the absence of drug to assess the stability of the resistant phenotype. Of note, "washout" of wt-MCF7$^{991R}$ and MCF7 LTED$^{991R}$ derivatives re-sensitised them to the antiproliferative effect of palbociclib suggesting the phenotype was plastic. In contrast, the wt-T47D$^{991R}$ and T47D LTED$^{991R}$ cell lines remained resistant (FIG. 1).

Targeting Resistance to Palbociclib

Figure 2:
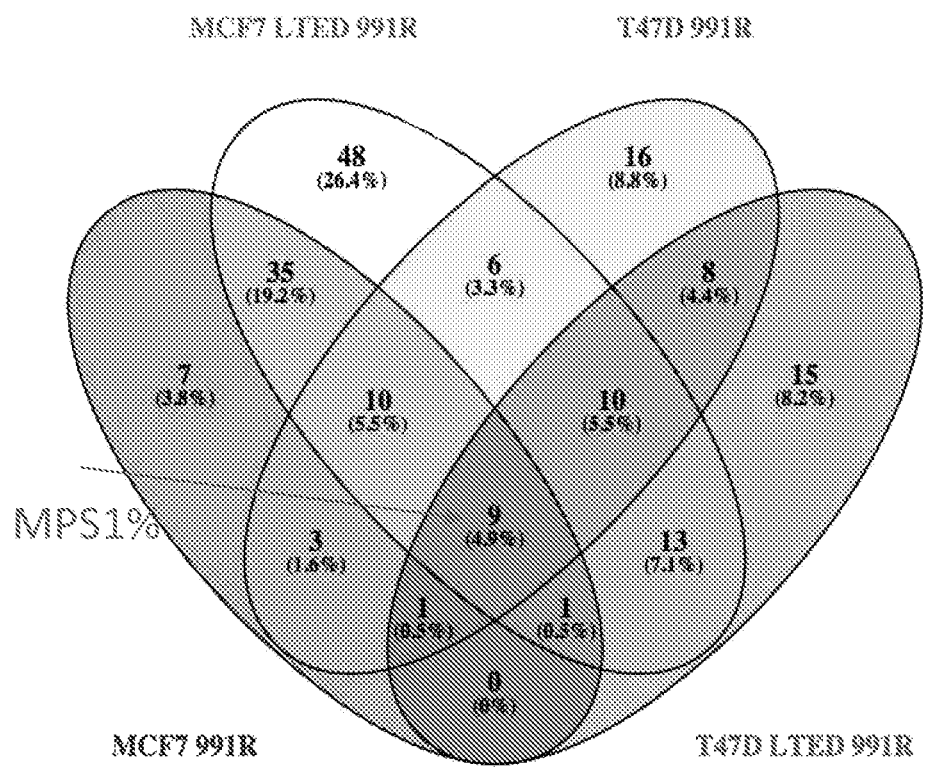
FIG. 2 shows the results of a kinome siRNA library screen in palbociclib resistant models. A. Venn diagram identified MPS1 as one of the common targets in all resistant models. B. Bar chart showing change in cell viability (mean±standard error of the mean) normalised to non-targeting siControl generated from library screens.
Figure 2:
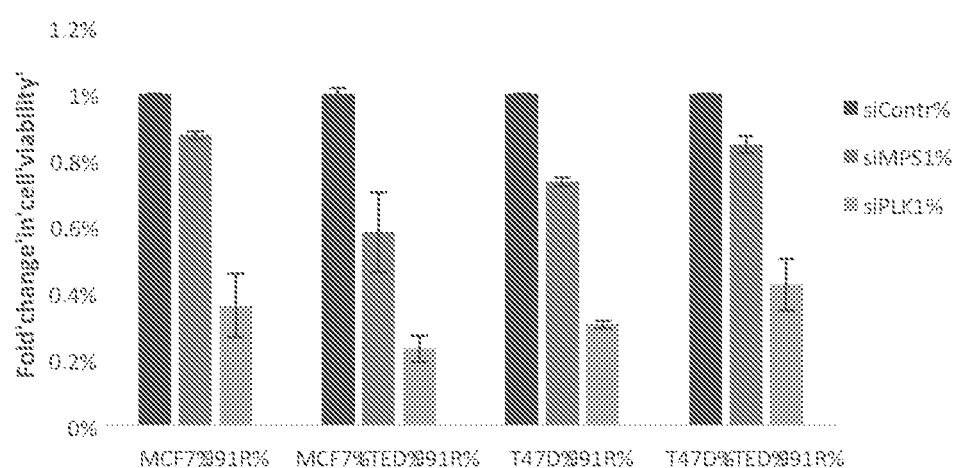

To investigate which kinases were commonly associated with the CDK4/6 resistant phenotype, a kinome knockdown screen (siRNA) targeting 709 kinases in the palbociclib resistant cell lines (FIG. 2) was used. All cell lines showed dependency on G2/M checkpoint regulators to varying degrees, however, MPS1 was a common determinant in all cell line models, irrespective of RB or ESR1 status. This observation was validated by comparing the effect of siRNA targeting MPS1 versus PLK in the cell lines. Inhibition varied between the cell lines with reduction in proliferation ranging between 20-40%.

Palbociclib Resistant Cell Lines are Sensitive to the Anti-Proliferative Effects of CCT289346

Figure 3:
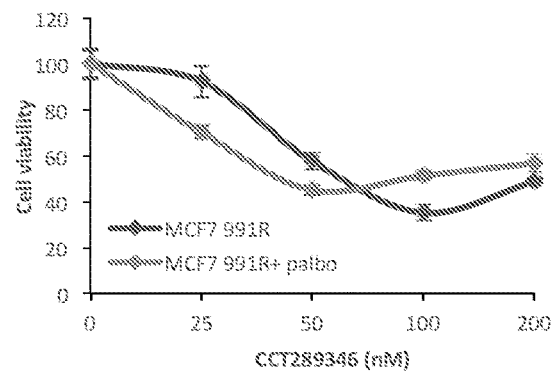
FIG. 3 shows wt-MCF7 and wt-T47D palbociclib-resistant cell lines were treated with escalating concentration of CCT289346 or NMS-P715 in the presence or absence of palbociclib for 6 days with a medium change on day 3. Cell viability was determined using TiterGlo and data expressed as fold cell viability.
Figure 3:
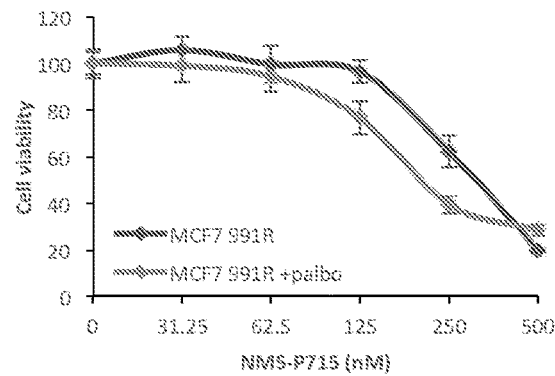
Figure 3:
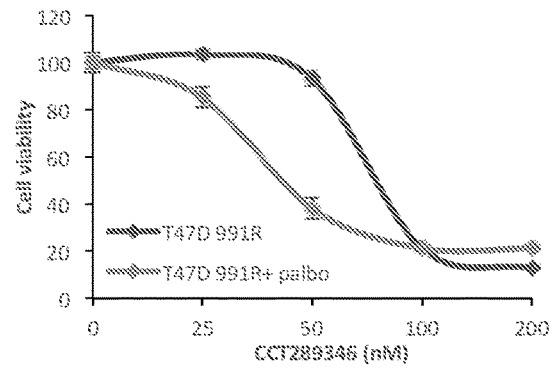
Figure 3:
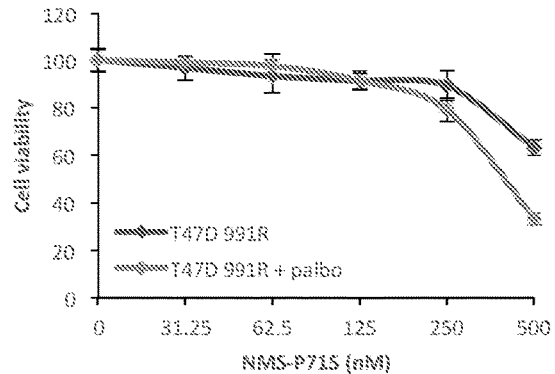
Figure 4:
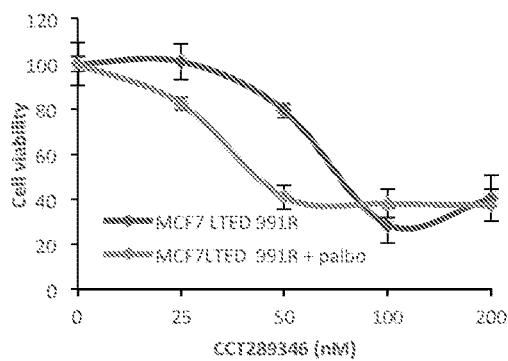
FIG. 4 shows MCF7-LTED and T47D-LTED palbociclib-resistant cell lines were treated with escalating concentration of CCT289346 or NMS-P715 in the presence or absence of palbociclib for 6 days with a medium change on day 3. Cell viability was determined using TiterGlo and data expressed as fold cell viability.
Figure 4:
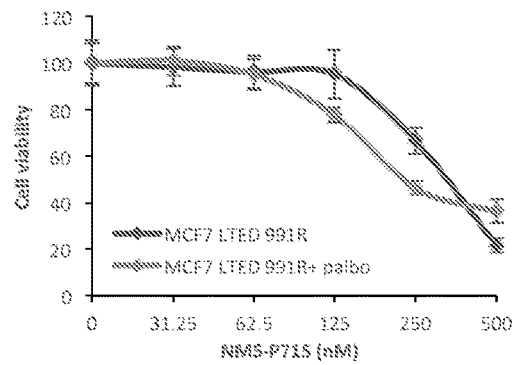
Figure 4:
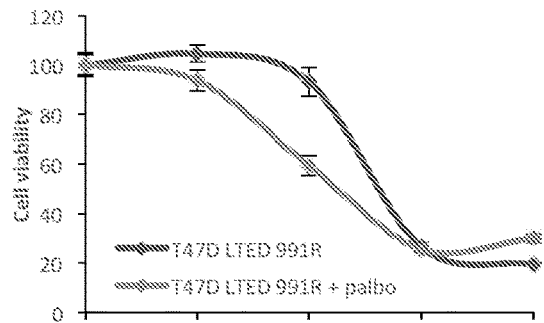
Figure 4:
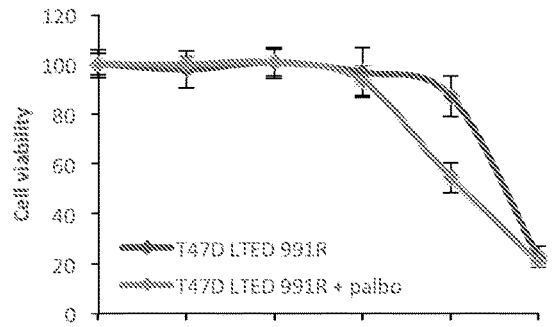

To address the validity of MPS1 as a common determinant of resistance to CDK4/6 inhibition, proliferation assays were performed using MPS1 inhibitors CCT289346 and NMS-P715 in the presence or absence of palbociclib in variety of breast cancer cell lines, including wild type (FIG. 3) and LTED cell lines (FIG. 4).

All cell lines showed a concentration dependent decrease in proliferation in response to both MPS1 inhibitors (FIGS. 3 and 4) to varying degrees. The addition of CCT289346 to palbociclib showed a synergistic/additive effect, reflected by the lower $IC_{50}$ values (c.50 nM for wt-MCF7$^{991R}$, MCF7 LTED$^{991R}$ and wt-T47D$^{991R}$). The T47D-LTED$^{991R}$ appeared the most sensitive to MPS1 inhibition with an $IC_{50}$ value of 25 nM.

To date MPS1 inhibitors have only been studied in triple negative breast cancer models in combination with chemotherapy. As demonstrated herein, MPS1 is also a suitable target in ER+ breast cancer models of resistance to CDK4/6 inhibitors. The data herein shows that MPS1 inhibitors reduce tumour cell growth in CDK4/6 inhibitor-resistant cancer models, and endocrine- and CDK4/6-resistant models of breast cancer. These findings are of significant clinical importance, at least in part because currently very little is known of suitable therapy for patients who relapse on CDK4/6 inhibitors.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

REFERENCES

Asghar U, Witkiewicz A K, Turner N C, Knudsen E S. The history and future of targeting cyclin-dependent kinases in cancer therapy. Nat Rev Drug Discov. 2015 February; 14(2):130-46.

Brough R, Frankum J R, Sims D, Mackay A, Mendes-Pereira A M, Bajrami I, et al. Functional viability profiles of breast cancer. Cancer discovery. 2011; 1:260-73.

Hanahan D, Weinberg R A. Hallmarks of cancer: the next generation. Cell. 2011; 144:646-74.

Ma C X, Reinert T, Chmielewska I, Ellis M J. Mechanisms of aromatase inhibitor resistance. Nat Rev Cancer. 2015 May; 15(5):261-75.

Musgrove E A, Caldon C E, Barraclough J, Stone A, Sutherland R L. Cyclin D as a therapeutic target in cancer. Nature reviews Cancer. 2011; 11:558-72.

The invention claimed is:

1. A method for the treatment of an oestrogen receptor positive breast cancer in a subject in need thereof comprising administering to said subject a therapeutically effective amount of a compound capable of inhibiting MPS1, wherein:
   (i) said subject has previously been treated with a CDK4/6 inhibitor; and/or
   (ii) said breast cancer is resistant to treatment with a CDK4/6 inhibitor.

2. A method according to claim 1, wherein the subject has failed treatment with the CDK4/6 inhibitor.

3. A method according to claim 1, wherein the subject has relapsed during or following treatment with the CDK4/6 inhibitor.

4. A method according to claim 1 wherein the subject has experienced disease progression during or following treatment with the CDK4/6 inhibitor.

5. A method according to claim 1, wherein the subject has developed a CDK4/6 inhibitor-resistant breast cancer during or following treatment with the CDK4/6 inhibitor.

6. A method according to claim 1, wherein the breast cancer is de novo resistant to treatment with a CDK4/6 inhibitor.

7. A method according to claim 1, wherein the CDK4/6 inhibitor is selected from palbociclib, abemaciclib and ribociclib, or pharmaceutically acceptable salts or solvates thereof.

8. A method according to claim 1, wherein the subject is pre-menopausal.

9. A method according to claim 1, wherein the subject is post-menopausal.

10. A method according to claim 1, wherein (i) the subject has additionally been previously treated with an endocrine therapy; and/or (ii) the breast cancer is additionally resistant to endocrine therapy.

11. A method according to claim 10, wherein the subject has failed treatment with the endocrine therapy.

12. A method according to claim 10, wherein the subject has relapsed during or following treatment with the endocrine therapy.

13. A method according to claim 10, wherein the subject has experienced disease progression during or following treatment with the endocrine therapy.

14. A method according to claim 10, wherein the subject has developed an endocrine therapy-resistant breast cancer during or following treatment with the endocrine therapy.

15. A method according to claim 10, wherein the breast cancer is de novo resistant to endocrine therapy.

16. A method according to claim 10, wherein the endocrine therapy comprises the administration of an endocrine agent.

17. A method according to claim 16, wherein the endocrine agent is selected from one or more of an aromatase inhibitor, a selective oestrogen receptor modulator (SERM) and a selective oestrogen receptor degrader/downregulator (SERD).

18. A method according to claim 10, wherein the endocrine therapy comprises separate, sequential or combined treatment with an aromatase inhibitor and a SERD.

19. A method according to claim 10, wherein the endocrine therapy comprises separate, sequential or combined treatment with a SERM and a SERD.

20. A method according to claim 17, wherein the aromatase inhibitor is selected from anastrozole, exemestane and letrozole, or pharmaceutically acceptable salts or solvates thereof.

21. A method according to claim 17, wherein the SERM is tamoxifen, or pharmaceutically acceptable salts or solvates thereof.

22. A method according to claim 17, wherein the SERD is fulvestrant, or pharmaceutically acceptable salts or solvates thereof.

23. A method according to claim 1, wherein the method further comprises administering to said subject a CDK4/6 inhibitor either separately, sequentially and/or combination with the compound capable of inhibiting MPS1.

24. A method according to claim 23, wherein the CDK4/6 inhibitor is selected from palbociclib, abemaciclib and ribociclib, or pharmaceutically acceptable salts or solvates thereof.

25. A method according to claim 23, wherein the CDK4/6 inhibitor is selected from palbociclib and ribociclib, or pharmaceutically acceptable salts or solvates thereof.

26. A method according to claim 1, wherein the compound capable of inhibiting MPS1 is an MPS1 inhibitor, suitably selected from NMS-P715, AZ3146, BAY 1217389, BAY 1161909, MPS1-IN-3, MPS1-IN-2, CFI-402257, CCT289346, a compound of formula I, a compound of formula II, a compound of formula III and a compound of formula IV, or a pharmaceutically acceptable salt or solvate thereof;

wherein formula I is:

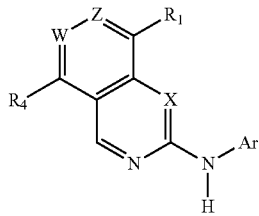

I wherein:
W is N or C—$R_3$;
X is CH or N;
Z is N or C—H;
$R_1$ is selected from chloro, (1-6C)alkyl, (1-8C)heteroalkyl, aryl, aryl(1-2C)alkyl, heteroaryl, heteroaryl(1-2C)alkyl, heterocyclyl, heterocyclyl(1-2C)alkyl, (3-8C)cycloalkyl, (3-8C)cycloalkyl(1-2C)alkyl, $NR_7R_8$, $OR_9$, $C(O)R_9$, $C(O)OR_9$, $OC(O)R_9$, $N(R_{10})OR_9$, $N(R_{10})C(O)OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SO_2R_9$, $N(R_{10})SOR_9$ or $SON(R_{10})R_9$;
and wherein $R_1$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_qCH_3$ (where q is 0, 1 or 2), methylamino or dimethylamino, aryl, aryl(1-2C)alkyl, heteroaryl, heteroaryl(1-2C)alkyl, heterocyclyl, heterocyclyl(1-2C)alkyl, (3-8C)cycloalkyl, or (3-8C)cycloalkyl(1-2C)alkyl,
and wherein any (1-4C)alkyl, (1-4C)alkoxy, aryl, heteroaryl, heterocyclyl, or (3-8C)cycloalkyl moiety present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR^a$, (where p is 0, 1 or 2), $SO_2N(R_b)R_a$, or $N(R_b)SO_2R^a$, wherein $R_a$ and $R_b$ are each independently selected from H or (1-4C)alkyl;
$R_3$ is hydrogen, (1-4C)alkyl, (3-6C)cycloalkyl, halo, $CF_3$, CN and (1-4C)alkoxy;
$R_4$ is hydrogen, (1-3C)alkyl, (1-3C)alkoxy, fluoro, chloro or $CF_3$;
Ar has the formula:

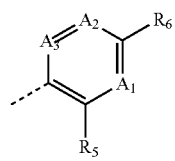

wherein:
all of $A_1$, $A_2$ and $A_3$ are CH;
one of $A_1$, $A_2$ and $A_3$ is N and the others are CH; or
two of $A_1$, $A_2$ and $A_3$ are N and the other is CH;
$R_5$ is selected from hydrogen, cyano, (1-3C)alkyl, (1-3C)fluoroalkyl, (1-3C)alkoxy, (1-3C)fluoroalkoxy, halo, (1-3C)alkanoyl, $C(O)NR_{15}R_{16}$ or $S(O)_2NR_{15}R_{16}$, and wherein $R_{15}$ and $R_{16}$ are each independently selected from H or (1-3C)alkyl,
and wherein any alkyl or alkoxy moieties present within a $R_5$ substituent group are optionally further by hydroxy or methoxy;
$R_6$ is selected from halo, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl,
or $R_6$ is a group of the formula:

$-L^1-L^2-R_{17}$ wherein
$L^1$ is absent or a linker group of the formula —$[CR_{18}R_{19}]_n$— in which n is an integer selected from 1, 2, 3 or 4, and $R_{18}$ and $R_{19}$ are each independently selected from hydrogen or (1-2C)alkyl;
$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{21})SO_2$, wherein $R_{20}$ and $R_{21}$ are each independently selected from hydrogen or (1-2C)alkyl; and
$R_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl,
and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);

or $R_{17}$ is a group having the formula:

-L³-L⁴-R₂₄

$L^3$ is absent or a linker group of the formula —$[CR_{25}R_{26}]_n$— in which n is an integer selected from 1, 2, 3 or 4, and $R_{25}$ and $R_{26}$ are each independently selected from hydrogen or (1-2C)alkyl;

$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl;

$R_8$ and $R_9$ are each independently selected from hydrogen, (1-6C)alkyl, (1-6C)alkoxy, (3-9C)cycloalkyl, (3-9C)cycloalkyl-(1-2C)alkyl, aryl, aryl-(1-2C)alkyl, heterocyclyl, heterocyclyl-(1-2C)alkyl, heteroaryl, heteroaryl-(1-2C)alkyl, and wherein $R_8$ and $R_9$ are optionally further substituted by one or more substituents selected from hydroxy, fluoro, chloro, cyano, $CF_3$, $OCF_3$ (1-2C)alkyl or (1-2C)alkoxy;

$R_7$ and $R_{10}$ are independently selected from hydrogen, (1-6C)alkyl, (3-6C)cycloalkyl, (3-6C)cycloalkyl-(1-2C)alkyl, and wherein $R_7$ and $R_{10}$ are optionally further substituted by one or more substituents selected from hydroxy, fluoro, chloro, cyano, $CF_3$, $OCF_3$, (1-2C)alkyl or (1-2C)alkoxy;

subject to the proviso that:
X is only N when Z is N;
W is only N when X and Z are both N; and
$R_6$ is not methoxy when $R_1$ is $S(O)_2R_9$ and $R_9$ is heterocyclyl;

wherein formula II is:

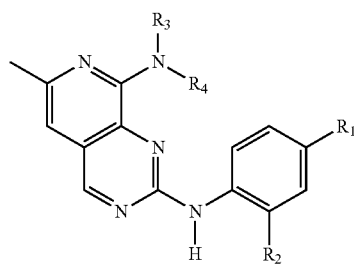

wherein:
$R_1$ is selected from:
a 5- or 6-membered heteroaryl optionally substituted with one or more substituents independently selected from halo, trifluoromethyl, difluoromethyl, trifluoromethoxy, difluoromethoxy, cyano, nitro, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_qR_c$ (where q is 0, 1 or 2), $SO_2N(R_d)R_c$, or $N(R_d)SO_2R_c$, wherein $R_c$ and $R_d$ are each independently selected from H or (1-4C)alkyl; or wherein the 5- or 6-membered heteroaryl is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-4C)alkyl, $NR_kR_l$, $OR_k$, $C(O)R_k$, $C(O)OR_k$, $OC(O)R_k$, $N(R_l)OR_k$, $C(O)N(R_l)R_k$, $N(R_l)C(O)R_k$, $S(O)_pR_k$ (where p is 0, 1 or 2), $SO_2N(R_k)R_l$, or $N(R_k)SO_2R_l$, wherein $R_k$ and $R_l$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_mR_n$, $OR_m$, $C(O)R_m$, $C(O)OR_m$, $OC(O)R_m$, $N(R_n)OR_m$, $C(O)N(R_n)R_m$, $N(R_n)C(O)R_m$, $S(O)_qR_m$ (where q is 0, 1 or 2), $SO_2N(R_n)R_m$, or $N(R_n)SO_2R_m$, wherein $R_m$ and $R_n$ are each independently selected from H or (1-4C)alkyl; or a group —$C(O)N(R_f)R_e$— or —$S(O)_2N(R_f)R_e$—;

wherein $R_e$ and $R_f$ are each independently selected from H or (1-4C)alkyl which is optionally substituted by halo or (1-2C)alkoxy;

or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-4C)alkyl, $NR_gR_h$, $OR_g$, $C(O)R_g$, $C(O)OR_g$, $OC(O)R_g$, $N(R_h)OR_g$, $C(O)N(R_h)R_g$, $N(R_h)C(O)R_g$, $S(O)_pR_h$ (where p is 0, 1 or 2), $SO_2N(R_h)R_g$, or $N(R_h)SO_2R_g$, wherein $R_g$ and $R_h$ are each independently selected from H or (1-4C)alkyl;

$R_2$ is selected from hydrogen, fluoro, chloro, (1-3C)alkoxy or (1-3C)fluoroalkoxy;

and either:
$R_3$ is selected from hydrogen or (1-3C)alkyl and $R_4$ is selected from (1-6C)alkyl, (3-9C)cycloalkyl, (3-9C)cycloalkyl-(1-4C)alkyl, aryl, aryl-(1-4C)alkyl, heterocyclyl, heterocyclyl-(1-4C)alkyl, heteroaryl, heteroaryl-(1-4C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$, $OR_o$, $C(O)R_o$, $C(O)OR_p$, $OC(O)R_o$, $N(R_p)OR_o$, $C(O)N(R_p)R_o$, $N(R_p)C(O)R_o$, S(O)$_p$R$_o$ (where p is 0, 1 or 2), SO$_2$N(R$_p$)R$_o$, or N(R$_p$)SO$_2$R$_o$ or (3-6C)cycloalkyl, (3-6C)cycloalkyl-(1-2C)alkyl, a 4, 5 or 6-membered heterocyclyl, a 4, 5 or 6-membered heterocyclyl-(1-2C)alkyl, wherein R$_o$ and R$_p$ are each independently selected from H or (1-4C)alkyl, (3-6C)cycloalkyl or (3-6C)cycloalkyl-(1-4C)alkyl; or R$_3$ and R$_4$ are linked such that, together with the nitrogen atom to which they are attached, they form a nitrogen-linked 4-, 5-6- or 7-membered heterocyclic ring, wherein said ring is optionally fused to a further 3-, 4-, 5- or 6-membered ring carbocyclic or heterocyclic ring, a 5- or 6-membered heteroaryl ring or a phenyl ring to form a bi-cyclic heterocyclic system, or linked through a spiro carbon atom to a further 4-, 5- or 6-membered ring carbocyclic or heterocyclic ring to form a spiro bicyclic ring system;

and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, NR$_i$R$_j$, OR$_i$, C(O)R$_i$, C(O)OR$_i$, OC(O)R$_i$, N(R$_j$)OR$_i$, C(O)N(R$_j$)R$_i$, N(R$_j$)C(O)R$_i$, S(O)$_q$R$_i$ (where q is 0, 1 or 2), SO$_2$N(R$_j$)R$_i$, or N(R$_j$)SO$_2$R$_i$, wherein R$_i$ and R$_j$ are each independently selected from H or (1-4C)alkyl;

with the proviso that said compound is not one of the following:

N2-(2-methoxy-4-(1-methyl-1H-pyrazol-4-yl)phenyl)-6-methyl-N8-neopentylpyrido[3,4-d]pyrimidine-2,8-diamine;

N2-(4-(1,2-dimethyl-1H-imidazol-5-yl)-2-methoxyphenyl)-N8-(2-methoxy-2-methylpropyl)-6-methylpyrido[3,4-d]pyrimidine-2,8-diamine;

N2-(4-(1,2-dimethyl-1H-imidazol-5-yl)-2-methoxyphenyl)-6-methyl-N8-neopentylpyrido[3,4-d]pyrimidine-2,8-diamine;

N2-(2-methoxy-4-(4-methyl-4H-1,2,4-triazol-3-yl)phenyl)-6-methyl-N8-neopentylpyrido[3,4-d]pyrimidine-2,8-diamine;

N8-(2-methoxy-2-methylpropyl)-N2-(2-methoxy-4-(4-methyl-4H-1,2,4-triazol-3-yl)phenyl)-6-methylpyrido[3,4-d]pyrimidine-2,8-diamine;

N2-(2-methoxy-4-(1-(2-methoxyethyl)-2-methyl-1H-imidazol-5-yl)phenyl)-6-methyl-N8-neopentylpyrido[3,4-d]pyrimidine-2,8-diamine;

N2-(2-ethoxy-4-(4-methyl-4H-1,2,4-triazol-3-yl)phenyl)-6-methyl-N8-neopentylpyrido[3,4-d]pyrimidine-2,8-diamine;

N2-(2-methoxy-4-(4-(methylsulfonyl)piperazin-1-yl)phenyl)-6-methyl-N8-neopentylpyrido[3,4-d]pyrimidine-2,8-diamine;

N2-(4-(1,3-dimethyl-1H-pyrazol-4-yl)-2-methoxyphenyl)-N8-(2-methoxy-2-methylpropyl)-6-methylpyrido[3,4-d]pyrimidine-2,8-diamine;

N-(2-ethoxy-4-(4-methyl-4H-1,2,4-triazol-3-yl)phenyl)-6-methyl-8-(6-oxa-2-azaspiro[3.4]octan-2-yl)pyrido[3,4-d]pyrimidin-2-amine;

N8-(2-methoxy-2-methylpropyl)-N2-(2-methoxy-4-(1-methyl-1H-1,2,4-triazol-5-yl)phenyl)-6-methylpyrido[3,4-d]pyrimidine-2,8-diamine;

N2-(2-(difluoromethoxy)-4-(1-methyl-1H-pyrazol-4-yl)phenyl)-N8-(2-methoxy-2-methylpropyl)-6-methylpyrido[3,4-d]pyrimidine-2,8-diamine; and (4-(3-methoxy-4-((8-((2-methoxy-2-methylpropyl)amino)-6-methylpyrido[3,4-d]pyrimidin-2-yl)amino)phenyl)-1-methyl-1H-pyrazol-5-yl)methanol;

wherein formula III is

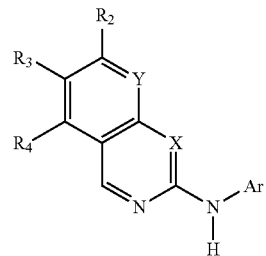

wherein:

X is CH or N;

Y is N or C—H;

R$_2$ is selected from (1-6C)alkyl, (1-8C)heteroalkyl, aryl, aryl(1-2C)alkyl, a 5 or 6 membered heteroaryl, a 5 or 6 membered heteroaryl(1-2C)alkyl, a 3 to 6 membered heterocyclyl, a 3 to membered heterocyclyl(1-2C)alkyl, (3-8C)cycloalkyl, (3-8C)cycloalkyl(1-2C)alkyl, NR$_{11}$R$_{12}$, OR$_{13}$, C(O)R$_{13}$, C(O)OR$_{13}$, OC(O)R$_{13}$, N(R$_{14}$)OR$_{13}$, N(R$_{14}$)C(O)OR$_{13}$, C(O)N(R$_{14}$)R$_{13}$, N(R$_{14}$)C(O)R$_{13}$, S(O)$_x$R$_{13}$ (where x is 0, 1 or 2), SO$_2$N(R$_{14}$)R$_{13}$, or N(R$_{14}$)SO$_2$R$_{13}$;

and wherein R$_2$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, S(O)$_x$CH$_3$ (where x is 0, 1 or 2), methylamino or dimethylamino, aryl, aryl(1-2C)alkyl, heteroaryl, heteroaryl(1-2C)alkyl, heterocyclyl, heterocyclyl(1-2C)alkyl, (3-8C)cycloalkyl, or (3-8C)cycloalkyl(1-2C)alkyl, and wherein any (1-4C)alkyl, (1-4C)alkoxy, aryl, heteroaryl, heterocyclyl, or (3-8C)cycloalkyl moiety present within a substituent group on R$_2$ is optionally further substituted by fluoro, chloro, trifluoromethyl, trifluoromethoxy, cyano, nitro, hydroxy, amino, carboxy, carbamoyl, sulphamoyl, (1-4C)alkyl, NR$_c$R$_d$, OR$_c$, C(O)R$_c$, C(O)OR$_c$, OC(O)R$_c$, N(R$_d$)OR$_c$, C(O)N(R$_d$)R$_c$, N(R$_d$)C(O)R$_c$, S(O)$_y$R$_c$ (where y is 0, 1 or 2), SO$_2$N(R$_d$)R$_c$, or N(R$_d$)SO$_2$R$_c$, wherein R$_E$ and R$_d$ are each independently selected from H or (1-4C)alkyl;

R$_3$ is hydrogen, (1-4C)alkyl, (3-6C)cycloalkyl, halo, CF$_3$, CN and (1-4C)alkoxy;

R$_4$ is hydrogen, (1-3C)alkyl, fluoro, chloro or CF$_3$;

Ar has the formula:

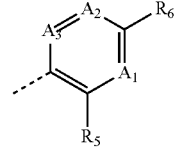

wherein:

all of A$_1$, A$_2$ and A$_3$ are CH; or

A$_3$ is CH and Ai or A$_2$ are selected from N or CH;

R$_5$ is hydrogen, cyano, (1-3C)alkyl, (1-3C)fluoroalkyl, (1-3C)alkoxy, (1-3C)fluoroalkoxy, halo, (1-3C)alkanoyl, C(O)NR$_{15}$R$_{16}$ or S(O)$_2$NR$_{15}$R$_{16}$, and wherein R$_{15}$ and R$_{16}$ are each independently selected from H or (1-3C)alkyl, and wherein any alkyl or alkoxy moieties present within a $R_5$ substituent group are optionally further substituted by hydroxy or methoxy;

$R_6$ is halogeno, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or $R_6$ is a group of the formula:

-L¹L²R₁₇ wherein $L^1$ is absent or a linker group of the formula —[$CR_{18}R_{19}$]$_n$— in which n is an integer selected from 1, 2, 3 or 4, and $R_{18}$ and $R_{19}$ are each independently selected from hydrogen or (1-2C)alkyl;

$L^2$ is absent or is selected from O, S, SO, SO₂, N($R_{20}$), C(O), C(O)O, OC(O), CH(O$R_{20}$), C(O)N($R_{20}$), N($R_{20}$) C(O), N($R_{20}$)C(O)N($R_{21}$), S(O)₂N($R_{20}$), or N($R_{21}$) SO₂, wherein $R_{20}$ and $R_{21}$ are each independently selected from hydrogen or (1-2C)alkyl; and $R_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_{17}$ is optionally further substituted by one or more substituent groups independently selected from oxo, halo, cyano, nitro, hydroxy, $NR_{22}R_{23}$, (1-4C) alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, CON$R_{22}R_{23}$, and SO₂N$R_{22}R_{23}$; wherein $R_{22}$ and $R_{23}$ are each independently selected from hydrogen, (1-4C)alkyl or (3-6C) cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring ring;

and wherein when said substituent group comprises an alkyl, cycloalkyl, heterocyclyl or heteroaryl moiety then said moiety is optionally further substituted by hydroxy, fluoro, chloro, cyano, CF₃, OCF₃, (1-2C) alkyl, (1-2C)alkoxy, SO₂(1-2C)alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);

or $R_{17}$ is a group having the formula:

-L³-L⁴-R₂₄ wherein $L^3$ is absent or a linker group of the formula —[$CR_{25}R_{26}$]$_n$— in which n is an integer selected from 1, 2, 3 or 4, and $R_{25}$ and $R_{26}$ are each independently selected from hydrogen or (1-2C)alkyl;

$L^4$ is absent or is selected from O, S, SO, SO₂, N($R_{27}$), C(O), C(O)O, OC(O), CH(O$R_{27}$), C(O)N($R_{27}$), N($R_{27}$) C(O), N($R_{27}$)C(O)N($R_{28}$), S(O)₂N($R_{27}$), or N($R_{28}$) SO₂, wherein $R_{27}$ and $R_{28}$ are each independently selected from hydrogen or (1-2C)alkyl; and $R_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C) alkyl;

$R_{12}$ is selected from hydrogen, (1-6C)alkyl, (1-6C)alkoxy, (3-6C)cycloalkyl, (3-6C)cycloalkyl-(1-2C)alkyl, aryl, aryl-(1-2C)alkyl, heterocyclyl, heterocyclyl-(1-2C)alkyl, heteroaryl, heteroaryl-(1-2C)alkyl, and wherein $R_{12}$ is optionally further substituted by one or more substituents selected from hydroxy, fluoro, chloro, cyano, CF₃, OCF₃ (1-2C)alkyl or (1-2C)alkoxy;

$R_{13}$ is selected from hydrogen, (1-6C)alkyl, (1-6C)alkoxy, (3-6C)cycloalkyl, (3-6C)cycloalkyl-(1-2C)alkyl, aryl, aryl-(1-2C)alkyl, heteroaryl, heteroaryl-(1-2C)alkyl, and wherein $R_n$ is optionally further substituted by one or more substituents selected from hydroxy, fluoro, chloro, cyano, CF₃, OCF₃ (1-2C)alkyl or (1-2C)alkoxy;

$R_{11}$ and $R_{10}$ are independently selected from hydrogen, (1-6C)alkyl, (3-6C)cycloalkyl, (3-6C)cycloalkyl-(1-2C)alkyl, and wherein $R_{11}$ and $R_{14}$ are optionally further substituted by one or more substituents selected from hydroxy, fluoro, chloro, cyano, CF₃, OCF₃, (1-2C)alkyl or (1-2C)alkoxy;

subject to the proviso that:

X can only be N when Y is N; and when X and Y are both N, $R_3$ is selected from H or fluoro and $R_2$ is not a $NR_{11}R_{12}$ group;

wherein formula IV is:

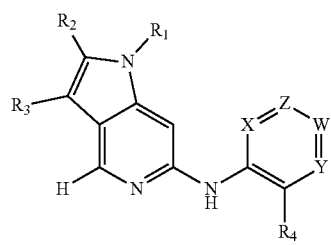

Formula IV wherein:

$R_1$ is hydrogen, (1-5C)alkyl, (1-5C)fluoroalkyl, (3-8C) cycloalkyl, (3-8C)cycloalkyl-(1-4C)alkyl, aryl, aryl-(1-4C)alkyl, heteroaryl, heteroaryl-(1-4C)alkyl, —S(O)₂—$R^a$, —C(O)—$R^a$, or —C(O)—O—$R^a$, wherein $R^a$ is (1-5C)alkyl, (3-8C)cycloalkyl, (3-8C) cycloalkyl-(1-4C)alkyl, aryl, aryl-(1-4C)alkyl, heteroaryl or heteroaryl-(1-4C)alkyl, and wherein any (1-5C)alkyl, (3-8C)cycloalkyl, (3-8C)cycloalkyl-(1-4C)alkyl, aryl, aryl-(1-4C)alkyl, heteroaryl, heteroaryl-(1-4C)alkyl group present in a Ru substituent group is optionally substituted by methyl, trifluoromethyl, methoxy, trifluoromethoxy, halo, cyano, nitro, hydroxy, mercapto, amino, carboxy, carbamoyl, or sulphamoyl;

$R_2$ is an aryl, aryl(1-2C)alkyl, 5- or 6-membered heteroaryl or a 5- or 6-membered heteroaryl(1-2C)alkyl, wherein $R_2$ is optionally substituted by one or more substituents selected from halogeno, trifluoromethyl, trifluoromethoxy, cyano, nitro, hydroxy, mercapto, amino, carboxy, carbamoyl, sulphamoyl, or a group of the formula:

L-L⁰-$R^b$ wherein

L is absent or a linker group of the formula [$CR_gR_h$]$_n$— in which n is an integer selected from 1, 2, 3 or 4, and $R_g$ and $R_h$ are each independently selected from hydrogen or (1-2C)alkyl;

$L^0$ is absent or is selected from O, S, SO, SO₂, N($R^c$), C(O), C(O)O, OC(O), CH(O$R^c$), C(O)N($R^c$), N($R^c$)C (O), N($R^c$)C(O)N($R^d$), SO₂N($R^c$), or N($R^c$)SO₂, wherein RC and $R^d$ are each independently selected from hydrogen or (1-2C)alkyl; and $R^b$ is (1-4C)alkyl, aryl, aryl-(1-4C)alkyl, (3-6C)cycloalkyl, (3-6C)cycloalkyl-(1-4C)alkyl, heteroaryl, heteroaryl-(1-4C)alkyl, heterocyclyl, or heterocyclyl-(1-4C)alkyl;

and wherein $R^b$ is optionally further substituted by one or more substituents independently selected from oxo, halogeno, cyano, nitro, hydroxy, $NR^eR^f$, (1-5C)alkyl, (1-5C)alkoxy, (1-5C)alkanoyl, (1-5C)sulphonyl or aryl; and wherein Re and $R^f$ are each independently selected from hydrogen or (1-4C)alkyl or (3-6C)cycloalkyl-(1-4C)alkyl; or Re and $R^f$ can be linked such that, together with the nitrogen atom to which they are attached, they form a 4-7 membered heterocyclic, heteroaryl or carbocyclic ring;

$R_3$ is H, (1-3C)alkyl, halogeno or $CF_3$;

$R_4$ is cyano, (1-3C)alkyl, (1-3C)fluoroalkyl, (1-3C)alkoxy, (1-3C)perfluoroalkoxy, halo, (1-3C)alkanoyl, $C(O)NR^iR^j$, or $S(O)_2NR^iR^j$; wherein $R^i$ and $R^j$ are each independently selected from H or (1-3C)alkyl;

X is CH or $CR_5$;

W, Y and Z are each independently selected from N, CH, or $CR_5$;

$R_5$ is halogeno, trifluoromethyl, trifluoromethoxy, cyano, nitro, hydroxy, mercapto, amino, carboxy, carbamoyl, sulphamoyl, ureido, (1-6C)alkyl, (2-6C)alkenyl, (2-6C)alkynyl, or $R_5$ is a group of the formula:

-$L^1$-$L^2$-$R_7$ wherein $L^1$ is absent or a linker group of the formula $[CR_8R_9]_n$— in which n is an integer selected from 1, 2, 3 or 4, and $R_8$ and $R_9$ are each independently selected from hydrogen or (1-2C)alkyl;

$L^2$ is absent or is selected from O, S, SO, $SO_2$, $N(R_{10})$, C(O), C(O)O, OC(O), $CH(OR_{10})$, $C(O)N(R_{10})$, $N(R_{10})C(O)$, $N(R_{10})C(O)N(R_{11})$, $S(O)_2N(R_{10})$, or $N(R_{13})SO_2$, wherein $R_{10}$ and $R_{11}$ are each independently selected from hydrogen or (1-2C)alkyl; and $R_7$ is (1-6C)alkyl, aryl, aryl-(1-6C)alkyl, (3-6C)cycloalkyl, (3-6C)cycloalkyl-(1-6C)alkyl, heteroaryl, heteroaryl-(1-6C)alkyl, heterocyclyl, heterocyclyl-(1-6C)alkyl, and wherein $R_7$ is optionally further substituted by one or more substituents independently selected from hydrogen, oxo, halogeno, cyano, nitro, hydroxy, $NR_{12}R_{13}$, (1-4C)alkoxy, (1-5C)alkyl, (3-8C)cycloalkyl, (3-8C)cyclo alkyl-(1-5C)alkyl, aryl, aryl-(1-5C)alkyl, (1-5C)alkanoyl, (1-5C)alkylsulphonyl, heterocyclyl, heterocyclyl-(1-5C)alkyl, heteroaryl, heteroaryl-(1-5C)alkyl, $CONR_{12}R_{13}$ and $SO_2NR_{12}R_{13}$;

$R_{12}$ and $R_{13}$ are each independently selected from hydrogen or (1-2C)alkyl; or $R_{12}$ and $R_{13}$ can be linked such that, together with the nitrogen atom to which they are attached, they form a 4-7 membered heterocyclic or heteroaryl ring;

or either W and Z, W and Y or Z and X are both $CR_5$ and the $R_5$ groups on the adjacent carbon atoms are linked such that, together with the carbon atoms to which they are attached, they form a fused 4-7 membered heterocyclic, heteroaryl or carbocyclic ring.

27. A method according to claim 26, wherein the MPS1 inhibitor is selected from NMS-P715, BAY 1217389, BAY 1161909, CCT289346, a compound of formula I, a compound of formula II, a compound of formula III and a compound of formula IV, or pharmaceutically acceptable salts or solvates thereof.

28. A method according to claim 26, wherein the MPS1 inhibitor is selected from a compound of formula I, a compound of formula II, a compound of formula III and a compound of formula IV, or pharmaceutically acceptable salts or solvates thereof.

29. A method according to claim 26, wherein the MPS1 inhibitor is selected from a compound of formula I and a compound of formula II, or pharmaceutically acceptable salts or solvates thereof.

30. A method according to claim 1, wherein the MPS1 inhibitor is selected from the following:

5-(furan-2-yl)-N-(4-methoxyphenyl)isoquinolin-3-amine;

N-(4-methoxyphenyl)-5-(1-methyl-1H-pyrazol-4-yl)isoquinolin-3-amine;

N-(2-methoxy-4-(1-methylpiperidin-4-yl)oxy)phenyl)-5-(1-methyl-1H-pyrazol-4-yl)isoquinolin-3-amine;

N-(2,4-dimethoxyphenyl)-5-(1-methyl-1H-pyrazol-4-yl)isoquinolin-3-amine;

3-chloro-N,N-dimethyl-4-((5-(1-methyl-1H-pyrazol-4-yl)isoquinolin-3-yl)amino)benzamide;

3-methoxy-N,N-dimethyl-4-((5-(1-methyl-1H-pyrazol-4-yl)isoquinolin-3-yl)amino)benzamide;

(3-methoxy-4-((5-(1-methyl-1H-pyrazol-4-yl)isoquinolin-3-yl)amino)phenyl)(3-methoxyazetidin-1-yl)methanone;

N-(2-chloro-4-(1-methyl-1H-pyrazol-4-yl)phenyl)-5-(1-methyl-1H-pyrazol-4-yl)isoquinolin-3-amine;

(3-chloro-4-((5-(1-methyl-1H-pyrazol-4-yl)isoquinolin-3-yl)amino)phenyl)(3-methoxyazetidin-1-yl)methanone;

(3-methoxy-4-((5-(pyridin-3-yl)isoquinolin-3-yl)amino)phenyl)(3-methoxy azetidin-1-yl)methanone;

N-(4-(3,5-dimethylisoxazol-4-yl)-2-methoxyphenyl)-5-(1-methyl-1H-pyrazol-4-yl)isoquinolin-3-amine;

(3-methoxy-4-(8-(1-methyl-1H-pyrazol-4-yl)pyrido[3,4-d]pyrimidin-2-yl)amino)phenyl)(3-methoxyazetidin-1-yl)methanone;

N-(2-methoxy-4-(1-methyl-1H-pyrazol-4-yl)phenyl)-8-(1-methyl-1H-pyrazol-4-yl)pyrido[3,4-d]pyrimidin-2-amine;

N-(2-chloro-4-(1-methyl-1H-pyrazol-4-yl)phenyl)-8-(1-methyl-1H-pyrazol-4-yl)pyrido[3,4-d]pyrimidin-2-amine;

N-(2-chloro-4-(1-methyl-1H-imidazol-5-yl)phenyl)-5-(1-methyl-1H-pyrazol-4-yl)isoquinolin-3-amine;

N-(2-methoxy-4-(1-methyl-1H-pyrazol-4-yl)phenyl)-5-(1-methyl-1H-pyrazol-4-yl)isoquinolin-3-amine;

(3-methoxy-4-((5-(pyrimidin-5-yl)isoquinolin-3-yl)amino)phenyl)(3-methoxyazetidin-1-yl)methanone;

N-(2-methoxy-4-(1-methyl-1H-imidazol-5-yl)phenyl)-5-(1-methyl-1H-pyrazol-4-yl)isoquinolin-3-amine;

(4-((5-(1,5-dimethyl-1H-pyrazol-4-yl)isoquinolin-3-yl)amino)-3-methoxyphenyl)(3-methoxyazetidin-1-yl)methanone;

(3-methoxy-4-((5-(1-methyl-1H-pyrazol-3-yl)isoquinolin-3-yl)amino)phenyl)(3-methoxyazetidin-1-yl)methanone;

N-(2-chloro-4-(1,2-dimethyl-1H-imidazol-5-yl)phenyl)-5-(1-methyl-1H-pyrazol-4-yl)isoquinolin-3-amine;

N-(4-(1,2-dimethyl-1H-imidazol-5-yl)-2-methoxyphenyl)-5-(1-methyl-1H-pyrazol-4-yl)isoquinolin-3-amine;

N-(2-methoxy-4-(1-methyl-1H-pyrazol-4-yl)phenyl)-8-phenylpyrido[3,4-d]pyrimidin-2-amine;

8-cyclopropyl-N-(2-methoxy-4-(1-methyl-1H-pyrazol-4-yl)phenyl)pyrido[3,4-d]pyrimidin-2-amine;

N-(2-methoxy-5-methyl-4-(1-methyl-1H-pyrazol-4-yl)
phenyl)-8-(1-methyl-1H-pyrazol-4-yl)pyrido[3,4-d]
pyrimidin-2-amine;
(3-methoxy-4-((5-(1-methyl-1H-pyrazol-5-yl)isoquino-
lin-3-yl)amino)phenyl)(3-methoxyazetidin-1-yl)
methanone;
(4-((5-(1,3-dimethyl-1H-pyrazol-4-yl)isoquinolin-3-yl)
amino)-3-methoxyphenyl)(3-methoxyazetidin-1-yl)
methanone;
(4-((5-(1-isopropyl-1H-pyrazol-4-yl)isoquinolin-3-yl)
amino)-3-methoxyphenyl)(3-methoxyazetidin-1-yl)
methanone;
4-((5-(1-methyl-1H-pyrazol-4-yl)isoquinolin-3-yl)
amino)-N-(1-methylpiperidin-4-yl)-3-(trifluo-
romethoxy)benzamide;
(4-((5-(3,5-dimethylisoxazol-4-yl)isoquinolin-3-yl)
amino)-3-methoxyphenyl)(3-methoxyazetidin-1-yl)
methanone;
(3-methoxy-4-((5-(1-methyl-1H-imidazol-5-yl)isoquino-
lin-3-yl)amino)phenyl)(3-methoxyazetidin-1-yl)
methanone;
N-(2-methoxy-4-(1-methyl-1H-pyrazol-4-yl)phenyl)-8-
(pyrrolidin-1-yl)pyrido[3,4-d]pyrimidin-2-amine;
N-(4-(1,2-dimethyl-1H-imidazol-5-yl)-2-methoxyphe-
nyl)-8-(1-methyl-1H-pyrazol-4-yl)pyrido[3,4-d]py-
rimidin-2-amine;
tert-butyl 4-(4-(3-((2-methoxy-4-(3-methoxyazetidine-1-
carbonyl)phenyl)amino)isoquinolin-5-yl)-1H-pyrazol-
1-yl)piperidine-1-carboxylate;
(3-methoxy-4-((5-(1-(piperidin-4-yl)-1H-pyrazol-4-yl)
isoquinolin-3-yl)amino)phenyl)(3-methoxyazetidin-1-
yl)methanone;
(3-methoxy-4-((5-(1-(1-methylpiperidin-4-yl)-1H-pyra-
zol-4-yl)isoquinolin-3-yl)amino)phenyl)(3-
methoxyazetidin-1-yl)methanone;
(3-methoxy-4-((5-(1-(2-methoxyethyl)-1H-pyrazol-4-yl)
isoquinolin-3-yl)amino)phenyl)(3-methoxyazetidin-1-
yl)methanone;
N8,N8-diethyl-N2-(2-methoxy-4-(1-methyl-1H-pyrazol-
4-yl)phenyl)pyrido[3,4-d]pyrimidine-2,8-diamine;
N8-cyclopentyl-N2-(2-methoxy-4-(1-methyl-1H-pyra-
zol-4-yl)phenyl)pyrido[3,4-d]pyrimidine-2,8-diamine;
(4-((5-(1-(2-(dimethylamino)ethyl)-1H-pyrazol-4-yl)iso-
quinolin-3-yl)amino)-3-methoxyphenyl)(3-
methoxyazetidin-1-yl)methanone;
N-(2-methoxy-4-(1-methyl-1H-pyrazol-4-yl)phenyl)-5-
(1-methyl-1H-pyrazol-4-yl)-2,6-naphthyridin-3-
amine;
N-(2-methoxy-4-(1-methyl-1H-pyrazol-4-yl)phenyl)-8-
(piperidin-1-yl)pyrido[3,4-d]pyrimidin-2-amine;
N8-cyclohexyl-N2-(2-methoxy-4-(1-methyl-1H-pyrazol-
4-yl)phenyl)pyrido[3,4-d]pyrimidine-2,8-diamine;
N-(2-methoxy-4-(1-methyl-1H-pyrazol-4-yl)phenyl)-8-
(3-methylpyrrolidin-1-yl)pyrido[3,4-d]pyrimidin-2-
amine;
8-(3,3-difluoropyrrolidin-1-yl)-N-(2-methoxy-4-(1-
methyl-1H-pyrazol-4-yl)phenyl)pyrido[3,4-d]pyrimi-
din-2-amine;
N-(4-(1,2-dimethyl-1H-imidazol-5-yl)-2-methoxyphe-
nyl)-5-(1-methyl-1H-pyrazol-4-yl)-2,6-naphthyridin-
3-amine;
N8-(cyclopropylmethyl)-N2-(2-methoxy-4-(1-methyl-
1H-pyrazol-4-yl)phenyl)pyrido[3,4-d]pyrimidine-2,8-
diamine;
8-(1-methyl-1H-pyrazol-4-yl)-N-(2-methyl-4-(1-methyl-
1H-pyrazol-4-yl)phenyl)pyrido[3,4-d]pyrimidin-2-
amine;
N8-cyclopentyl-N2-(2-methoxy-4-(1-methyl-1H-pyra-
zol-4-yl)phenyl)-N8-methylpyrido[3,4-d]pyrimidine-
2,8-diamine;
N-(2-ethoxy-4-(1-methyl-1H-pyrazol-4-yl)phenyl)-8-(1-
methyl-1H-pyrazol-4-yl)pyrido[3,4-d]pyrimidin-2-
amine;
N-(2-isopropoxy-4-(1-methyl-1H-pyrazol-4-yl)phenyl)-
8-(1-methyl-1H-pyrazol-4-yl)pyrido[3,4-d]pyrimidin-
2-amine;
N-(2-(2-methoxyethoxy)-4-(1-methyl-1H-pyrazol-4-yl)
phenyl)-8-(1-methyl-1H-pyrazol-4-yl)pyrido[3,4-d]
pyrimidin-2-amine;
N8-isopentyl-N2-(2-methoxy-4-(1-methyl-1H-pyrazol-4-
yl)phenyl)pyrido[3,4-d]pyrimidine-2,8-diamine;
N-(2-methoxy-4-(1-methyl-1H-pyrazol-4-yl)phenyl)-8-
morpholinopyrido[3,4-d]pyrimidin-2-amine;
N-(2-methoxy-4-(1-methyl-1H-pyrazol-4-yl)phenyl)-8-
(4-methylpiperazin-1-yl)pyrido[3,4-d]pyrimidin-2-
amine;
8-(3,3-difluoroazetidin-1-yl)-N-(2-methoxy-4-(1-methyl-
1H-pyrazol-4-yl)phenyl)pyrido[3,4-d]pyrimidin-2-
amine;
N-(2-methoxy-4-(1-methyl-1H-pyrazol-4-yl)phenyl)-8-
(2-methylpyrrolidin-1-yl)pyrido[3,4-d]pyrimidin-2-
amine;
N8-isobutyl-N2-(2-methoxy-4-(1-methyl-1H-pyrazol-4-
yl)phenyl)pyrido[3,4-d]pyrimidine-2,8-diamine;
8-(cyclohexylthio)-N-(2-methoxy-4-(1-methyl-1H-pyra-
zol-4-yl)phenyl)pyrido[3,4-d]pyrimidin-2-amine;
N-(2-methoxy-4-(1-methyl-1H-pyrazol-4-yl)phenyl)-8-
(6-azaspiro[3.4]octan-6-yl)pyrido[3,4-d]pyrimidin-2-
amine;
N8-cyclohexyl-N2-(2-methoxy-4-(1-(2-(4-methylpiper-
azin-1-yl)ethyl)-1H-pyrazol-4-yl)phenyl)pyrido[3,4-d]
pyrimidine-2,8-diamine;
8-(1-ethyl-1H-pyrazol-4-yl)-N-(2-methoxy-4-(1-methyl-
1H-pyrazol-4-yl)phenyl)pyrido[3,4-d]pyrimidin-2-
amine;
8-(1-isopropyl-1H-pyrazol-4-yl)-N-(2-methoxy-4-(1-
methyl-1H-pyrazol-4-yl)phenyl)pyrido[3,4-d]pyrimi-
din-2-amine;
N-(2-methoxy-4-(1-methyl-1H-pyrazol-4-yl)phenyl)-8-
(3-methoxyazetidin-1-yl)pyrido[3,4-d]pyrimidin-2-
amine;
N1-(cyclopropylmethyl)-N7-(2-methoxy-4-(1-methyl-
1H-pyrazol-4-yl)phenyl)-2,6-naphthyridine-1,7-di-
amine;
N1-cyclohexyl-N7-(2-methoxy-4-(1-methyl-1H-pyrazol-
4-yl)phenyl)-2,6-naphthyridine-1,7-diamine;
N8-cyclohexyl-N2-(4-(1-(2-(dimethylamino)ethyl)-1H-
pyrazol-4-yl)-2-methoxyphenyl)pyrido[3,4-d]pyrimi-
dine-2,8-diamine;
N2-(2-methoxy-4-(1-methyl-1H-pyrazol-4-yl)phenyl)-
N8-neopentylpyrido[3,4-d]pyrimidine-2,8-diamine;
N2-(2-methoxy-4-(1-methyl-1H-pyrazol-4-yl)phenyl)-
N8-(tetrahydro-2H-pyran-4-yl)pyrido[3,4-d]pyrimi-
dine-2,8-diamine;
N8-(cyclopropylmethyl)-N2-(2-methyl-4-(1-methyl-1H-
pyrazol-4-yl)phenyl)pyrido[3,4-d]pyrimidine-2,8-di-
amine;
N8-cyclohexyl-N2-(2-methyl-4-(1-methyl-1H-pyrazol-4-
yl)phenyl)pyrido[3,4-d]pyrimidine-2,8-diamine;
N8-(cyclopropylmethyl)-N2-(2-ethoxy-4-(1-methyl-1H-
pyrazol-4-yl)phenyl)pyrido[3,4-d]pyrimidine-2,8-di-
amine;

N8-(cyclohexylmethyl)-N2-(2-methoxy-4-(1-methyl-1H-pyrazol-4-yl)phenyl)pyrido[3,4-d]pyrimidine-2,8-diamine;

2-(4-(4-((8-(cyclohexylamino)pyrido[3,4-d]pyrimidin-2-yl)amino)-3-methoxyphenyl)-1H-pyrazol-1-yl)ethanol;

8-(cyclopropylmethoxy)-N-(2-methoxy-4-(1-methyl-1H-pyrazol-4-yl)phenyl)pyrido[3,4-d]pyrimidin-2-amine;

1-((2-(2-methoxy-4-(1-methyl-1H-pyrazol-4-yl)phenyl)amino)pyrido[3,4-d]pyrimidin-8-yl)amino)-2-methylpropan-2-ol;

N2-(2-methoxy-4-(1-methyl-1H-pyrazol-4-yl)phenyl)-N8-(oxetan-3-ylmethyl)pyrido[3,4-d]pyrimidine-2,8-diamine;

N8-(3,3-dimethylbutan-2-yl)-N2-(2-methoxy-4-(1-methyl-1H-pyrazol-4-yl)phenyl)pyrido[3,4-d]pyrimidine-2,8-diamine;

3-((2-(2-methoxy-4-(1-methyl-1H-pyrazol-4-yl)phenyl)amino)pyrido[3,4-d]pyrimidin-8-yl)amino)-2,2-dimethylpropan-1-ol;

N2-(2-ethoxy-4-(1-methyl-1H-pyrazol-4-yl)phenyl)-N8-(tetrahydro-2H-pyran-4-yl)pyrido[3,4-d]pyrimidine-2,8-diamine;

N2-(2-methoxy-6-morpholinopyridin-3-yl)-N8-neopentylpyrido[3,4-d]pyrimidine-2,8-diamine;

N2-(2-methoxy-6-(methylsulfonyl)pyridin-3-yl)-N8-neopentylpyrido[3,4-d]pyrimidine-2,8-diamine;

N2-(2-methoxy-4-(1-methyl-1H-imidazol-5-yl)phenyl)-N8-neopentylpyrido[3,4-d]pyrimidine-2,8-diamine;

N2-(4-(1,3-dimethyl-1H-pyrazol-4-yl)-2-methoxyphenyl)-N8-neopentylpyrido[3,4-d]pyrimidine-2,8-diamine;

N8-(1-cyclopropylethyl)-N2-(2-methoxy-4-(1-methyl-1H-pyrazol-4-yl)phenyl)pyrido[3,4-d]pyrimidine-2,8-diamine;

2-(4-(3-methoxy-4-((8-((tetrahydro-2H-pyran-4-yl)amino)pyrido[3,4-d]pyrimidin-2-yl)amino)phenyl)-1H-pyrazol-1-yl)ethanol;

N2-(4-(1,5-dimethyl-1H-pyrazol-4-yl)-2-methoxyphenyl)-N8-neopentylpyrido[3,4-d]pyrimidine-2,8-diamine;

(R)—N8-(3,3-dimethylbutan-2-yl)-N2-(2-methoxy-4-(1-methyl-1H-pyrazol-4-yl)phenyl)pyrido[3,4-d]pyrimidine-2,8-diamine;

(S)-N8-(3,3-dimethylbutan-2-yl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(tetrahydrofuran-3-yl)pyrido[3,4-d]pyrimidine-2,8-diamine;

N2-(2-methoxy-4-(1-methyl-1H-pyrazol-4-yl)phenyl)-N8-((tetrahydrofuran-3-yl)methyl)pyrido[3,4-d]pyrimidine-2,8-diamine;

1-(2-(2-methoxy-4-(1-methyl-1H-pyrazol-4-yl)phenyl)amino)pyrido[3,4-d]pyrimidin-8-yl)pyrrolidin-3-ol;

N2-(2-methoxy-4-(1-methyl-1H-pyrazol-4-yl)phenyl)-N8-methyl-N8-(tetrahydro-2H-pyran-4-yl)pyrido[3,4-d]pyrimidine-2,8-diamine;

N8-(tert-butyl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(1-methylcyclohexyl)pyrido[3,4-d]pyrimidine-2,8-diamine;

8-(1-(2,2-difluoroethyl)-1H-pyrazol-4-yl)-N-(2-methoxy-4-(1-methyl-1H-pyrazol-4-yl)phenyl)pyrido[3,4-d]pyrimidin-2-amine;

N2-(4-(1,2-dimethyl-1H-imidazol-5-yl)-2-methoxyphenyl)-N8-neopentylpyrido[3,4-d]pyrimidine-2,8-diamine;

N2-(2-methoxy-4-(1-methyl-1H-pyrazol-4-yl)phenyl)-6-methyl-N8-neopentylpyrido[3,4-d]pyrimidine-2,8-diamine;

N2-(2-methoxy-4-morpholinophenyl)-N8-neopentylpyrido[3,4-d]pyrimidine-2,8-diamine;

N8-(2,2-difluoropropyl)-N2-(2-methoxy-4-(1-methyl-1H-pyrazol-4-yl)phenyl)pyrido[3,4-d]pyrimidine-2,8-diamine;

N8-(3-methoxy-2,2-dimethylpropyl)-N2-(2-methoxy-4-(1-methyl-1H-pyrazol-4-yl)phenyl)pyrido[3,4-d]pyrimidine-2,8-diamine;

N8-(2-methoxy-2-methylpropyl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(2,2,2-trifluoroethyl)pyrido[3,4-d]pyrimidine-2,8-diamine;

N-(2-methoxy-4-(1-methyl-1H-pyrazol-4-yl)phenyl)-8-(2-oxa-6-azaspiro[3.4]octan-6-yl)pyrido[3,4-d]pyrimidin-2-amine;

1-(((2-((2-methoxy-4-(1-methyl-1H-pyrazol-4-yl)phenyl)amino)pyrido[3,4-d]pyrimidin-8-yl)amino)methyl)cyclobutanol;

8-chloro-N-(2-methoxy-4-(1-methyl-1H-pyrazol-4-yl)phenyl)pyrido[3,4-d]pyrimidin-2-amine;

N2-(2-ethyl-4-(1-methyl-1H-pyrazol-4-yl)phenyl)-N8-neopentylpyrido[3,4-d]pyrimidine-2,8-diamine;

N2-(4-(1-methyl-1H-pyrazol-4-yl)-2-(trifluoromethoxy)phenyl)-N8-neopentylpyrido[3,4-d]pyrimidine-2,8-diamine;

N2-(2-methoxy-4-(1-methyl-1H-pyrazol-4-yl)phenyl)-N8-methylpyrido[3,4-d]pyrimidine-2,8-diamine;

N2-(2-methoxy-4-(1-methyl-1H-pyrazol-4-yl)phenyl)-N8,N8-dimethylpyrido[3,4-d]pyrimidine-2,8-diamine;

N-(2-((2-methoxy-4-(1-methyl-1H-pyrazol-4-yl)phenyl)amino)pyrido[3,4-d]pyrimidin-8-yl)-2-methylpropane-2-sulfinamide;

N2-(2-methoxy-4-(4-morpholinopiperidin-1-yl)phenyl)-N8-neopentylpyrido[3,4-d]pyrimidine-2,8-diamine;

N2-(2-methoxy-4-(1-methyl-1H-pyrazol-4-yl)phenyl)-N8-((3-methyloxetan-3-yl)methyl)pyrido[3,4-d]pyrimidine-2,8-diamine;

N2-(2-methoxy-4-(piperidin-1-yl)phenyl)-N8-neopentylpyrido[3,4-d]pyrimidine-2,8-diamine;

N-(2-((2-methoxy-4-(1-methyl-1H-pyrazol-4-yl)phenyl)amino)pyrido[3,4-d]pyrimidin-8-yl)-2-methylpropane-2-sulfonamide;

N2-(2-methoxy-4-(1-methyl-1H-pyrazol-4-yl)phenyl)-N8-(oxetan-3-yl)pyrido[3,4-d]pyrimidine-2,8-diamine;

(1-(3-methoxy-4-((8-(neopentylamino)pyrido[3,4-d]pyrimidin-2-yl)amino)phenyl)piperidin-4-yl)(morpholino)methanone;

N2-(2-methoxy-4-(4-methylpiperazin-1-yl)phenyl)-N8-neopentylpyrido[3,4-d]pyrimidine-2,8-diamine;

1-(((2-((2-methoxy-4-(1-methyl-1H-pyrazol-4-yl)phenyl)amino)pyrido[3,4-d]pyrimidin-8-yl)amino)methyl)cyclopropanol;

N2-(2-methoxy-4-(1-methyl-1H-pyrazol-4-yl)phenyl)-N8-(1-methylpiperidin-4-yl)pyrido[3,4-d]pyrimidine-2,8-diamine;

2-((2-(2-methoxy-4-(1-methyl-1H-pyrazol-4-yl)phenyl)amino)pyrido[3,4-d]pyrimidin-8-yl)amino)-2-methylpropan-1-ol;

N-(2-methoxy-4-(1-methyl-1H-pyrazol-4-yl)phenyl)-8-(2-oxa-6-azaspiro[3.3]heptan-6-yl)pyrido[3,4-d]pyrimidin-2-amine;

N2-(2-methoxy-4-(1-methyl-1H-pyrazol-4-yl)phenyl)-N8-(oxetan-2-ylmethyl)pyrido[3,4-d]pyrimidine-2,8-diamine;

N2-(2-chloro-4-morpholinophenyl)-N8-neopentylpyrido[3,4-d]pyrimidine-2,8-diamine N2-(2-methoxy-4-(4-methyl-4H-1,2,4-triazol-3-yl)phenyl)-N8-neopentylpyrido[3,4-d]pyrimidine-2,8-diamine;

N2-(2-methoxy-4-(4-(methylsulfonyl)piperazin-1-yl)phenyl)-N8-neopentylpyrido[3,4-d]pyrimidine-2,8-diamine;

N2-(2-methoxy-4-(1-methyl-1H-pyrazol-4-yl)phenyl)-N8-((3-methyltetrahydrofuran-3-yl)methyl)pyrido[3,4-d]pyrimidine-2,8-diamine;

N-(4-(1,5-dimethyl-1H-pyrazol-4-yl)-2-methoxyphenyl)-8-(2-oxa-6-azaspiro[3.4]octan-6-yl)pyrido[3,4-d]pyrimidin-2-amine;

N2-(4-(1,5-dimethyl-1H-pyrazol-4-yl)-2-methoxyphenyl)-N8-((3-methyloxetan-3-yl)methyl)pyrido[3,4-d]pyrimidine-2,8-diamine;

N2-(4-(1,5-dimethyl-1H-pyrazol-4-yl)-2-methoxyphenyl)-N8-(2-methoxy-2-methylpropyl)pyrido[3,4-d]pyrimidine-2,8-diamine;

N2-(4-(1,2-dimethyl-1H-imidazol-5-yl)-2-methoxyphenyl)-N8-(2-methoxy-2-methylpropyl)-6-methylpyrido[3,4-d]pyrimidine-2,8-diamine;

N2-(4-(1,2-dimethyl-1H-imidazol-5-yl)-2-methoxyphenyl)-6-methyl-N8-neopentylpyrido[3,4-d]pyrimidine-2,8-diamine;

N2-(2-methoxy-4-(4-methyl-4H-1,2,4-triazol-3-yl)phenyl)-6-methyl-N8-neopentylpyrido[3,4-d]pyrimidine-2,8-diamine;

N-(2-ethoxy-4-(1-methyl-1H-pyrazol-4-yl)phenyl)-8-(2-oxa-6-azaspiro[3.4]octan-6-yl)pyrido[3,4-d]pyrimidin-2-amine;

2-((2-((2-methoxy-4-(1-methyl-1H-pyrazol-4-yl)phenyl)amino)pyrido[3,4-d]pyrimidin-8-yl)amino)ethanol;

N2-(2-methoxy-4-(1-methyl-1H-pyrazol-4-yl)phenyl)-N8-(2-methoxyethyl)pyrido[3,4-d]pyrimidine-2,8-diamine;

1-((2-((2-methoxy-4-(1-methyl-1H-pyrazol-4-yl)phenyl)amino)pyrido[3,4-d]pyrimidin-8-yl)amino)propan-2-ol;

2-((2-((2-methoxy-4-(1-methyl-1H-pyrazol-4-yl)phenyl)amino)pyrido[3,4-d]pyrimidin-8-yl)amino)propan-1-ol;

N2-(4-(1,5-dimethyl-1H-pyrazol-4-yl)-2-methoxyphenyl)-N8-((3-methyltetrahydrofuran-3-yl)methyl)pyrido[3,4-d]pyrimidine-2,8-diamine;

4-(2-((2-methoxy-4-(1-methyl-1H-pyrazol-4-yl)phenyl)amino)pyrido[3,4-d]pyrimidin-8-yl)thiomorpholine 1,1-dioxide;

N-(2-methoxy-4-(1-methyl-1H-pyrazol-4-yl)phenyl)-8-(7-oxa-2-azaspiro[3.5]nonan-2-yl)pyrido[3,4-d]pyrimidin-2-amine;

N2-(2-methoxy-4-(1-methyl-1H-pyrazol-4-yl)phenyl)-5-methyl-N8-neopentylpyrido[3,4-d]pyrimidine-2,8-diamine;

N-(2-methoxy-4-(1-methyl-1H-pyrazol-4-yl)phenyl)-8-(6-oxa-2-azaspiro[3.4]octan-2-yl)pyrido[3,4-d]pyrimidin-2-amine;

1-(2-((2-methoxy-4-(1-methyl-1H-pyrazol-4-yl)phenyl)amino)pyrido[3,4-d]pyrimidin-8-yl)azetidine-3-carbonitrile;

N-(2-methoxy-4-(1-methyl-1H-pyrazol-4-yl)phenyl)-8-(2-oxa-7-azaspiro[4.4]nonan-7-yl)pyrido[3,4-d]pyrimidin-2-amine;

N-(2-methoxy-4-(1-methyl-1H-pyrazol-4-yl)phenyl)-8-(2-oxa-6-azaspiro[3.5]nonan-6-yl)pyrido[3,4-d]pyrimidin-2-amine;

N8-((3-fluorooxetan-3-yl)methyl)-N2-(2-methoxy-4-(1-methyl-1H-pyrazol-4-yl)phenyl)pyrido[3,4-d]pyrimidine-2,8-diamine;

N-(4-chloro-2-methoxyphenyl)-8-(2-oxa-6-azaspiro[3.4]octan-6-yl)pyrido[3,4-d]pyrimidin-2-amine;

N-(2,4-dichlorophenyl)-8-(2-oxa-6-azaspiro[3.4]octan-6-yl)pyrido[3,4-d]pyrimidin-2-amine;

4-((8-(2-oxa-6-azaspiro[3.4]octan-6-yl)pyrido[3,4-d]pyrimidin-2-yl)amino)-3-methoxybenzonitrile;

N-(2-chloro-4-(methylsulfonyl)phenyl)-8-(2-oxa-6-azaspiro[3.4]octan-6-yl)pyrido[3,4-d]pyrimidin-2-amine;

N-(2-chloro-4-(pyrimidin-5-yl)phenyl)-8-(2-oxa-6-azaspiro[3.4]octan-6-yl)pyrido[3,4-d]pyrimidin-2-amine;

N-(2-chloro-4-(5-methyl-1,3,4-oxadiazol-2-yl)phenyl)-8-(2-oxa-6-azaspiro[3.4]octan-6-yl)pyrido[3,4-d]pyrimidin-2-amine;

N8-(2-methoxy-2-methylpropyl)-N2-(2-methoxy-4-(4-methyl-4H-1,2,4-triazol-3-yl)phenyl)-6-methylpyrido[3,4-d]pyrimidine-2,8-diamine;

6-cyclopropyl-N-(2-methoxy-4-(1-methyl-1H-pyrazol-4-yl)phenyl)-8-(2-oxa-6-azaspiro[3.4]octan-6-yl)pyrido[3,4-d]pyrimidin-2-amine;

2-((2-((2-methoxy-4-(1-methyl-1H-pyrazol-4-yl)phenyl)amino)pyrido[3,4-d]pyrimidin-8-yl)amino)propane-1,3-diol;

3-methoxy-2-((2-((2-methoxy-4-(1-methyl-1H-pyrazol-4-yl)phenyl)amino)pyrido[3,4-d]pyrimidin-8-yl)amino)propan-1-ol;

(3-(((2-((2-methoxy-4-(1-methyl-1H-pyrazol-4-yl)phenyl)amino)pyrido[3,4-d]pyrimidin-8-yl)amino)methyl)oxetan-3-yl)methanol;

(S)-N2-(2-methoxy-4-(1-methyl-1H-pyrazol-4-yl)phenyl)-N8-((3-methyltetrahydrofuran-3-yl)methyl)pyrido[3,4-d]pyrimidine-2,8-diamine;

(R)—N2-(2-methoxy-4-(1-methyl-1-pyrazol-4-yl)phenyl)-N8-((3-methyltetrahydrofuran-3-yl)methyl)pyrido[3,4-d]pyrimidine-2,8-diamine;

N-(4-chloro-2-fluorophenyl)-8-(2-oxa-6-azaspiro[3.4]octan-6-yl)pyrido[3,4-d]pyrimidin-2-amine;

4-((8-(2-oxa-6-azaspiro[3.4]octan-6-yl)pyrido[3,4-d]pyrimidin-2-yl)amino)-3-chlorobenzonitrile;

N2-(2-methoxy-4-(1-(2-methoxyethyl)-2-methyl-1H-imidazol-5-yl)phenyl)-6-methyl-N8-neopentylpyrido[3,4-d]pyrimidine-2,8-diamine;

N2-(2-ethoxy-4-(4-methyl-4H-1,2,4-triazol-3-yl)phenyl)-6-methyl-N8-neopentylpyrido[3,4-d]pyrimidine-2,8-diamine;

N2-(2-methoxy-4-(4-(methylsulfonyl)piperazin-1-yl)phenyl)-6-methyl-N8-neopentylpyrido[3,4-d]pyrimidine-2,8-diamine;

N-(2-methoxy-4-(1-methyl-1H-pyrazol-4-yl)phenyl)-8-(pyridin-4-yl)pyrido[3,4-d]pyrimidin-2-amine;

N8-(2-methoxy-2-methylpropyl)-N2-(2-methoxy-4-(4-methyl-4H-1,2,4-triazol-3-yl)phenyl)-5-methylpyrido[3,4-d]pyrimidine-2,8-diamine;

N2-(2-methoxy-4-(4-methyl-4H-1,2,4-triazol-3-yl)phenyl)-5-methyl-N8-neopentylpyrido[3,4-d]pyrimidine-2,8-diamine;

N-(2-methoxy-4-(1-methyl-1H-pyrazol-4-yl)phenyl)-8-(2-methylmorpholino)pyrido[3,4-d]pyrimidin-2-amine;

(4-(3-methoxy-4-((8-((2-methoxy-2-methylpropyl)amino)pyrido[3,4-d]pyrimidin-2-yl)amino)phenyl)-1-methyl-1H-pyrazol-5-yl)methanol;

(4-(3-methoxy-4-((8-(((3-methyltetrahydrofuran-3-yl)methyl)amino)pyrido[3,4-d]pyrimidin-2-yl)amino)phenyl)-1-methyl-1H-pyrazol-5-yl)methanol;

N8-(2-methoxy-2-methylpropyl)-N2-(2-methoxy-4-(1-(2-methoxyethyl)-2-methyl-1H-imidazol-5-yl)phenyl)pyrido[3,4-d]pyrimidine-2,8-diamine;

N2-(2-methoxy-4-(1-(2-methoxyethyl)-2-methyl-1H-imidazol-5-yl)phenyl)-N8-((3-methyltetrahydrofuran-3-yl)methyl)pyrido[3,4-d]pyrimidine-2,8-diamine;

N2-(2-ethoxy-4-(4-methyl-4H-1,2,4-triazol-3-yl)phenyl)-N8-(2-methoxy-2-methylpropyl)pyrido[3,4-d]pyrimidine-2,8-diamine;

N2-(2-ethoxy-4-(4-methyl-4H-1,2,4-triazol-3-yl)phenyl)-N8-((3-methyltetrahydrofuran-3-yl)methyl)pyrido[3,4-d]pyrimidine-2,8-diamine;

8-(3,6-dihydro-2H-pyran-4-yl)-N-(2-methoxy-4-(1-methyl-1H-pyrazol-4-yl)phenyl)pyrido[3,4-d]pyrimidin-2-amine;

N8-(2-methoxy-2-methylpropyl)-N2-(2-methoxy-6-(1-methyl-1H-tetrazol-5-yl)pyridin-3-yl)pyrido[3,4-d]pyrimidine-2,8-diamine;

N2-(6-(1,2-dimethyl-1H-imidazol-5-yl)-2-methoxypyridin-3-yl)-N8-(2-methoxy-2-methylpropyl)pyrido[3,4-d]pyrimidine-2,8-diamine;

N8-(2-methoxy-2-methylpropyl)-N2-(2-methoxy-4-(1-methyl-1H-tetrazol-5-yl)phenyl)pyrido[3,4-d]pyrimidine-2,8-diamine;

N-(2-methoxy-4-(1-methyl-1H-pyrazol-4-yl)phenyl)-8-(pyrimidin-5-yl)pyrido[3,4-d]pyrimidin-2-amine;

N2-(2-methoxy-4-(1-methyl-1H-pyrazol-4-yl)phenyl)-N8-(1-(tetrahydrofuran-3-yl)ethyl)pyrido[3,4-d]pyrimidine-2,8-diamine;

N2-(4-(1,3-dimethyl-1H-pyrazol-4-yl)-2-methoxyphenyl)-N8-(2-methoxy-2-methylpropyl)pyrido[3,4-d]pyrimidine-2,8-diamine;

N2-(4-(1,3-dimethyl-1H-pyrazol-4-yl)-2-methoxyphenyl)-N8-((3-methyltetrahydrofuran-3-yl)methyl)pyrido[3,4-d]pyrimidine-2,8-diamine;

N-(2-methoxy-4-(1-methyl-1H-pyrazol-4-yl)phenyl)-8-(4-methoxypiperidin-1-yl)pyrido[3,4-d]pyrimidin-2-amine;

1-(2-((2-methoxy-4-(1-methyl-1H-pyrazol-4-yl)phenyl)amino)pyrido[3,4-d]pyrimidin-8-yl)piperidine-4-carbonitrile;

N-(2-methoxy-4-(1-methyl-1H-pyrazol-4-yl)phenyl)-8-(4-(methylsulfonyl)piperazin-1-yl)pyrido[3,4-d]pyrimidin-2-amine;

N2-(4-(1,3-dimethyl-1H-pyrazol-4-yl)-2-methoxyphenyl)-N8-(2-methoxy-2-methylpropyl)-6-methylpyrido[3,4-d]pyrimidine-2,8-diamine;

N-(2-ethoxy-4-(4-methyl-4H-1,2,4-triazol-3-yl)phenyl)-6-methyl-8-(6-oxa-2-azaspiro[3.4]octan-2-yl)pyrido[3,4-d]pyrimidin-2-amine;

N2-(6-(1,3-dimethyl-1H-pyrazol-4-yl)-2-methoxypyridin-3-yl)-N8-(2-methoxy-2-methylpropyl)pyrido[3,4-d]pyrimidine-2,8-diamine;

N2-(6-(1,5-dimethyl-1H-pyrazol-4-yl)-2-methoxypyridin-3-yl)-N8-(2-methoxy-2-methylpropyl)pyrido[3,4-d]pyrimidine-2,8-diamine;

N8-(2-methoxy-2-methylpropyl)-N2-(2-methoxy-6-(1-methyl-1H-1,2,3-triazol-5-yl)pyridin-3-yl)pyrido[3,4-d]pyrimidine-2,8-diamine;

N8-(2-methoxy-2-methylpropyl)-N2-(2-methoxy-6-(2-methyl-2H-1,2,3-triazol-4-yl)pyridin-3-yl)pyrido[3,4-d]pyrimidine-2,8-diamine;

(3-methoxy-4-((8-((2-methoxy-2-methylpropyl)amino)pyrido[3,4-d]pyrimidin-2-yl)amino)phenyl)(3-methoxyazetidin-1-yl)methanone;

3-methoxy-4-((8-((2-methoxy-2-methylpropyl)amino)pyrido[3,4-d]pyrimidin-2-yl)amino)-N,N-dimethylbenzamide;

(3-methoxy-4-((8-((2-methoxy-2-methylpropyl)amino)pyrido[3,4-d]pyrimidin-2-yl)amino)phenyl)(4-methylpiperazin-1-yl)methanone;

(1-(2-((2-methoxy-4-(1-methyl-1H-pyrazol-4-yl)phenyl)amino)pyrido[3,4-d]pyrimidin-8-yl)pyrrolidin-3-yl)methanol;

(1-(2-((2-methoxy-4-(1-methyl-1H-pyrazol-4-yl)phenyl)amino)pyrido[3,4-d]pyrimidin-8-yl)piperidin-3-yl)methanol;

(4-(2-((2-methoxy-4-(1-methyl-1H-pyrazol-4-yl)phenyl)amino)pyrido[3,4-d]pyrimidin-8-yl)morpholin-2-yl)methanol;

N2-(2-(difluoromethoxy)-4-(1-methyl-1H-pyrazol-4-yl)phenyl)-N8-(2-methoxy-2-methylpropyl)pyrido[3,4-d]pyrimidine-2,8-diamine;

N2-(2-(difluoromethoxy)-4-fluorophenyl)-N8-(2-methoxy-2-methylpropyl)pyrido[3,4-d]pyrimidine-2,8-diamine;

N2-(4-(1-ethyl-1H-pyrazol-4-yl)-2-methoxyphenyl)-N8-(2-methoxy-2-methylpropyl)pyrido[3,4-d]pyrimidine-2,8-diamine;

(3-methoxy-4-((8-(neopentylamino)pyrido[3,4-d]pyrimidin-2-yl)amino)phenyl)(3-methoxyazetidin-1-yl)methanone;

N2-(2-methoxy-4-(tetrahydro-2H-pyran-4-yl)phenyl)-N8-((3-methyltetrahydrofuran-3-yl)methyl)pyrido[3,4-d]pyrimidine-2,8-diamine;

N2-(4-chloro-2-(difluoromethoxy)phenyl)-N8-(2-methoxy-2-methylpropyl)pyrido[3,4-d]pyrimidine-2,8-diamine;

N2-(2-methoxy-4-(4-methyl-4H-1,2,4-triazol-3-yl)phenyl)-5-methyl-N8-((3-methyloxetan-3-yl)methyl)pyrido[3,4-d]pyrimidine-2,8-diamine;

N2-(2-methoxy-4-(4-methyl-4H-1,2,4-triazol-3-yl)phenyl)-5-methyl-N8-((3-methyltetrahydrofuran-3-yl)methyl)pyrido[3,4-d]pyrimidine-2,8-diamine;

N-(2-methoxy-4-(4-methyl-4H-1,2,4-triazol-3-yl)phenyl)-5-methyl-8-(6-oxa-2-azaspiro[3.4]octan-2-yl)pyrido[3,4-d]pyrimidin-2-amine;

N8-(2-methoxy-2-methylpropyl)-N2-(2-methoxy-4-(1-methyl-1H-1,2,4-triazol-3-yl)phenyl)-6-methylpyrido[3,4-d]pyrimidine-2,8-diamine;

N2-(2-(difluoromethoxy)-4-(1-methyl-1H-pyrazol-4-yl)phenyl)-N8-(2-methoxy-2-methylpropyl)-6-methylpyrido[3,4-d]pyrimidine-2,8-diamine;

(4-(3-methoxy-4-((8-((2-methoxy-2-methylpropyl)amino)-6-methylpyrido[3,4-d]pyrimidin-2-yl)amino)phenyl)-1-methyl-1H-pyrazol-5-yl)methanol;

N2-(2-methoxy-4-(1-methyl-1H-1,2,3-triazol-5-yl)phenyl)-6-methyl-N8-neopentylpyrido[3,4-d]pyrimidine-2,8-diamine;

N2-(2-ethoxy-4-(4-methyl-4H-1,2,4-triazol-3-yl)phenyl)-6-methyl-N8-((3-methyltetrahydrofuran-3-yl)methyl)pyrido[3,4-d]pyrimidine-2,8-diamine;

1-(((2-((2-ethoxy-4-(4-methyl-4H-1,2,4-triazol-3-yl)phenyl)amino)-6-methylpyrido[3,4-d]pyrimidin-8-yl)amino)methyl)cyclobutanol;

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile;

N-(2-ethoxy-4-(4-methyl-4H-1,2,4-triazol-3-yl)phenyl)-6-methyl-8-(7-oxa-2-azaspiro[3.5]nonan-2-yl)pyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)piperidine-4-carbonitrile;

1-(2-((2-ethoxy-4-(4-methyl-4H-1,2,4-triazol-3-yl)phenyl)amino)-6-methylpyrido[3,4-d]pyrimidin-8-yl)-3-methylazetidin-3-ol;

N2-(2-ethoxy-4-(4-methyl-4H-1,2,4-triazol-3-yl)phenyl)-6-methyl-N8-((3-methyloxetan-3-yl)methyl)pyrido[3,4-d]pyrimidine-2,8-diamine;

N2-(2-ethoxy-4-(4-methyl-4H-1,2,4-triazol-3-yl)phenyl)-6-methyl-N8-(tetrahydro-2H-pyran-4-yl)pyrido[3,4-d]pyrimidine-2,8-diamine;

N-(2-ethoxy-4-(4-methyl-4H-1,2,4-triazol-3-yl)phenyl)-6-methyl-8-(2-oxa-7-azaspiro[4.4]nonan-7-yl)pyrido[3,4-d]pyrimidin-2-amine;

1-(((2-((2-ethoxy-4-(4-methyl-4H-1,2,4-triazol-3-yl)phenyl)amino)-6-methylpyrido[3,4-d]pyrimidin-8-yl)amino)methyl)cyclopropanol;

N2-(4-(1,2-dimethyl-1H-imidazol-5-yl)-2-methoxyphenyl)-6-methyl-N8-((3-methyltetrahydrofuran-3-yl)methyl)pyrido[3,4-d]pyrimidine-2,8-diamine;

N-(4-(1,2-dimethyl-1H-imidazol-5-yl)-2-methoxyphenyl)-6-methyl-8-(2-oxa-7-azaspiro[4.4]nonan-7-yl)pyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)piperidine-4-carbonitrile;

1-(2-((4-(1,2-dimethyl-1H-imidazol-5-yl)-2-methoxyphenyl)amino)-6-methylpyrido[3,4-d]pyrimidin-8-yl)-3-methylazetidine-3-carbonitrile;

N-(2-ethoxy-4-(4-methyl-4H-1,2,4-triazol-3-yl)phenyl)-6-methyl-8-(1-oxa-6-azaspiro[3.3]heptan-6-yl)pyrido[3,4-d]pyrimidin-2-amine;

N2-(2-methoxy-4-(1-methyl-1H-pyrazol-3-yl)phenyl)-6-methyl-N8-neopentylpyrido[3,4-d]pyrimidine-2,8-diamine;

8-(3,3-difluoroazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(4-methoxypiperidin-1-yl)-6-methylpyrido[3,4-d]pyrimidin-2-amine;

N-(2-ethoxy-4-(4-methyl-4H-1,2,4-triazol-3-yl)phenyl)-8-(3-methoxypiperidin-1-yl)-6-methylpyrido[3,4-d]pyrimidin-2-amine;

N-(2-ethoxy-4-(4-methyl-4H-1,2,4-triazol-3-yl)phenyl)-6-methyl-8-(2-methylmorpholino)pyrido[3,4-d]pyrimidin-2-amine;

N-(2-ethoxy-4-(4-methyl-4H-1,2,4-triazol-3-yl)phenyl)-8-(4-methoxy-4-methylpiperidin-1-yl)-6-methylpyrido[3,4-d]pyrimidin-2-amine;

8-(3-azabicyclo[3.1.0]hexan-3-yl)-N-(2-ethoxy-4-(4-methyl-4H-1,2,4-triazol-3-yl)phenyl)-6-methylpyrido[3,4-d]pyrimidin-2-amine;

8-(3-(dimethylamino)azetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)piperidin-4-ol;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylpyrrolidin-3-ol;

1-(2-((2-ethoxy-4-(4-methyl-4H-1,2,4-triazol-3-yl)phenyl)amino)-6-methylpyrido[3,4-d]pyrimidin-8-yl)-4-methylpiperidine-4-carbonitrile;

1-(2-((2-ethoxy-4-(4-methyl-4H-1,2,4-triazol-3-yl)phenyl)amino)-6-methylpyrido[3,4-d]pyrimidin-8-yl)pyrrolidine-3-carbonitrile;

N2-(2-methoxy-4-(1-methyl-1H-imidazol-2-yl)phenyl)-6-methyl-N8-neopentylpyrido[3,4-d]pyrimidine-2,8-diamine;

N2-(2-methoxy-4-(1-methyl-1H-pyrazol-5-yl)phenyl)-6-methyl-N8-neopentylpyrido[3,4-d]pyrimidine-2,8-diamine;

N2-(2-methoxy-4-(oxazol-2-yl)phenyl)-6-methyl-N8-neopentylpyrido[3,4-d]pyrimidine-2,8-diamine;

N-(2-ethoxy-4-(4-methyl-4H-1,2,4-triazol-3-yl)phenyl)-8-(3-methoxypyrrolidin-1-yl)-6-methylpyrido[3,4-d]pyrimidin-2-amine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylpyrrolidine-3-carbonitrile;

8-(2,2-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-6-methyl-8-(3-(trifluoromethyl)azetidin-1-yl)pyrido[3,4-d]pyrimidin-2-amine;

N-(2-ethoxy-4-(4-methyl-4H-1,2,4-triazol-3-yl)phenyl)-6-methyl-8-(2-azaspiro[3.3]heptan-2-yl)pyrido[3,4-d]pyrimidin-2-amine;

(R)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

(S)-N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

N2-(2-ethoxy-4-(4-methyl-4H-1,2,4-triazol-3-yl)phenyl)-N8-((1-methoxycyclobutyl)methyl)-6-methylpyrido[3,4-d]pyrimidine-2,8-diamine;

N2-(2-ethoxy-4-(4-methyl-4H-1,2,4-triazol-3-yl)phenyl)-6-methyl-N8-(1-methylazetidin-3-yl)pyrido[3,4-d]pyrimidine-2,8-diamine;

N2-(2-ethoxy-4-(4-methyl-4H-1,2,4-triazol-3-yl)phenyl)-6-methyl-N8-(oxetan-3-ylmethyl)pyrido[3,4-d]pyrimidine-2,8-diamine;

N-(2-ethoxy-4-(4-methyl-4H-1,2,4-triazol-3-yl)phenyl)-6-methyl-8-(pyrrolidin-1-yl)pyrido[3,4-d]pyrimidin-2-amine;

N-(2-ethoxy-4-(4-methyl-4H-1,2,4-triazol-3-yl)phenyl)-6-methyl-8-(2-azaspiro[3.4]octan-2-yl)pyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-ethylazetidin-3-ol;

N2-(2-ethoxy-4-(4-methyl-4H-1,2,4-triazol-3-yl)phenyl)-6-methyl-N8-(1-methylpiperidin-4-yl)pyrido[3,4-d]pyrimidine-2,8-diamine;

8-(4-(dimethylamino)piperidin-1-yl)-N-(2-ethoxy-4-(4-methyl-4H-1,2,4-triazol-3-yl)phenyl)-6-methylpyrido[3,4-d]pyrimidin-2-amine;

N2-(2-ethoxy-4-(4-methyl-4H-1,2,4-triazol-3-yl)phenyl)-6-methyl-N8-((tetrahydro-2H-pyran-4-yl)methyl)pyrido[3,4-d]pyrimidine-2,8-diamine;

N2-(2-ethoxy-4-(4-methyl-4H-1,2,4-triazol-3-yl)phenyl)-6-methyl-N8-((4-methyltetrahydro-2H-pyran-4-yl)methyl)pyrido[3,4-d]pyrimidine-2,8-diamine;

1-(2-((2-ethoxy-4-(4-methyl-4H-1,2,4-triazol-3-yl)phenyl)amino)-6-methylpyrido[3,4-d]pyrimidin-8-yl)-4-ethylpiperidine-4-carbonitrile;

N2-(2-ethoxy-4-(4-methyl-4H-1,2,4-triazol-3-yl)phenyl)-6-methyl-N8-(2-(3-methyltetrahydrofuran-3-yl)ethyl)pyrido[3,4-d]pyrimidine-2,8-diamine;

N2-(2-ethoxy-4-(4-methyl-4H-1,2,4-triazol-3-yl)phenyl)-6-methyl-N8-(1-(tetrahydro-2H-pyran-4-yl)ethyl)pyrido[3,4-d]pyrimidine-2,8-diamine;

N2-(2-ethoxy-4-(4-methyl-4H-1,2,4-triazol-3-yl)phenyl)-6-methyl-N8-(pentan-3-yl)pyrido[3,4-d]pyrimidine-2,8-diamine;

N2-(2-ethoxy-4-(4-methyl-4H-1,2,4-triazol-3-yl)phenyl)-6-methyl-N8-(tetrahydrofuran-3-yl)pyrido[3,4-d]pyrimidine-2,8-diamine;

8-(3-ethoxy-3-methylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-ethyl-3-methoxyazetidin-1-yl)-6-methylpyrido[3,4-d]pyrimidin-2-amine;

8-(3-ethoxy-3-ethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-isopropyl-3-methoxyazetidin-1-yl)-6-methylpyrido[3,4-d]pyrimidin-2-amine;

8-(3-ethoxy-3-isopropylazetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-ethylazetidine-3-carbonitrile;

1-(2-((2-ethoxy-4-(4-methyl-4H-1,2,4-triazol-3-yl)phenyl)amino)-6-methylpyrido[3,4-d]pyrimidin-8-yl)-3-isopropylazetidine-3-carbonitrile;

1-(2-((2-ethoxy-4-(4-methyl-4H-1,2,4-triazol-3-yl)phenyl)amino)-6-methylpyrido[3,4-d]pyrimidin-8-yl)-2,2,3-trimethylazetidine-3-carbonitrile;

N-(2-ethoxy-4-(4-methyl-4H-1,2,4-triazol-3-yl)phenyl)-8-(3-methoxy-2,2-dimethylazetidin-1-yl)-6-methylpyrido[3,4-d]pyrimidin-2-amine;

N-(2-ethoxy-4-(4-methyl-4H-1,2,4-triazol-3-yl)phenyl)-8-(3-methoxy-2,2,3-trimethylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-2,2-dimethylazetidine-3-carbonitrile;

N2-(2-methoxy-4-(4-methyl-4H-1,2,4-triazol-3-yl)phenyl)-6-methyl-N8-(1-methylpiperidin-4-yl)pyrido[3,4-d]pyrimidine-2,8-diamine;

8-(4-(dimethylamino)piperidin-1-yl)-N-(2-methoxy-4-(4-methyl-4H-1,2,4-triazol-3-yl)phenyl)-6-methylpyrido[3,4-d]pyrimidin-2-amine;

N2-(2-methoxy-4-(4-methyl-4H-1,2,4-triazol-3-yl)phenyl)-6-methyl-N8-((tetrahydro-2H-pyran-4-yl)methyl)pyrido[3,4-d]pyrimidine-2,8-diamine;

N2-(2-methoxy-4-(4-methyl-4H-1,2,4-triazol-3-yl)phenyl)-6-methyl-N8-((4-methyltetrahydro-2H-pyran-4-yl)methyl)pyrido[3,4-d]pyrimidine-2,8-diamine;

4-ethyl-1-(2-((2-methoxy-4-(4-methyl-4H-1,2,4-triazol-3-yl)phenyl)amino)-6-methylpyrido[3,4-d]pyrimidin-8-yl)piperidine-4-carbonitrile;

N2-(2-methoxy-4-(4-methyl-4H-1,2,4-triazol-3-yl)phenyl)-6-methyl-N8-(2-(3-methyltetrahydrofuran-3-yl)ethyl)pyrido[3,4-d]pyrimidine-2,8-diamine;

N2-(2-methoxy-4-(4-methyl-4H-1,2,4-triazol-3-yl)phenyl)-6-methyl-N8-(1-(tetrahydro-2H-pyran-4-yl)ethyl)pyrido[3,4-d]pyrimidine-2,8-diamine;

N2-(2-methoxy-4-(4-methyl-4H-1,2,4-triazol-3-yl)phenyl)-6-methyl-N8-(pentan-3-yl)pyrido[3,4-d]pyrimidine-2,8-diamine;

N2-(2-methoxy-4-(4-methyl-4H-1,2,4-triazol-3-yl)phenyl)-6-methyl-N8-(tetrahydrofuran-3-yl)pyrido[3,4-d]pyrimidine-2,8-diamine;

8-(3-ethoxy-3-methylazetidin-1-yl)-N-(2-methoxy-4-(4-methyl-4H-1,2,4-triazol-3-yl)phenyl)-6-methylpyrido[3,4-d]pyrimidin-2-amine;

8-(3-ethyl-3-methoxyazetidin-1-yl)-N-(2-methoxy-4-(4-methyl-4H-1,2,4-triazol-3-yl)phenyl)-6-methylpyrido[3,4-d]pyrimidin-2-amine;

8-(3-ethoxy-3-ethylazetidin-1-yl)-N-(2-methoxy-4-(4-methyl-4H-1,2,4-triazol-3-yl)phenyl)-6-methylpyrido[3,4-d]pyrimidin-2-amine;

8-(3-isopropyl-3-methoxyazetidin-1-yl)-N-(2-methoxy-4-(4-methyl-4H-1,2,4-triazol-3-yl)phenyl)-6-methylpyrido[3,4-d]pyrimidin-2-amine;

8-(3-ethoxy-3-isopropylazetidin-1-yl)-N-(2-methoxy-4-(4-methyl-4H-1,2,4-triazol-3-yl)phenyl)-6-methylpyrido[3,4-d]pyrimidin-2-amine;

3-ethyl-1-(2-((2-methoxy-4-(4-methyl-4H-1,2,4-triazol-3-yl)phenyl)amino)-6-methylpyrido[3,4-d]pyrimidin-8-yl)azetidine-3-carbonitrile;

3-isopropyl-1-(2-((2-methoxy-4-(4-methyl-4H-1,2,4-triazol-3-yl)phenyl)amino)-6-methylpyrido[3,4-d]pyrimidin-8-yl)azetidine-3-carbonitrile;

1-(2-((2-methoxy-4-(4-methyl-4H-1,2,4-triazol-3-yl)phenyl)amino)-6-methylpyrido[3,4-d]pyrimidin-8-yl)-2,2,3-trimethylazetidine-3-carbonitrile;

8-(3-methoxy-2,2-dimethylazetidin-1-yl)-N-(2-methoxy-4-(4-methyl-4H-1,2,4-triazol-3-yl)phenyl)-6-methylpyrido[3,4-d]pyrimidin-2-amine;

8-(3-methoxy-2,2,3-trimethylazetidin-1-yl)-N-(2-methoxy-4-(4-methyl-4H-1,2,4-triazol-3-yl)phenyl)-6-methylpyrido[3,4-d]pyrimidin-2-amine;

1-(2-((2-methoxy-4-(4-methyl-4H-1,2,4-triazol-3-yl)phenyl)amino)-6-methylpyrido[3,4-d]pyrimidin-8-yl)-2,2-dimethylazetidine-3-carbonitrile;

8-(3,3-dimethylazetidin-1-yl)-N-(2-methoxy-4-(1-methyl-1H-tetrazol-5-yl)phenyl)-6-methylpyrido[3,4-d]pyrimidin-2-amine;

1-(2-((2-methoxy-4-(1-methyl-1H-tetrazol-5-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-tetrazol-5-yl)phenyl)-6-methylpyrido[3,4-d]pyrimidin-2-amine;

N-(2-methoxy-4-(1-methyl-1H-tetrazol-5-yl)phenyl)-8-(4-methoxypiperidin-1-yl)-6-methylpyrido[3,4-d]pyrimidin-2-amine;

N-(2-methoxy-4-(1-methyl-1H-tetrazol-5-yl)phenyl)-8-(4-methoxy-4-methylpiperidin-1-yl)-6-methylpyrido[3,4-d]pyrimidin-2-amine;

N-(2-methoxy-4-(1-methyl-1H-tetrazol-5-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-tetrazol-5-yl)phenyl)amino)-6-methylpyrido[3,4-d]pyrimidin-8-yl)-3-methylazetidine-3-carbonitrile;

N2-(2-methoxy-4-(1-methyl-1H-tetrazol-5-yl)phenyl)-6-methyl-N8-((3-methyltetrahydrofuran-3-yl)methyl)pyrido[3,4-d]pyrimidine-2,8-diamine;

N-(2-methoxy-4-(1-methyl-1H-tetrazol-5-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-tetrazol-5-yl)phenyl)-6-methyl-N8-(tetrahydro-2H-pyran-4-yl)pyrido[3,4-d]pyrimidine-2,8-diamine;

N-(2-methoxy-4-(1-methyl-1H-tetrazol-5-yl)phenyl)-6-methyl-8-(7-oxa-2-azaspiro[3.5]nonan-2-yl)pyrido[3,4-d]pyrimidin-2-amine;

N2-(2-methoxy-4-(1-methyl-1H-tetrazol-5-yl)phenyl)-6-methyl-N8-neopentylpyrido[3,4-d]pyrimidine-2,8-diamine;

N-(2-(difluoromethoxy)-4-(4-methyl-4H-1,2,4-triazol-3-yl)phenyl)-8-(3,3-dimethylazetidin-1-yl)-6-methylpyrido[3,4-d]pyrimidin-2-amine;

1-(2-((2-(difluoromethoxy)-4-(4-methyl-4H-1,2,4-triazol-3-yl)phenyl)amino)-6-methylpyrido[3,4-d]pyrimidin-8-yl)-4-methylpiperidine-4-carbonitrile;

N-(2-(difluoromethoxy)-4-(4-methyl-4H-1,2,4-triazol-3-yl)phenyl)-8-(3-methoxy-3-methylazetidin-1-yl)-6-methylpyrido[3,4-d]pyrimidin-2-amine;

N-(2-(difluoromethoxy)-4-(4-methyl-4H-1,2,4-triazol-3-yl)phenyl)-8-(4-methoxypiperidin-1-yl)-6-methylpyrido[3,4-d]pyrimidin-2-amine;

N-(2-(difluoromethoxy)-4-(4-methyl-4H-1,2,4-triazol-3-yl)phenyl)-8-(4-methoxy-4-methylpiperidin-1-yl)-6-methylpyrido[3,4-d]pyrimidin-2-amine;

N-(2-(difluoromethoxy)-4-(4-methyl-4H-1,2,4-triazol-3-yl)phenyl)-6-methyl-8-(1-oxa-6-azaspiro[3.3]heptan-6-yl)pyrido[3,4-d]pyrimidin-2-amine;

1-(2-((2-(difluoromethoxy)-4-(4-methyl-4H-1,2,4-triazol-3-yl)phenyl)amino)-6-methylpyrido[3,4-d]pyrimidin-8-yl)-3-methylazetidine-3-carbonitrile;

N2-(2-(difluoromethoxy)-4-(4-methyl-4H-1,2,4-triazol-3-yl)phenyl)-6-methyl-N8-((3-methyltetrahydrofuran-3-yl)methyl)pyrido[3,4-d]pyrimidine-2,8-diamine;

N-(2-(difluoromethoxy)-4-(4-methyl-4H-1,2,4-triazol-3-yl)phenyl)-6-methyl-8-(2-oxa-7-azaspiro[4.4]nonan-7-yl)pyrido[3,4-d]pyrimidin-2-amine;

N2-(2-(difluoromethoxy)-4-(4-methyl-4H-1,2,4-triazol-3-yl)phenyl)-6-methyl-N8-(tetrahydro-2H-pyran-4-yl)pyrido[3,4-d]pyrimidine-2,8-diamine;

N-(2-(difluoromethoxy)-4-(4-methyl-4H-1,2,4-triazol-3-yl)phenyl)-6-methyl-8-(7-oxa-2-azaspiro[3.5]nonan-2-yl)pyrido[3,4-d]pyrimidin-2-amine;

N2-(2-(difluoromethoxy)-4-(4-methyl-4H-1,2,4-triazol-3-yl)phenyl)-6-methyl-N8-neopentylpyrido[3,4-d]pyrimidine-2,8-diamine;

8-(3,3-dimethylazetidin-1-yl)-N-(4-(4-ethyl-4H-1,2,4-triazol-3-yl)-2-methoxyphenyl)-6-methylpyrido[3,4-d]pyrimidin-2-amine;

1-(2-((4-(4-ethyl-4H-1,2,4-triazol-3-yl)-2-methoxyphenyl)amino)-6-methylpyrido[3,4-d]pyrimidin-8-yl)-4-methylpiperidine-4-carbonitrile;

N-(4-(4-ethyl-4H-1,2,4-triazol-3-yl)-2-methoxyphenyl)-8-(3-methoxy-3-methylazetidin-1-yl)-6-methylpyrido[3,4-d]pyrimidin-2-amine;

N-(4-(4-ethyl-4H-1,2,4-triazol-3-yl)-2-methoxyphenyl)-8-(4-methoxypiperidin-1-yl)-6-methylpyrido[3,4-d]pyrimidin-2-amine;

N-(4-(4-ethyl-4H-1,2,4-triazol-3-yl)-2-methoxyphenyl)-8-(4-methoxy-4-methylpiperidin-1-yl)-6-methylpyrido[3,4-d]pyrimidin-2-amine;

N-(4-(4-ethyl-4H-1,2,4-triazol-3-yl)-2-methoxyphenyl)-6-methyl-8-(1-oxa-6-azaspiro[3.3]heptan-6-yl)pyrido[3,4-d]pyrimidin-2-amine;

1-(2-((4-(4-ethyl-4H-1,2,4-triazol-3-yl)-2-methoxyphenyl)amino)-6-methylpyrido[3,4-d]pyrimidin-8-yl)-3-methylazetidine-3-carbonitrile;

N2-(4-(4-ethyl-4H-1,2,4-triazol-3-yl)-2-methoxyphenyl)-6-methyl-N8-((3-methyltetrahydrofuran-3-yl)methyl)pyrido[3,4-d]pyrimidine-2,8-diamine;

N-(4-(4-ethyl-4H-1,2,4-triazol-3-yl)-2-methoxyphenyl)-6-methyl-8-(2-oxa-7-azaspiro[4.4]nonan-7-yl)pyrido[3,4-d]pyrimidin-2-amine;

N2-(4-(4-ethyl-4H-1,2,4-triazol-3-yl)-2-methoxyphenyl)-6-methyl-N8-(tetrahydro-2H-pyran-4-yl)pyrido[3,4-d]pyrimidine-2,8-diamine;

N-(4-(4-ethyl-4H-1,2,4-triazol-3-yl)-2-methoxyphenyl)-6-methyl-8-(7-oxa-2-azaspiro[3.5]nonan-2-yl)pyrido[3,4-d]pyrimidin-2-amine;

N2-(4-(4-ethyl-4H-1,2,4-triazol-3-yl)-2-methoxyphenyl)-6-methyl-N8-neopentylpyrido[3,4-d]pyrimidine-2,8-diamine;

8-(3,3-dimethylazetidin-1-yl)-N-(2-ethoxy-4-(4-ethyl-4H-1,2,4-triazol-3-yl)phenyl)-6-methylpyrido[3,4-d]pyrimidin-2-amine;

1-(2-((2-ethoxy-4-(4-ethyl-4H-1,2,4-triazol-3-yl)phenyl)amino)-6-methylpyrido[3,4-d]pyrimidin-8-yl)-4-methylpiperidine-4-carbonitrile;

N-(2-ethoxy-4-(4-ethyl-4H-1,2,4-triazol-3-yl)phenyl)-8-(3-methoxy-3-methylazetidin-1-yl)-6-methylpyrido[3,4-d]pyrimidin-2-amine;

N-(2-ethoxy-4-(4-ethyl-4H-1,2,4-triazol-3-yl)phenyl)-8-(4-methoxypiperidin-1-yl)-6-methylpyrido[3,4-d]pyrimidin-2-amine;

N-(2-ethoxy-4-(4-ethyl-4H-1,2,4-triazol-3-yl)phenyl)-8-(4-methoxy-4-methylpiperidin-1-yl)-6-methylpyrido[3,4-d]pyrimidin-2-amine;

N-(2-ethoxy-4-(4-ethyl-4H-1,2,4-triazol-3-yl)phenyl)-6-methyl-8-(1-oxa-6-azaspiro[3.3]heptan-6-yl)pyrido[3,4-d]pyrimidin-2-amine;

1-(2-((2-ethoxy-4-(4-ethyl-4H-1,2,4-triazol-3-yl)phenyl)amino)-6-methylpyrido[3,4-d]pyrimidin-8-yl)-3-methylazetidine-3-carbonitrile;

N2-(2-ethoxy-4-(4-ethyl-4H-1,2,4-triazol-3-yl)phenyl)-6-methyl-N8-((3-methyltetrahydrofuran-3-yl)methyl)pyrido[3,4-d]pyrimidine-2,8-diamine;

N-(2-ethoxy-4-(4-ethyl-4H-1,2,4-triazol-3-yl)phenyl)-6-methyl-8-(2-oxa-7-azaspiro[4.4]nonan-7-yl)pyrido[3,4-d]pyrimidin-2-amine;

N2-(2-ethoxy-4-(4-ethyl-4H-1,2,4-triazol-3-yl)phenyl)-6-methyl-N8-(tetrahydro-2H-pyran-4-yl)pyrido[3,4-d]pyrimidine-2,8-diamine;

N-(2-ethoxy-4-(4-ethyl-4H-1,2,4-triazol-3-yl)phenyl)-6-methyl-8-(7-oxa-2-azaspiro[3.5]nonan-2-yl)pyrido[3,4-d]pyrimidin-2-amine;

N2-(2-ethoxy-4-(4-ethyl-4H-1,2,4-triazol-3-yl)phenyl)-6-methyl-N8-neopentylpyrido[3,4-d]pyrimidine-2,8-diamine;

N-(4-(4,5-dimethyl-4H-1,2,4-triazol-3-yl)-2-methoxyphenyl)-8-(3,3-dimethylazetidin-1-yl)-6-methylpyrido[3,4-d]pyrimidin-2-amine;

1-(2-((4-(4,5-dimethyl-4H-1,2,4-triazol-3-yl)-2-methoxyphenyl)amino)-6-methylpyrido[3,4-d]pyrimidin-8-yl)-4-methylpiperidine-4-carbonitrile;

N-(4-(4,5-dimethyl-4H-1,2,4-triazol-3-yl)-2-methoxyphenyl)-8-(3-methoxy-3-methylazetidin-1-yl)-6-methylpyrido[3,4-d]pyrimidin-2-amine;

N-(4-(4,5-dimethyl-4H-1,2,4-triazol-3-yl)-2-methoxyphenyl)-8-(4-methoxypiperidin-1-yl)-6-methylpyrido[3,4-d]pyrimidin-2-amine;

N-(4-(4,5-dimethyl-4H-1,2,4-triazol-3-yl)-2-methoxyphenyl)-8-(4-methoxy-4-methylpiperidin-1-yl)-6-methylpyrido[3,4-d]pyrimidin-2-amine;

N-(4-(4,5-dimethyl-4H-1,2,4-triazol-3-yl)-2-methoxyphenyl)-6-methyl-8-(1-oxa-6-azaspiro[3.3]heptan-6-yl)pyrido[3,4-d]pyrimidin-2-amine;

1-(2-((4-(4,5-dimethyl-4H-1,2,4-triazol-3-yl)-2-methoxyphenyl)amino)-6-methylpyrido[3,4-d]pyrimidin-8-yl)-3-methylazetidine-3-carbonitrile;

N2-(4-(4,5-dimethyl-4H-1,2,4-triazol-3-yl)-2-methoxyphenyl)-6-methyl-N8-((3-methyltetrahydrofuran-3-yl)methyl)pyrido[3,4-d]pyrimidine-2,8-diamine;

N-(4-(4,5-dimethyl-4H-1,2,4-triazol-3-yl)-2-methoxyphenyl)-6-methyl-8-(2-oxa-7-azaspiro[4.4]nonan-7-yl)pyrido[3,4-d]pyrimidin-2-amine;

N2-(4-(4,5-dimethyl-4H-1,2,4-triazol-3-yl)-2-methoxyphenyl)-6-methyl-N8-(tetrahydro-2H-pyran-4-yl)pyrido[3,4-d]pyrimidine-2,8-diamine;

N-(4-(4,5-dimethyl-4H-1,2,4-triazol-3-yl)-2-methoxyphenyl)-6-methyl-8-(7-oxa-2-azaspiro[3.5]nonan-2-yl)pyrido[3,4-d]pyrimidin-2-amine;

N2-(4-(4,5-dimethyl-4H-1,2,4-triazol-3-yl)-2-methoxyphenyl)-6-methyl-N8-neopentylpyrido[3,4-d]pyrimidine-2,8-diamine;

N-(4-(4,5-dimethyl-4H-1,2,4-triazol-3-yl)-2-ethoxyphenyl)-8-(3,3-dimethylazetidin-1-yl)-6-methylpyrido[3,4-d]pyrimidin-2-amine;

1-(2-((4-(4,5-dimethyl-4H-1,2,4-triazol-3-yl)-2-ethoxyphenyl)amino)-6-methylpyrido[3,4-d]pyrimidin-8-yl)-4-methylpiperidine-4-carbonitrile;

N-(4-(4,5-dimethyl-4H-1,2,4-triazol-3-yl)-2-ethoxyphenyl)-8-(3-methoxy-3-methylazetidin-1-yl)-6-methylpyrido[3,4-d]pyrimidin-2-amine;

N-(4-(4,5-dimethyl-4H-1,2,4-triazol-3-yl)-2-ethoxyphenyl)-8-(4-methoxypiperidin-1-yl)-6-methylpyrido[3,4-d]pyrimidin-2-amine;

N-(4-(4,5-dimethyl-4H-1,2,4-triazol-3-yl)-2-ethoxyphenyl)-8-(4-methoxy-4-methylpiperidin-1-yl)-6-methylpyrido[3,4-d]pyrimidin-2-amine;

N-(4-(4,5-dimethyl-4H-1,2,4-triazol-3-yl)-2-ethoxyphenyl)-6-methyl-8-(1-oxa-6-azaspiro[3.3]heptan-6-yl)pyrido[3,4-d]pyrimidin-2-amine;

1-(2-((4-(4,5-dimethyl-4H-1,2,4-triazol-3-yl)-2-ethoxyphenyl)amino)-6-methylpyrido[3,4-d]pyrimidin-8-yl)-3-methylazetidine-3-carbonitrile;

N2-(4-(4,5-dimethyl-4H-1,2,4-triazol-3-yl)-2-ethoxyphenyl)-6-methyl-N8-((3-methyltetrahydrofuran-3-yl)methyl)pyrido[3,4-d]pyrimidine-2,8-diamine;

N-(4-(4,5-dimethyl-4H-1,2,4-triazol-3-yl)-2-ethoxyphenyl)-6-methyl-8-(2-oxa-7-azaspiro[4.4]nonan-7-yl)pyrido[3,4-d]pyrimidin-2-amine;

N2-(4-(4,5-dimethyl-4H-1,2,4-triazol-3-yl)-2-ethoxyphenyl)-6-methyl-N8-(tetrahydro-2H-pyran-4-yl)pyrido[3,4-d]pyrimidine-2,8-diamine;

N-(4-(4,5-dimethyl-4H-1,2,4-triazol-3-yl)-2-ethoxyphenyl)-6-methyl-8-(7-oxa-2-azaspiro[3.5]nonan-2-yl)pyrido[3,4-d]pyrimidin-2-amine;

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

8-(3,3-dimethylazetidin-1-yl)-N-(2-methoxy-4-(1-methyl-1H-1,2,3-triazol-5-yl)phenyl)-6-methylpyrido[3,4-d]pyrimidin-2-amine;

1-(2-((2-methoxy-4-(1-methyl-1H-1,2,3-triazol-5-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-1,2,3-triazol-5-yl)phenyl)-6-methylpyrido[3,4-d]pyrimidin-2-amine;

N-(2-methoxy-4-methyl-1H-1,2,3-triazol-5-yl)phenyl)-8-(4-methoxypiperidin-1-yl)-6-methylpyrido[3,4-d]pyrimidin-2-amine;

N-(2-methoxy-4-methyl-1H-1,2,3-triazol-5-yl)phenyl)-8-(4-methoxy-4-methylpiperidin-1-yl)-6-methylpyrido[3,4-d]pyrimidin-2-amine;

N-(2-methoxy-4-methyl-1H-1,2,3-triazol-5-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-1,2,3-triazol-5-yl)phenyl)amino)-6-methylpyrido[3,4-d]pyrimidin-8-yl)-3-methylazetidine-3-carbonitrile;

N2-(2-methoxy-4-(1-methyl-1H-1,2,3-triazol-5-yl)phenyl)-6-methyl-N8-((3-methyltetrahydrofuran-3-yl)methyl)pyrido[3,4-d]pyrimidine-2,8-diamine;

N-(2-methoxy-4-methyl-1H-1,2,3-triazol-5-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-1,2,3-triazol-5-yl)phenyl)-6-methyl-N8-(tetrahydro-2H-pyran-4-yl)pyrido[3,4-d]pyrimidine-2,8-diamine;

N-(2-methoxy-4-methyl-1H-1,2,3-triazol-5-yl)phenyl)-6-methyl-8-(7-oxa-2-azaspiro[3.5]nonan-2-yl)pyrido[3,4-d]pyrimidin-2-amine;

N-(4-(1,2-dimethyl-1H-imidazol-5-yl)-2-methoxyphenyl)-8-(3,3-dimethylazetidin-1-yl)-6-methylpyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)-4-methylpiperidine-4-carbonitrile;

N-(4-(1,2-dimethyl-1H-imidazol-5-yl)-2-methoxyphenyl)-8-(3-methoxy-3-methylazetidin-1-yl)-6-methylpyrido[3,4-d]pyrimidin-2-amine;

N-(4-(1,2-dimethyl-1H-imidazol-5-yl)-2-methoxyphenyl)-8-(4-methoxypiperidin-1-yl)-6-methylpyrido[3,4-d]pyrimidin-2-amine;

N-(4-(1,2-dimethyl-1H-imidazol-5-yl)-2-methoxyphenyl)-8-(4-methoxy-4-methylpiperidin-1-yl)-6-methylpyrido[3,4-d]pyrimidin-2-amine;

N-(4-(1,2-dimethyl-1H-imidazol-5-yl)-2-methoxyphenyl)-6-methyl-8-(1-oxa-6-azaspiro[3.3]heptan-6-yl)pyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)-3-methylazetidine-3-carbonitrile;

N-(4-(1,2-dimethyl-1H-imidazol-5-yl)-2-methoxyphenyl)-6-methyl-8-(2-oxa-7-azaspiro[4.4]nonan-7-yl)pyrido[3,4-d]pyrimidin-2-amine;

N2-(4-(1,2-dimethyl-1H-imidazol-5-yl)-2-methoxyphenyl)-6-methyl-N8-(tetrahydro-2H-pyran-4-yl)pyrido[3,4-d]pyrimidine-2,8-diamine;

N-(4-(1,2-dimethyl-1H-imidazol-5-yl)-2-methoxyphenyl)-6-methyl-8-(7-oxa-2-azaspiro[3.5]nonan-2-yl)pyrido[3,4-d]pyrimidin-2-amine;

N-(4-(1,5-dimethyl-1H-imidazol-2-yl)-2-methoxyphenyl)-8-(3,3-dimethylazetidin-1-yl)-6-methylpyrido[3,4-d]pyrimidin-2-amine;

1-(2-((4-(1,5-dimethyl-1H-imidazol-2-yl)-2-methoxyphenyl)amino)-6-methylpyrido[3,4-d]pyrimidin-8-yl)-4-methylpiperidine-4-carbonitrile;

N-(4-(1,5-dimethyl-1H-imidazol-2-yl)-2-methoxyphenyl)-8-(3-methoxy-3-methylazetidin-1-yl)-6-methylpyrido[3,4-d]pyrimidin-2-amine;

N-(4-(1,5-dimethyl-1H-imidazol-2-yl)-2-methoxyphenyl)-8-(4-methoxypiperidin-1-yl)-6-methylpyrido[3,4-d]pyrimidin-2-amine;

N-(4-(1,5-dimethyl-1H-imidazol-2-yl)-2-methoxyphenyl)-8-(4-methoxy-4-methylpiperidin-1-yl)-6-methylpyrido[3,4-d]pyrimidin-2-amine;

N-(4-(1,5-dimethyl-1H-imidazol-2-yl)-2-methoxyphenyl)-6-methyl-8-(1-oxa-6-azaspiro[3.3]heptan-6-yl)pyrido[3,4-d]pyrimidin-2-amine;

1-(2-((4-(1,5-dimethyl-1H-imidazol-2-yl)-2-methoxyphenyl)amino)-6-methylpyrido[3,4-d]pyrimidin-8-yl)-3-methylazetidine-3-carbonitrile;

N2-(4-(1,5-dimethyl-1H-imidazol-2-yl)-2-methoxyphenyl)-6-methyl-N8-((3-methyltetrahydrofuran-3-yl)methyl)pyrido[3,4-d]pyrimidine-2,8-diamine;

N-(4-(1,5-dimethyl-1H-imidazol-2-yl)-2-methoxyphenyl)-6-methyl-8-(2-oxa-7-azaspiro[4.4]nonan-7-yl)pyrido[3,4-d]pyrimidin-2-amine;

N2-(4-(1,5-dimethyl-1H-imidazol-2-yl)-2-methoxyphenyl)-6-methyl-N8-(tetrahydro-2H-pyran-4-yl)pyrido[3,4-d]pyrimidine-2,8-diamine;

N-(4-(1,5-dimethyl-1H-imidazol-2-yl)-2-methoxyphenyl)-6-methyl-8-(7-oxa-2-azaspiro[3.5]nonan-2-yl)pyrido[3,4-d]pyrimidin-2-amine;

N2-(4-(1,5-dimethyl-1H-imidazol-2-yl)-2-methoxyphenyl)-6-methyl-N8-neopentylpyrido[3,4-d]pyrimidine-2,8-diamine;

8-(3,3-dimethylazetidin-1-yl)-N-(2-methoxy-4-(1-methyl-1H-imidazol-2-yl)phenyl)-6-methylpyrido[3,4-d]pyrimidin-2-amine;

1-(2-((2-methoxy-4-(1-methyl-1H-imidazol-2-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-imidazol-2-yl)phenyl)-6-methylpyrido[3,4-d]pyrimidin-2-amine;

N-(2-methoxy-4-(1-methyl-1H-imidazol-2-yl)phenyl)-8-(4-methoxypiperidin-1-yl)-6-methylpyrido[3,4-d]pyrimidin-2-amine;

N-(2-methoxy-4-(1-methyl-1H-imidazol-2-yl)phenyl)-8-(4-methoxy-4-methylpiperidin-1-yl)-6-methylpyrido[3,4-d]pyrimidin-2-amine;

N-(2-methoxy-4-(1-methyl-1H-imidazol-2-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-imidazol-2-yl)phenyl)amino)-6-methylpyrido[3,4-d]pyrimidin-8-yl)-3-methylazetidine-3-carbonitrile;

N2-(2-methoxy-4-(1-methyl-1H-imidazol-2-yl)phenyl)-6-methyl-N8-((3-methyltetrahydrofuran-3-yl)methyl)pyrido[3,4-d]pyrimidine-2,8-diamine;

N-(2-methoxy-4-(1-methyl-1H-imidazol-2-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-imidazol-2-yl)phenyl)-6-methyl-N8-(tetrahydro-2H-pyran-4-yl)pyrido[3,4-d]pyrimidine-2,8-diamine;

N-(2-methoxy-4-(1-methyl-1H-imidazol-2-yl)phenyl)-6-methyl-8-(7-oxa-2-azaspiro[3.5]nonan-2-yl)pyrido[3,4-d]pyrimidin-2-amine;

8-(3,3-dimethylazetidin-1-yl)-N-(4-(2,4-dimethyloxazol-5-yl)-2-methoxyphenyl)-6-methylpyrido[3,4-d]pyrimidin-2-amine;

1-(2-((4-(2,4-dimethyloxazol-5-yl)-2-methoxyphenyl)amino)-6-methylpyrido[3,4-d]pyrimidin-8-yl)-4-methylpiperidine-4-carbonitrile;

N-(4-(2,4-dimethyloxazol-5-yl)-2-methoxyphenyl)-8-(3-methoxy-3-methylazetidin-1-yl)-6-methylpyrido[3,4-d]pyrimidin-2-amine;

N-(4-(2,4-dimethyloxazol-5-yl)-2-methoxyphenyl)-8-(4-methoxypiperidin-1-yl)-6-methylpyrido[3,4-d]pyrimidin-2-amine;

N-(4-(2,4-dimethyloxazol-5-yl)-2-methoxyphenyl)-8-(4-methoxy-4-methylpiperidin-1-yl)-6-methylpyrido[3,4-d]pyrimidin-2-amine;

N-(4-(2,4-dimethyloxazol-5-yl)-2-methoxyphenyl)-6-methyl-8-(1-oxa-6-azaspiro[3.3]heptan-6-yl)pyrido[3,4-d]pyrimidin-2-amine;

1-(2-((4-(2,4-dimethyloxazol-5-yl)-2-methoxyphenyl)amino)-6-methylpyrido[3,4-d]pyrimidin-8-yl)-3-methylazetidine-3-carbonitrile;

N2-(4-(2,4-dimethyloxazol-5-yl)-2-methoxyphenyl)-6-methyl-N8-((3-methyltetrahydrofuran-3-yl)methyl)pyrido[3,4-d]pyrimidine-2,8-diamine;

N-(4-(2,4-dimethyloxazol-5-yl)-2-methoxyphenyl)-6-methyl-8-(2-oxa-7-azaspiro[4.4]nonan-7-yl)pyrido[3,4-d]pyrimidin-2-amine;

N2-(4-(2,4-dimethyloxazol-5-yl)-2-methoxyphenyl)-6-methyl-N8-(tetrahydro-2H-pyran-4-yl)pyrido[3,4-d]pyrimidine-2,8-diamine;

N-(4-(2,4-dimethyloxazol-5-yl)-2-methoxyphenyl)-6-methyl-8-(7-oxa-2-azaspiro[3.5]nonan-2-yl)pyrido[3,4-d]pyrimidin-2-amine;

N2-(4-(2,4-dimethyloxazol-5-yl)-2-methoxyphenyl)-6-methyl-N8-neopentylpyrido[3,4-d]pyrimidine-2,8-diamine;

8-(3,3-dimethylazetidin-1-yl)-N-(4-(2,4-dimethyloxazol-5-yl)-2-ethoxyphenyl)-6-methylpyrido[3,4-d]pyrimidin-2-amine;

1-(2-((4-(2,4-dimethyloxazol-5-yl)-2-ethoxyphenyl)amino)-6-methylpyrido[3,4-d]pyrimidin-8-yl)-4-methylpiperidine-4-carbonitrile;

N-(4-(2,4-dimethyloxazol-5-yl)-2-ethoxyphenyl)-8-(3-methoxy-3-methylazetidin-1-yl)-6-methylpyrido[3,4-d]pyrimidin-2-amine;

N-(4-(2,4-dimethyloxazol-5-yl)-2-ethoxyphenyl)-8-(4-methoxypiperidin-1-yl)-6-methylpyrido[3,4-d]pyrimidin-2-amine;

N-(4-(2,4-dimethyloxazol-5-yl)-2-ethoxyphenyl)-8-(4-methoxy-4-methylpiperidin-1-yl)-6-methylpyrido[3,4-d]pyrimidin-2-amine;

N-(4-(2,4-dimethyloxazol-5-yl)-2-ethoxyphenyl)-6-methyl-8-(1-oxa-6-azaspiro[3.3]heptan-6-yl)pyrido[3,4-d]pyrimidin-2-amine;

1-(2-((4-(2,4-dimethyloxazol-5-yl)-2-ethoxyphenyl)amino)-6-methylpyrido[3,4-d]pyrimidin-8-yl)-3-methylazetidine-3-carbonitrile;

N2-(4-(2,4-dimethyloxazol-5-yl)-2-ethoxyphenyl)-6-methyl-N8-((3-methyltetrahydrofuran-3-yl)methyl)pyrido[3,4-d]pyrimidine-2,8-diamine;

N-(4-(2,4-dimethyloxazol-5-yl)-2-ethoxyphenyl)-6-methyl-8-(2-oxa-7-azaspiro[4.4]nonan-7-yl)pyrido[3,4-d]pyrimidin-2-amine;

N2-(4-(2,4-dimethyloxazol-5-yl)-2-ethoxyphenyl)-6-methyl-N8-(tetrahydro-2H-pyran-4-yl)pyrido[3,4-d]pyrimidine-2,8-diamine;

N-(4-(2,4-dimethyloxazol-5-yl)-2-ethoxyphenyl)-6-methyl-8-(7-oxa-2-azaspiro[3.5]nonan-2-yl)pyrido[3,4-d]pyrimidin-2-amine;

N2-(4-(2,4-dimethyloxazol-5-yl)-2-ethoxyphenyl)-6-methyl-N8-neopentylpyrido[3,4-d]pyrimidine-2,8-diamine;

8-(3,3-dimethylazetidin-1-yl)-N-(4-(2,5-dimethyloxazol-4-yl)-2-methoxyphenyl)-6-methylpyrido[3,4-d]pyrimidin-2-amine;

1-(2-((4-(2,5-dimethyloxazol-4-yl)-2-methoxyphenyl)amino)-6-methylpyrido[3,4-d]pyrimidin-8-yl)-4-methylpiperidine-4-carbonitrile;

N-(4-(2,5-dimethyloxazol-4-yl)-2-methoxyphenyl)-8-(3-methoxy-3-methylazetidin-1-yl)-6-methylpyrido[3,4-d]pyrimidin-2-amine;

N-(4-(2,5-dimethyloxazol-4-yl)-2-methoxyphenyl)-8-(4-methoxypiperidin-1-yl)-6-methylpyrido[3,4-d]pyrimidin-2-amine;

N-(4-(2,5-dimethyloxazol-4-yl)-2-methoxyphenyl)-8-(4-methoxy-4-methylpiperidin-1-yl)-6-methylpyrido[3,4-d]pyrimidin-2-amine;

N-(4-(2,5-dimethyloxazol-4-yl)-2-methoxyphenyl)-6-methyl-8-(1-oxa-6-azaspiro[3.3]heptan-6-yl)pyrido[3,4-d]pyrimidin-2-amine;

1-(2-((4-(2,5-dimethyloxazol-4-yl)-2-methoxyphenyl)amino)-6-methylpyrido[3,4-d]pyrimidin-8-yl)-3-methylazetidine-3-carbonitrile;

N2-(4-(2,5-dimethyloxazol-4-yl)-2-methoxyphenyl)-6-methyl-N8-((3-methyltetrahydrofuran-3-yl)methyl)pyrido[3,4-d]pyrimidine-2,8-diamine;

N-(4-(2,5-dimethyloxazol-4-yl)-2-methoxyphenyl)-6-methyl-8-(2-oxa-7-azaspiro[4.4]nonan-7-yl)pyrido[3,4-d]pyrimidin-2-amine;

N2-(4-(2,5-dimethyloxazol-4-yl)-2-methoxyphenyl)-6-methyl-N8-(tetrahydro-2H-pyran-4-yl)pyrido[3,4-d]pyrimidine-2,8-diamine;

N-(4-(2,5-dimethyloxazol-4-yl)-2-methoxyphenyl)-6-methyl-8-(7-oxa-2-azaspiro[3.5]nonan-2-yl)pyrido[3,4-d]pyrimidin-2-amine;

N2-(4-(2,5-dimethyloxazol-4-yl)-2-methoxyphenyl)-6-methyl-N8-neopentylpyrido[3,4-d]pyrimidine-2,8-diamine;

8-(3,3-dimethylazetidin-1-yl)-N-(4-(2,5-dimethyloxazol-4-yl)-2-ethoxyphenyl)-6-methylpyrido[3,4-d]pyrimidin-2-amine;

1-(2-((4-(2,5-dimethyloxazol-4-yl)-2-ethoxyphenyl)amino)-6-methylpyrido[3,4-d]pyrimidin-8-yl)-4-methylpiperidine-4-carbonitrile;

N-(4-(2,5-dimethyloxazol-4-yl)-2-ethoxyphenyl)-8-(3-methoxy-3-methylazetidin-1-yl)-6-methylpyrido[3,4-d]pyrimidin-2-amine;

N-(4-(2,5-dimethyloxazol-4-yl)-2-ethoxyphenyl)-8-(4-methoxypiperidin-1-yl)-6-methylpyrido[3,4-d]pyrimidin-2-amine;

N-(4-(2,5-dimethyloxazol-4-yl)-2-ethoxyphenyl)-8-(4-methoxy-4-methylpiperidin-1-yl)-6-methylpyrido[3,4-d]pyrimidin-2-amine;

N-(4-(2,5-dimethyloxazol-4-yl)-2-ethoxyphenyl)-6-methyl-8-(1-oxa-6-azaspiro[3.3]heptan-6-yl)pyrido[3,4-d]pyrimidin-2-amine;

1-(2-((4-(2,5-dimethyloxazol-4-yl)-2-ethoxyphenyl)amino)-6-methylpyrido[3,4-d]pyrimidin-8-yl)-3-methylazetidine-3-carbonitrile;

N2-(4-(2,5-dimethyloxazol-4-yl)-2-ethoxyphenyl)-6-methyl-N8-((3-methyltetrahydrofuran-3-yl)methyl)pyrido[3,4-d]pyrimidine-2,8-diamine;

N-(4-(2,5-dimethyloxazol-4-yl)-2-ethoxyphenyl)-6-methyl-8-(2-oxa-7-azaspiro[4.4]nonan-7-yl)pyrido[3,4-d]pyrimidin-2-amine;

N2-(4-(2,5-dimethyloxazol-4-yl)-2-ethoxyphenyl)-6-methyl-N8-(tetrahydro-2H-pyran-4-yl)pyrido[3,4-d]pyrimidine-2,8-diamine;

N-(4-(2,5-dimethyloxazol-4-yl)-2-ethoxyphenyl)-6-methyl-8-(7-oxa-2-azaspiro[3.5]nonan-2-yl)pyrido[3,4-d]pyrimidin-2-amine; and N2-(4-(2,5-dimethyloxazol-4-yl)-2-ethoxyphenyl)-6-methyl-N8-neopentylpyrido[3,4-d]pyrimidine-2,8-diamine;

or a pharmaceutically acceptable salt or solvate thereof.

31. A method according to claim 1, wherein the MPS1 inhibitor is selected from the following:

N-cyclopropyl-4-(6-(2,3-difluoro-4-methoxyphenoxy)-8-((3,3,3-trifluoropropyl)amino)imidazo[1,2-b]pyridazin-3-yl)-2-methylbenzamide;

(R)-2-(4-fluorophenyl)-N-(4-(2-((2-methoxy-4-(methylsulfonyl)phenyl)amino)-[1,2,4]triazolo[1,5-a]pyridin-6-yl)phenyl)propanamide;

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

(S)-N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile; and N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof.

32. A method according to claim 1, wherein the MPS1 inhibitor is selected from the following:

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

(S)-N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile; and N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof.

* * * * *

UNITED STATES PATENT AND TRADEMARK OFFICE
CERTIFICATE OF CORRECTION

PATENT NO. : 11,207,321 B2
APPLICATION NO. : 16/623953
DATED : December 28, 2021
INVENTOR(S) : Lesley-Ann Martin and Joanna Nikitorwicz-Buniak Page 1 of 3

It is certified that error appears in the above-identified patent and that said Letters Patent is hereby corrected as shown below:

In the Claims

In Claim 26, at Column 62, Line 22, please replace:
"heterocyclyl, a 3 to membered heterocyclyl(1-2C)alkyl"
With:
-- heterocyclyl, a 3 to 6 membered heterocyclyl(1-2C)alkyl, --

In Claim 26, at Column 62, Line 45, please replace:
"wherein $R_E$ and $R_d$ are each independently selected from H or (1-4C)alkyl;"
With:
-- wherein $R_c$ and $R_d$ are each independently selected from H or (1-4C)alkyl; --

In Claim 26, at Column 62, Line 62, please replace:
"$A_3$ is CH and Ai or $A_2$ are selected from N or CH;"
With:
-- $A_3$ is CH and $A_1$ or $A_2$ are selected from N or CH; --

In Claim 26, at Column 63, Line 35, please replace:
"membered heterocyclic ring ring;"
With:
-- membered heterocyclic ring; --

In Claim 26, at Column 64, Line 4, please replace:
"and wherein $R_n$ is optionally further substituted by one"
With:
-- and wherein $R_{13}$ is optionally further substituted by one --

In Claim 26, at Column 64, Line 7, please replace:
"$R_{11}$ and $R_{10}$ are independently selected from hydrogen,"

Signed and Sealed this
Nineteenth Day of July, 2022

Katherine Kelly Vidal
*Director of the United States Patent and Trademark Office*

CERTIFICATE OF CORRECTION (continued)
U.S. Pat. No. 11,207,321 B2

With:
-- $R_{11}$ and $R_{14}$ are independently selected from hydrogen, --

In Claim 26, at Column 64, Line 41, please replace:
"(1-4C)alkyl group present in a Ru substituent group is"
With:
-- (1-4C)alkyl group present in a $R_1$ substituent group is --

In Claim 26, at Column 64, Line 62, please replace:
"wherein RC and $R^d$ are each independently selected"
With:
-- wherein $R^c$ and $R^d$ are each independently selected --

In Claim 26, at Column 65, Line 5, please replace:
"aryl; and wherein Re and $R^f$ are each independently"
With:
-- aryl; and wherein $R^e$ and $R^f$ are each independently --

In Claim 26, at Column 65, Line 7, please replace:
"cloalkyl-(1-4C)alkyl; or Re and $R^f$ can be linked such"
With:
-- cloalkyl-(1-4C)alkyl; or $R^e$ and $R^f$ can be linked such --

In Claim 26, at Column 65, Line 29, please replace:
"$L^1$ is absent or a linker group of the formula $[CR_8R_9]_n$–"
With:
-- $L^1$ is absent or a linker group of the formula $–[CR_8R_9]_n–$ --

In Claim 30, at Column 66, Line 15, please replace:
"N-(2-methoxy-4-(1-methylpiperidin-4-yl)oxy)phenyl)-5-"
With:
-- N-(2-methoxy-4-((1-methylpiperidin-4-yl)oxy)phenyl)-5- --

In Claim 30, at Column 66, Line 35, please replace:
"(3-methoxy-4-(8-(1-methyl-1H-pyrazol-4-yl)pyrido[3,4-"
With:
-- (3-methoxy-4-((8-(1-methyl-1H-pyrazol-4-yl)pyrido[3,4- --

In Claim 30, at Column 69, Line 19, please replace:
"3-((2-(2-methoxy-4-(1-methyl-1H-pyrazol-4-yl)phenyl)"
With:
-- 3-((2-((2-methoxy-4-(1-methyl-1H-pyrazol-4-yl)phenyl) --

In Claim 30, at Column 69, Line 55, please replace:
"1-(2-(2-methoxy-4-(1-methyl-1H-pyrazol-4-yl)phenyl)"

CERTIFICATE OF CORRECTION (continued)
U.S. Pat. No. 11,207,321 B2

With:
-- 1-(2-((2-methoxy-4-(1-methyl-1H-pyrazol-4-yl)phenyl) --

In Claim 30, at Column 70, Line 65, please replace:
"2-(2-((2-methoxy-4-(1-methyl-1H-pyrazol-4-yl)phenyl)"
With:
-- 2-((2-((2-methoxy-4-(1-methyl-1H-pyrazol-4-yl)phenyl) --

In Claim 30, at Column 71, Line 8, please replace:
"[3,4-d]pyrimidine-2,8-diamine"
With:
-- [3,4-d]pyrimidine-2,8-diamine; --

In Claim 30, at Column 82, Line 17, please replace:
"*N*-(2-methoxy-4-methyl-1*H*-1,2,3-triazol-5-yl)phenyl)-8-"
With:
-- *N*-(2-methoxy-4-(1-methyl-1*H*-1,2,3-triazol-5-yl)phenyl)-8- --

In Claim 30, at Column 82, Line 20, please replace:
"*N*-(2-methoxy-4-methyl-1*H*-1,2,3-triazol-5-yl)phenyl)-8-"
With:
-- *N*-(2-methoxy-4-(1-methyl-1*H*-1,2,3-triazol-5-yl)phenyl)-8- --

In Claim 30, at Column 82, Line 23, please replace:
"*N*-(2-methoxy-4-methyl-1*H*-1,2,3-triazol-5-yl)phenyl)-8-"
With:
-- *N*-(2-methoxy-4-(1-methyl-1*H*-1,2,3-triazol-5-yl)phenyl)-8- --

In Claim 30, at Column 82, Line 32, please replace:
"*N*-(2-methoxy-4-methyl-1*H*-1,2,3-triazol-5-yl)phenyl)-8-"
With:
-- *N*-(2-methoxy-4-(1-methyl-1*H*-1,2,3-triazol-5-yl)phenyl)-8- --

In Claim 30, at Column 82, Line 38, please replace:
"*N*-(2-methoxy-4-methyl-1*H*-1,2,3-triazol-5-yl)phenyl)-8-"
With:
-- *N*-(2-methoxy-4-(1-methyl-1*H*-1,2,3-triazol-5-yl)phenyl)-8- --